United States Patent [19]

Grobelny

[11] Patent Number: 5,888,992
[45] Date of Patent: *Mar. 30, 1999

[54] POLAR SUBSTITUTED HYDROCARBONS

[75] Inventor: Damian Wojciech Grobelny, Watsonia North, Australia

[73] Assignee: Narhex Limited, Wanchai, Hong Kong

[ * ] Notice: The term of this patent shall not extend beyond the expiration date of Pat. No. 5,679,688.

[21] Appl. No.: 612,894

[22] PCT Filed: Sep. 12, 1994

[86] PCT No.: PCT/AU94/00538

§ 371 Date: Apr. 29, 1996

§ 102(e) Date: Apr. 29, 1996

[87] PCT Pub. No.: WO95/07269

PCT Pub. Date: Mar. 16, 1995

Related U.S. Application Data

[63] Continuation-in-part of Ser. No. 295,855, filed as PCT/AU93/00103 Mar. 11, 1993, Pat. No. 5,679,688.

[30] Foreign Application Priority Data

| Mar. 11, 1992 | [AU] | Australia | PL1304 |
| Sep. 10, 1993 | [AU] | Australia | PM1161 |
| Jun. 24, 1994 | [AU] | Australia | PM6446 |

[51] Int. Cl.$^6$ .......................... A61K 31/65; A61K 31/27; C07C 323/57; C07D 207/14
[52] U.S. Cl. .............................................. 514/82; 546/23
[58] Field of Search .................. 546/23; 514/82

[56] References Cited

U.S. PATENT DOCUMENTS

| 3,330,857 | 7/1967 | Hess et al. | 260/471 |
| 5,011,910 | 4/1991 | Marshall et al. | 4530/329 |
| 5,086,165 | 2/1992 | Marshall et al. | 530/329 |
| 5,093,477 | 3/1992 | Mölling et al. | 530/328 |
| 5,116,835 | 5/1992 | Rüger et al. | 514/218 |
| 5,126,326 | 6/1992 | Anderson et al. | 514/17 |
| 5,132,400 | 7/1992 | Gammill et al. | 530/317 |
| 5,137,876 | 8/1992 | MacCoss et al. | 514/23 |
| 5,142,056 | 8/1992 | Kempe et al. | 546/265 |
| 5,145,951 | 9/1992 | Voges et al. | 530/530 |
| 5,151,438 | 9/1992 | Sham et al. | 514/357 |
| 5,162,538 | 11/1992 | Voges et al. | 546/336 |
| 5,164,300 | 11/1992 | Marshall et al. | 435/23 |
| 5,169,952 | 12/1992 | Askin et al. | 544/137 |
| 5,171,662 | 12/1992 | Sharma | 435/5 |
| 5,183,826 | 2/1993 | Bills et al. | 514/411 |
| 5,187,074 | 2/1993 | Treiber et al. | 435/41 |
| 5,188,950 | 2/1993 | Balani et al. | 435/120 |
| 5,192,668 | 3/1993 | Treiber et al. | 435/41 |
| 5,194,605 | 3/1993 | Greenlee et al. | 540/460 |
| 5,198,426 | 3/1993 | Hamby et al. | 514/19 |
| 5,212,157 | 5/1993 | Anderson et al. | 514/17 |
| 5,215,968 | 6/1993 | Nickel et al. | 514/19 |
| 5,221,665 | 6/1993 | Skiles | 514/18 |
| 5,221,667 | 6/1993 | Kaltenbronn et al. | 514/19 |
| 5,223,633 | 6/1993 | Hoppe et al. | 556/95 |
| 5,231,153 | 7/1993 | Talley | 526/181 |
| 5,235,039 | 8/1993 | Heath, Jr. et al. | 530/328 |
| 5,235,057 | 8/1993 | Kleemann et al. | 546/283.7 |
| 5,248,667 | 9/1993 | Bridge et al. | 514/15 |
| 5,250,563 | 10/1993 | Chen et al. | 514/411 |
| 5,254,682 | 10/1993 | Dhanoa et al. | 540/451 |
| 5,256,677 | 10/1993 | Sham et al. | 514/351 |
| 5,268,361 | 12/1993 | Almquist | 514/19 |
| 5,294,720 | 3/1994 | Jadhav et al. | 546/265 |
| 5,294,737 | 3/1994 | Ojima | 562/444 |
| 5,296,604 | 3/1994 | Hanko et al. | 546/169 |
| 5,461,067 | 10/1995 | Norbeck et al. | 514/333 |

FOREIGN PATENT DOCUMENTS

| 18051/88 | 12/1988 | Australia . |
| 35660/89 | 11/1989 | Australia . |
| 35700/89 | 11/1989 | Australia . |
| 40585/89 | 1/1990 | Australia . |
| 48493/90 | 5/1990 | Australia . |
| 40192/89 | 6/1990 | Australia . |
| 45665/89 | 6/1990 | Australia . |
| 46115/89 | 6/1990 | Australia . |
| 42308/89 | 8/1990 | Australia . |
| 50582/90 | 9/1990 | Australia . |
| 53716/90 | 11/1990 | Australia . |
| 54071/90 | 11/1990 | Australia . |
| 56289/90 | 12/1990 | Australia . |
| 60663/90 | 2/1991 | Australia . |
| 62084/90 | 3/1991 | Australia . |
| 63221/90 | 4/1991 | Australia . |
| 66334/90 | 5/1991 | Australia . |
| 66742/90 | 5/1991 | Australia . |
| 67877/90 | 6/1991 | Australia . |

(List continued on next page.)

OTHER PUBLICATIONS

Tomasseli et al., "The Complexities of AIDS: An Assessment of the HIV Protease as a Therapeutic Target," *Chimica Oggi*, May 1991, pp. 6–27.

Huff J.R., HIV Protease: A Novel Chemotherapeutic Target For AIDS, *Journal of Medicinal Chemistry*, vol. 34, No. 8, Aug. 1991, pp. 2305–2314.

Sham H. L. et al., Facile Synthesis of Potent HIV–1 Protease Inhibitors Containing a Novel Pseudo–Symmetric Dipeptide Isostere, *Journal of Chemical Society*, No. 13, 1993, pp. 1052–1053.

Budavri, S. et al., "The Merck Index," 11th Edition 1989 *Merck & Co.*, Monograph Nos. 32 36 47 423 481 1507 1540 1543 1575 1591 1592 1593 1597 2785 3676 3679 3680 3681 3716 3718 3751 3755 5760 5865 5867 5868 5938 6001 6047 7809 7811 7835 7836 7837 7839 7854 7855 9247 9257 9629.

Chong, K. et al., "Peptidomimetic HIV Protease Inhibitors: Phosphate Prodrugs with Improved Biological Activities", *J. Med. Chem.*, (1993) 36:2575–2577.

*Primary Examiner*—Mukund J. Shah
*Assistant Examiner*—Deepak R. Rao
*Attorney, Agent, or Firm*—Morgan & Finnegan, LLP

[57] ABSTRACT

The invention relates to retroviral protease inhibitors of the general formula (I): W—(A)$_n$—B—(A*)$_m$—V where W, A, B, A*, V, n and m are as defined herein, including related prodrugs of general formula (I) comprising a solubilizing group which is labile in vivo.

32 Claims, 3 Drawing Sheets

FOREIGN PATENT DOCUMENTS

| | | |
|---|---|---|
| 68229/90 | 6/1991 | Australia . |
| 69755/91 | 6/1991 | Australia . |
| 71319/91 | 8/1991 | Australia . |
| 71323/91 | 8/1991 | Australia . |
| 71320/91 | 9/1991 | Australia . |
| 74679/91 | 9/1991 | Australia . |
| 77326/91 | 12/1991 | Australia . |
| 78329/91 | 12/1991 | Australia . |
| 82054/91 | 12/1991 | Australia . |
| 78469/91 | 1/1992 | Australia . |
| 81910/91 | 1/1992 | Australia . |
| 82313/91 | 1/1992 | Australia . |
| 82334/91 | 1/1992 | Australia . |
| 83206/91 | 1/1992 | Australia . |
| 83740/91 | 3/1992 | Australia . |
| 87409/91 | 3/1992 | Australia . |
| 85877/91 | 4/1992 | Australia . |
| 87594/91 | 4/1992 | Australia . |
| 09851/91 | 5/1992 | Australia . |
| 87309/91 | 5/1992 | Australia . |
| 87715/91 | 5/1992 | Australia . |
| 88086/91 | 5/1992 | Australia . |
| 90531/91 | 5/1992 | Australia . |
| 90925/91 | 5/1992 | Australia . |
| 91251/91 | 5/1992 | Australia . |
| 91332/91 | 5/1992 | Australia . |
| 88900/91 | 6/1992 | Australia . |
| 89741/91 | 6/1992 | Australia . |
| 91223/91 | 6/1992 | Australia . |
| 89941/91 | 7/1992 | Australia . |
| 91790/91 | 7/1992 | Australia . |
| 10812/92 | 8/1992 | Australia . |
| 15310/92 | 9/1992 | Australia . |
| 17487/92 | 10/1992 | Australia . |
| 16007/92 | 11/1992 | Australia . |
| 18355/92 | 12/1992 | Australia . |
| 19373/92 | 1/1993 | Australia . |
| 19543/92 | 1/1993 | Australia . |
| 21944/92 | 1/1993 | Australia . |
| 24129/92 | 2/1993 | Australia . |
| 24251/92 | 2/1993 | Australia . |
| 22889/92 | 3/1993 | Australia . |
| 24690/92 | 3/1993 | Australia . |
| 26424/92 | 3/1993 | Australia . |
| 27253/92 | 4/1993 | Australia . |
| 28199/92 | 5/1993 | Australia . |
| 31628/93 | 6/1993 | Australia . |
| 34972/93 | 9/1993 | Australia . |
| 35165/93 | 9/1993 | Australia . |
| 38808/93 | 9/1993 | Australia . |
| 35621/93 | 10/1993 | Australia . |
| 37160/93 | 11/1993 | Australia . |
| 41230/93 | 12/1993 | Australia . |
| 41354/93 | 12/1993 | Australia . |
| 41659/93 | 1/1994 | Australia . |
| 44930/93 | 3/1994 | Australia . |
| 49072/93 | 5/1994 | Australia . |
| A6207/94 | 11/1994 | Australia . |
| 2005340 | 6/1990 | Canada . |
| 2071744 | 12/1992 | Canada . |
| 2072785 | 1/1993 | Canada . |
| 2075547 | 2/1993 | Canada . |
| 2077002 | 3/1993 | Canada . |
| 2112047 | 6/1994 | Canada . |
| 0337714 | 10/1989 | European Pat. Off. . |
| 0346847 | 12/1989 | European Pat. Off. . |
| 0357332 | 3/1990 | European Pat. Off. . |
| 0387231 | 9/1990 | European Pat. Off. . |
| 0432695 | 6/1991 | European Pat. Off. . |
| 0432974 | 6/1991 | European Pat. Off. . |
| 0432975 | 6/1991 | European Pat. Off. . |
| 0438311 | 7/1991 | European Pat. Off. . |
| 0528242 | 3/1992 | European Pat. Off. . |
| 0480714 | 4/1992 | European Pat. Off. . |
| 0487270 | 5/1992 | European Pat. Off. . |
| 0491538 | 6/1992 | European Pat. Off. . |
| 0519433 | 6/1992 | European Pat. Off. . |
| 0518675 | 12/1992 | European Pat. Off. . |
| 0521686 | 1/1993 | European Pat. Off. . |
| 052866 | 2/1993 | European Pat. Off. . |
| 0534511 | 3/1993 | European Pat. Off. . |
| 0604183 | 6/1993 | European Pat. Off. . |
| 0550924 | 7/1993 | European Pat. Off. . |
| 0553357 | 8/1993 | European Pat. Off. . |
| 0566237 | 10/1993 | European Pat. Off. . |
| 0574135 | 12/1993 | European Pat. Off. . |
| 0602306 | 6/1994 | European Pat. Off. . |
| 0604182 | 6/1994 | European Pat. Off. . |
| 0604184 | 6/1994 | European Pat. Off. . |
| 0604185 | 6/1994 | European Pat. Off. . |
| 0604186 | 6/1994 | European Pat. Off. . |
| 09191/90 | 2/1989 | WIPO . |
| 08221/91 | 6/1991 | WIPO . |
| 10442/91 | 7/1991 | WIPO . |
| 19000/91 | 12/1991 | WIPO . |
| 06992/92 | 4/1992 | WIPO . |
| 08701/92 | 5/1992 | WIPO . |
| 15319/92 | 9/1992 | WIPO . |
| 21696/92 | 12/1992 | WIPO . |
| 22313/92 | 12/1992 | WIPO . |
| 18006/03 | 9/1993 | WIPO . |

POLAR SUBSTITUTED HYDROCARBONS

This application is a national stage filing of PCT/AU94/00538 filed Sep. 12, 1994 which claims priority to Australian application numbers PM 6446 and PM 1161 filed Jun. 24, 1994 and Sep. 10, 1993 respectively, and a continuation-in-part application of U.S. Ser. No. 08/295,855, filed Nov. 11, 1994, now U.S. Pat. No. 5,679,688, which is a nation stage filing of PCT/AU93/00103 filed Mar. 11, 1993, which claims priority to Australian application number PL 1304 file Mar. 11, 1992.

TECHNICAL FIELD

The invention relates to certain hydrocarbon derivatives bearing polar substituents and their use in the inhibition of retroviral proteases, for example in the treatment of HIV viral infections such as acquired immunodeficiency syndrome (AIDS). The invention also relates to processes for preparing such hydrocarbon derivatives bearing polar substituents, to pharmaceutical compositions comprising them and to methods for the treatment or prophylaxis of retroviral infections. The invention also relates to a process for enhancing the water-solubility of a pharmaceutical or veterinary substance.

BACKGROUND ART

Human immunodeficiency virus (HIV) is a pathogenic retrovirus causing AIDS and its related disorders. The development of antiviral chemotherapy against AIDS has been the subject of an intense research effort since the discovery of HIV. (For a recent review on molecular targets for AIDS therapy see Mitsua et al, *Science*, 1990, pp 1533–1544). The HIV Proteases (HIV PR), and aspartyl proteases, were first suggested as a potential target for AIDS therapy by Kramer et al. (*Science* 231, 1580 (1986)). Since that time the potential usefulness of HIV PR inhibitors as effective agents in treatment of AIDS has been widely recognized (for a review of the HIV PR as a therapeutic target see Tomaselli et al. *Chimica Oggi*, May 1991, pp 6–27 and Huff J. R., *J. Med. Chem.* 34, 2314–2327 (1991)). Of the classical transition state mimics for aspartyl proteases, the hydroxyethylene, dihydroxyethylene, hydroxyethylamine and phosphinic acid isosteres appear to provide the greatest affinity for HIV PR. Many inhibitors of HIV PR have been shown to have an antiviral activity at concentrations in the nanomolar range in the different cell systems and are described as such in the patent literature.

OBJECTS OF THE INVENTION

It is an object of the present invention to provide compounds useful as retroviral protease inhibitors. It is another object of the present invention to provide pharmaceutical compositions comprising compounds useful for the treatment or prophylaxis of retroviral infections. It is a further object of the present invention to provide methods for the treatment or prophylaxis of retroviral infections, in particular AIDS. Other objects of the present invention are to provide processes for preparing compounds useful as retroviral protease inhibitors, and processes for enhancing the water-solubility of pharmaceutical or veterinary substances, in particular retroviral protease inhibitors.

SUMMARY OF THE INVENTION

The invention provides compounds which are useful as inhibitors of retroviral proteases, particularly aspartyl proteases and more particularly HIV proteases, and which are effective in treating conditions characterized by unwanted activity of these enzymes, in particular acquired immune deficiency syndrome.

In the following description of the invention, the teaching of each of the publications mentioned is incorporated herein by reference.

A first embodiment of the invention is directed to compounds of the general formula or pharmaceutically acceptable salts or prodrugs thereof:

$$W-(A)_n-B-(A^*)_m-V \qquad (I)$$

wherein

W is selected from the group consisting of $R_1$—X—, $R_{1*}$—X*—, —Y*, —CN, —N=$CR_5R_{5}$, —C($R_5$)=$NR_3$, —C($R_5$)=$NOR_3$, —C($NR_3R_4$)=$NR_{5}$, C(D)$OR_3$, —C(D)$SR_3$ and —C(D)$NR_3R_4$, wherein Y* is as defined below, $R_1$, $R_3$ and $R_4$ are independently selected from the group consisting of $R_6$ and a solubilising group Px which is labile in vivo, wherein $R_6$ is selected from the group consisting of
hydrogen,
$R_{20}$, wherein $R_{20}$ is selected from the group consisting of
  optionally substituted ($C_1$–$C_{18}$)alkyl,
  optionally substituted ($C_2$–$C_{18}$)alkenyl,
  optionally substituted ($C_2$–$C_{18}$)alkynyl,
  optionally substituted ($C_3$–$C_{18}$)cycloalkyl,
  optionally substituted ($C_3$–$C_{18}$)cycloalkyl($C_1$–$C_{18}$) alkyl,
  optionally substituted ($C_3$–$C_{18}$)cycloalkyl($C_2$–$C_{18}$) alkenyl,
  optionally substituted ($C_3$–$C_{18}$)cycloalkyl($C_2$–$C_{18}$) alkynyl,
  optionally substituted ($C_6$–$C_{24}$)aryl,
  optionally substituted ($C_6$–$C_{24}$)aryl($C_1$–$C_{18}$)alkyl,
  optionally substituted ($C_6$–$C_{24}$)aryl($C_2$–$C_{18}$)alkenyl,
  optionally substituted ($C_6$–$C_{24}$)aryl($C_2$–$C_{18}$)alkynyl,
  optionally substituted ($C_1$–$C_{18}$)acyl,
  optionally substituted heterocyclic,
  optionally substituted heterocyclic($C_1$–$C_{18}$)alkyl,
  optionally substituted heterocyclic($C_2$–$C_{18}$)alkenyl, and
  optionally substituted heterocyclic($C_2$–$C_{18}$)alkynyl
C(D)$OR_{21}$,
C(D)$SR_{21}$,
C(D)$NR_{21}R_{22}$,
C($NR_{21}$)$R_{22}$, and
C($NR_{21}$)$OR_{22}$, and
C($NR_{2*}$)$NR_{22}R_{23}$, wherein $R_{21}$, $R_{22}$ and $R_{23}$ independently are selected from hydrogen and $R_{20}$ as previously defined, or $R_{21}$ and $R_{22}$ together, or $R_{22}$ and $R_{23}$ together form a saturated or unsaturated cyclic, bicyclic or fused ring system as defined below,
or $R_3$ and $R_4$, when present, together form a saturated or unsaturated cyclic, bicyclic or fused ring system as defined below, D is selected from O and S, X is selected from the group consisting of Y, S(O) and S(O)$_2$ wherein Y is as defined below, X* is selected from the group consisting of $NR_{10}$, O and S, wherein $R_{10}$ has the meaning of $R_6$ as previously defined, $R_{1*}$ is selected from the group consisting of $R_1$ as previously defined, P(O)(O$R_7$)$R_8$, S(O)$_2$O$R_7$ and S(O)

$_zNR_7R_8$, wherein z is 1 or 2 and $R_7$ and $R_8$ independently have the meaning of $R_{20}$ as previously defined, or $R_7$ and $R_8$ together form a saturated or unsaturated cyclic, bicyclic or fused ring system as defined below, $R_5$ and $R_{5*}$ are independently selected from the group consisting of H, $CF_3$, $C(D)OR_{103}$, $C(D)SR_{103}$ $C(D)NR_{103}R_{104}$ and $R_{20}$ as previously defined, wherein D is as previously defined, and wherein $R_{103}$ and $R_{104}$ have the meaning of $R_6$ as previously defined, or $R_{103}$ and $R_{104}$ together form a saturated or unsaturated cyclic, bicyclic or fused ring system as defined below, and $R_{5**}$ is selected from hydrogen and $R_{20}$ as previously defined ;

n is 0–6;

m is 0–6 and n+m>1;

A at each occurrence is independently selected from the group consisting of

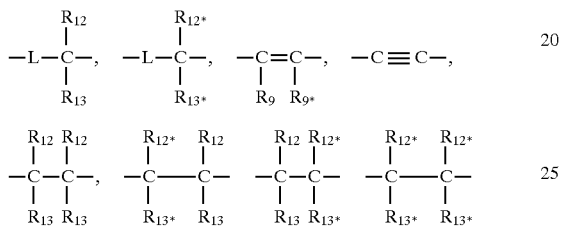

and a residue of a naturally occurring or synthetic amino acid;

A* at each occurrence is independently selected from the group consisting of

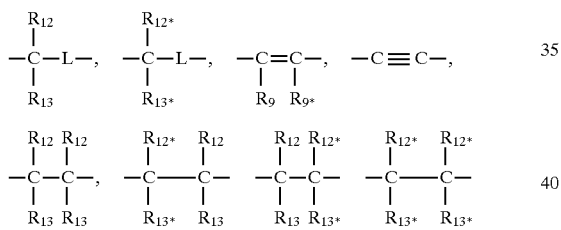

and a residue of a naturally occurring or synthetic amino acid; wherein $R_{12*}$, $R_{13*}$, $R_9$ and $R_{9*}$ are independently selected from the group consisting of F, Cl, Br, I and $R_5$ as previously defined, $R_{11}$ has the meaning of $R_1$ as previously defined, $R_{12}$ has the meaning of $R_6$ as previously defined, $R_{13}$ is selected from the group consisting of F, Cl, Br, I, $R_6$ as previously defined, and $R_{200}$, wherein $R_{200}$ is selected from the group consisting of CN,
NCO,
NCS,
OCN,
SCN,
$N_3$,
$OR_{60}$,
$SR_{60}$,
$NR_{60}R_{61}$,
$D_1C(D_2)R_{60}$,
$D_1C(D_2)D_3R_{60}$,
$D_1C(D_2)NR_{60}R_{61}$,
$NR_{60}C(D_1)R_{61}$,
$NR_{60}C(D_1)D_2R_{61}$,
$NR_{60}C(D_1)NR_{61}R_{62}$,
$NR_{60}OR_6$,
amidino,
guanidino,
$S(O)R_{60}$,
$S(O)_2D_1R_{60}$,
$S(O)NR_{60}R_{61}$,
$S(O)_2NR_{60}R_{61}$,
$D_1S(O)R_{60}$,
$D_1S(O)_2OR_{60}$,
$D_1S(O)NR_6OR_{61}$,
$D_1S(O)_2NR_{60}R_{61}$,
$P(D_1)(D_2R_{60})R_{61}$,
$P(D_1)(D_2R_{60})D_3R_{61}$,
$P(D_1) (D_2R_{60})NR_{61}R_{62}$,
$P(D_1)R_{60}R_{61}$,
$D_1P(D_2)(D_3R_{60})R_{61}$,
$D_1P(D_2)(D_3R_{60})D_4R_{61}$,
$D_1P(D_2)(D3R_{60})NR_{61}R_{62}$,
$D_1P(D_2)R_{60}R_{61}$,
$NR_{60}NR_{61}R_{62}$ and
$ONR_{60}R_{61}$, wherein $D_1$, $D_2$, $D_3$ and $D_4$ independently have the meaning of D as previously defined, and $R_{60}$, $R_{61,\ and\ R62}$ independently have the meaning of $R_6$ as previously defined or any two or more of $R_{60}$, $R_{61}$, and $R_{62}$ form part of a saturated or unsaturated cyclic, bicyclic or fused ring system as defined below, or $R_{12}$ and $R_{13}$ together are selected from the group consisting of =O, =S,

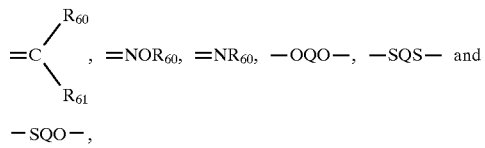

wherein Q is optionally substituted $(C_1-C_{12})$alkylidene as defined below and $R_{60}$ is as previously defined, and L is selected from the group consisting of a bond,

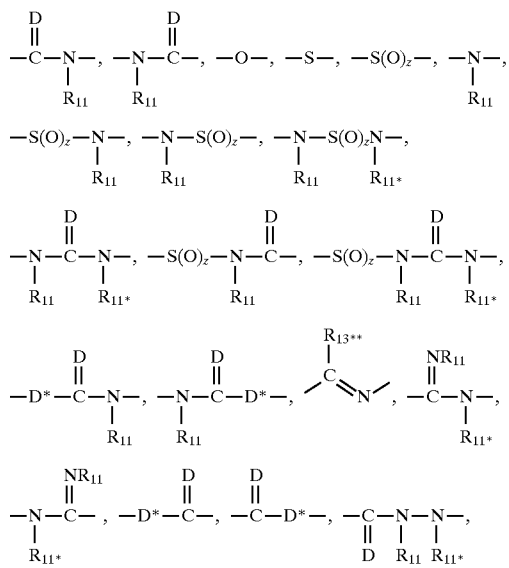

-continued

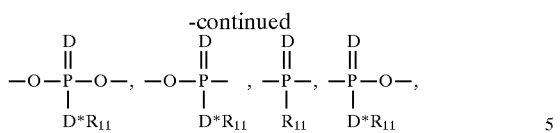

—CH₂— and —CH₂—CH₂—, wherein $R_{11}$ and D are as previously defined, $R_{11^*}$ and D* have the meaning of $R_{11}$ and D respectively, and z is 1 or 2;

$R_{13^{**}}$ is F, Cl, Br, $OR_{60}$ or $NR_{60}R_{60}$ wherein $R_{60}$ and $R_{61}$ are as previously defined, B is selected from the group consisting of

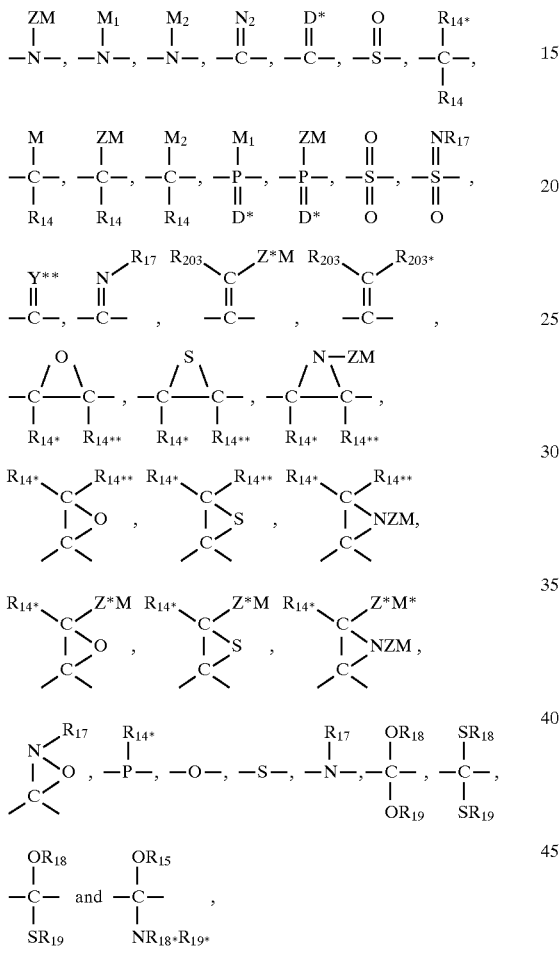

wherein $R_{203}$ and $R_{203^*}$ independently have the meaning of $R_6$ as previously defined, $R_{14^*}$ and $R_{14^{**}}$ are independently selected from the group consisting of hydrogen,
$R_{20}$ as previously defined,
$CF_3$,
$C(D^*)OR_{40}$,
$C(D^*)SR_{40}$ and
$C(D^*)NR_{40}R_{41}$, wherein $R_{40}$ and $R_{41}$, independently have the meaning of $R_{21}$ and $R_{22}$ as previously defined or $R_{40}$ and $R_{41}$ form part of a saturated or unsaturated cyclic, bicyclic or fused ring system as defined below, $R_{14}$ is selected from the group consisting of F, Cl, Br, I, $R_{14^*}$ as previously defined and $R_{200}$ as previously defined, $R_{17}$ and $R_{17^*}$ independently have the meaning of $R_6$ as previously defined, D* has the meaning of D as previously defined, Z is a saturated or unsaturated ($C_2$–$C_4$)alkylidene radical which is optionally substituted with one or more groups selected from F, Cl, Br, I and $R_{14^*}$ as previously defined, Z* is a saturated or unsaturated ($C_1$–$C_3$)alkylidene radical which is optionally substituted with one or more groups selected from F, Cl, Br, I and $R_{14^*}$ as previously defined, $M_1$ is selected from the group consisting of $OR_{15}$, $SR_{15}$ and $NR_{15}R_{17}$, wherein $R_{15}$ is selected from the group consisting of:
Px as previously defined, and
$R_6$ as previously defined, and
a glycosyl radical which is derived from a synthetic or naturally occurring aldose, ketose, deoxyaldose, deoxyketose, aminoaldose, aminoketose or an oligosaccharide thereof, and
$R_{17}$ is as previously defined, or
$R_{15}$ and $R_{17}$ together form a saturated or unsaturated cyclic, bicyclic or fused ring system as defined below, M and M* are independently selected from the group consisting of $M_1$ as previously defined, OCN, SCN, $YR_2$, Y* and $N=CR_{30}R_{31}$, wherein Y, Y* and $R_2$ are as defined below, and $R_{30}$ and $R_{31}$ independently have the meaning of $R_{20}$ as previously defined, $M_2$ is selected from the group consisting of $R_{14^*}$ as previously defined, $-CR_{30^*}=Y^{**}$ and $-CR_{30^*}=NR_{17^*}$, where $Y^{**}$ is as defined below, $R_{30^*}$ has the meaning of $R_{20}$ as previously defined, and $R_{17^*}$ is as previously defined, $R_{18}$ and $R_{19}$ independently have the meaning of $R_{20}$ as previously defined or $R_{18}$ and $R_{19}$ together form part of a saturated or unsaturated cyclic, bicyclic or fused ring system as defined below, and $R_{18^*}$ and $R_{19^*}$ together form part of a saturated or unsaturated cyclic, bicyclic or fused ring system as defined below;

V is selected from the group consisting of $YR_2$, Y* and $C(R_{30})=Y^{**}$, wherein Y is absent or is selected from the group consisting of: O.

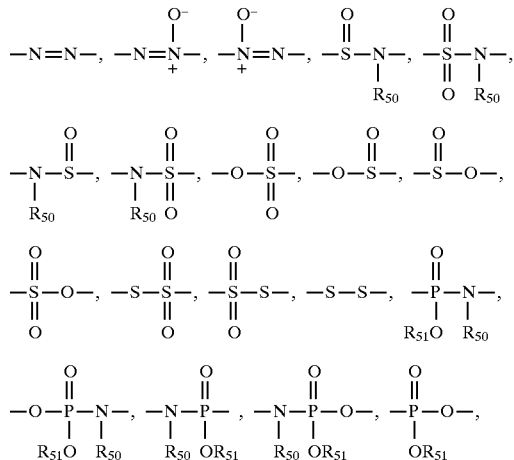

-continued

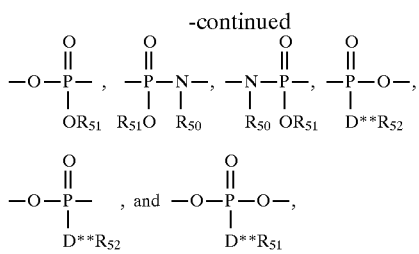

wherein D** is selected from the group consisting of a bond, O, S and NR$_{50}$, R$_{50}$ has the meaning of R$_6$ as previously defined, R$_{51}$ has the meaning of R$_{15}$ a previously defined and R$_{52}$ has the meaning of R$_{20}$ as previously defined, or R$_{50}$ and R$_{51}$, when present, together form part of a saturated or unsaturated cyclic, bicyclic or fused ring system as defined below, and R$_2$ has the meaning of R$_6$ as previously defined, Y* is selected from the group consisting of

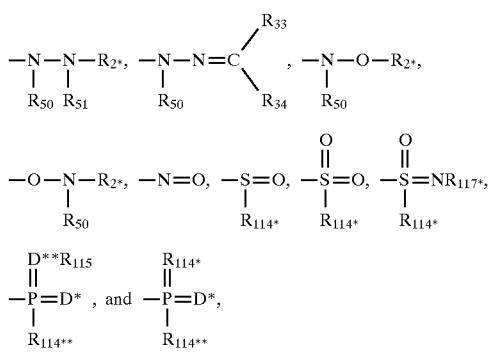

wherein D* and D** independently have the meaning of D as previously defined; R$_{114*}$, R$_{114**}$, R$_{115}$ and R$_{117*}$ have the meaning of R$_{14*}$, R$_{14**}$, R$_{15}$ and R$_{17*}$ respectively, as previously defined; R$_{50}$ and R$_{51}$ are as previously defined or R$_{50}$ and R$_{51}$ together form part of a saturated or unsaturated cyclic, bicyclic or fused ring system as defined below; R$_{2*}$ is selected from the group consisting of R$_2$ as previously defined, Px as previously defined, S(O)$_z$OR$_{120}$ and S(O)$_z$NR$_{120}$R$_{121}$, wherein z is 1 or 2; R$_{33}$ and R$_{34}$ are independently selected from the group consisting of hydrogen and R$_{20}$ as previously defined, or R$_{33}$ and R$_{34}$ together form a saturated or unsaturated cyclic, bicyclic or fused ring system as defined below, and R$_{120}$ and R$_{121}$ independently have the meaning of R$_{20}$ as previously defined, or R$_{120}$ and R$_{121}$ together form a saturated or unsaturated cyclic, bicyclic or fused ring system as defined below, R$_{30}$ is as previously defined, and Y** is selected from =N—NR$_{115}$R$_{117}$ and =N—OR$_{115}$, wherein R$_{115}$ and R$_{117}$ have the meaning of R$_{15}$ and R$_6$ respectively, as previously defined, or R$_{115}$ and R$_{117}$ together form a saturated or unsaturated cyclic, bicyclic or fused ring system as defined below, and wherein any group selected from R$_1$, R$_{1*}$, R$_2$, R$_{2*}$, R$_9$, R$_{11}$, R$_{12}$, R$_{13}$, R$_{14}$, R$_{14**}$, R$_{17}$, R$_{50}$ and R$_{51}$ may, together with any other group selected from R$_1$, R$_{1*}$, R$_2$, R$_{2*}$, R$_{9*}$, R$_{10}$, R$_{11}$, R$_{12}$, R$_{13}$, R$_{14}$, R$_{14*}$, R$_{17}$, R$_{50}$ and R$_{51}$ form one or more saturated or unsaturated cyclic, bicyclic or fused ring system(s) as defined below, and wherein any tertiary amino nitrogen atom may be replaced by the group

and, wherein any hydroxyl, mercapto or amino group may be protected by a protecting group which is labile in vivo.

Compounds of the general formula (I) are useful as inhibitors of retroviral proteases, in particular HIV proteases.

One form of the first embodiment of the invention is directed to compounds of the general formula (I') or pharmaceutically acceptable salts or prodrugs thereof:

$$W'—(A)_{n'}—B'—(A'*)_{m'}—V' \quad (I')$$

wherein

W' is selected from the group consisting of R$_1$—X—, R$_{1*}$—X*—, —Y*, —CN, —N=CR$_5$R$_{5*}$, —C(R$_5$)=NR$_3$, —C(R$_5$)=NOR$_3$, —C(D)OR$_3$, —C(D)SR$_3$ and —C(D)NR$_3$R$_4$, wherein Y* is as defined below, R$_1$, R$_3$ and R$_4$ are independently selected from the group consisting of R$_6$ and a solubilising group Px which is labile in vivo, wherein R$_6$ is selected from the group consisting of hydrogen, R$_{20}$, wherein R$_{20}$ is selected from the group consisting of optionally substituted (C$_1$–C$_{18}$)alkyl,
optionally substituted (C$_2$–C$_{18}$)alkenyl,
optionally substituted (C$_2$–C$_{18}$)alkynyl,
optionally substituted (C$_3$–C$_{18}$)cycloalkyl,
optionally substituted (C$_3$–C$_{18}$)cycloalkyl(C$_1$–C$_{18}$)alkyl,
optionally substituted (C$_3$–C$_{18}$)cycloalkyl(C$_2$–C$_{18}$)alkenyl,
optionally substituted (C$_3$–C$_{18}$)cycloalkyl(C$_2$–C$_{18}$)alkynyl,
optionally substituted (C$_6$–C$_{24}$)aryl,
optionally substituted (C$_6$–C$_{24}$)aryl(C$_1$–C$_{18}$)alkyl,
optionally substituted (C$_6$–C$_{24}$)aryl(C$_2$–C$_{18}$)alkenyl,
optionally substituted (C$_6$–C$_{24}$)aryl(C$_2$–C$_{18}$)alkynyl,
optionally substituted (C$_1$–C$_{18}$)acyl,
optionally substituted heterocyclic,
optionally substituted heterocyclic(C$_1$–C$_{18}$)alkyl,
optionally substituted heterocyclic(C$_2$–C$_{18}$)alkenyl, and
optionally substituted heterocyclic(C$_2$–C$_{18}$)alkynyl C(D)OR$_{21}$,
C(D)SR$_{21}$, and
C(D)NR$_{21}$R$_{22}$, wherein R$_2$, and R$_{22}$ independently are selected from hydrogen and R$_{20}$ as previously defined, or R$_2$, and R$_{22}$ together form a saturated or unsaturated cyclic, bicyclic or fused ring system as defined below, or R$_3$ and R$_4$, when present, together form a saturated or unsaturated cyclic, bicyclic or fused ring system as defined below, D is selected from O and S, X is selected from the group consisting of Y', S(O) and S(O)$_2$ wherein Y' is as defined below, X* is selected from the group consisting of NR$_{10}$, O and S, wherein R$_{10}$ has the meaning of R$_6$ as previously defined, $R_{1*}$ is selected from the group consisting of $R_1$ as previously defined, $S(O)_zOR_7$ and $S(O)_zNR_7R_8$, wherein z is 1 or 2 and $R_7$ and $R_8$ independently have the meaning of $R_{20}$ as previously defined, or $R_7$ and $R_8$ together form a saturated or unsaturated cyclic, bicyclic or fused ring system as defined below, $R_5$ and $R_{5*}$ are independently selected from the group consisting of H, $CF_3$, $C(D)OR_{103}$, $C(D)SR_{103}$, $C(D)NR_{103}R_{104}$ and $R_{20}$ as previously defined, wherein D is as previously defined, and wherein $R_{103}$ and $R_{104}$ have the meaning of $R_6$ as previously defined, or $R_{103}$ and $R_{104}$ together form a saturated or unsaturated cyclic, bicyclic or fused ring system as defined below;

n' is 0–8;

m' is 0–8 and n'+m'≧1;

A' and A'* are independently at each occurrence selected from the group consisting of O, S, S(O), $S(O)_2$, $NR_{11}$, $CR_{12}R_{13}$ and $CR_{12*}R_{13*}$, or two consecutive groups A'—A' or A'*—A'* are a structural unit selected from

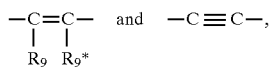

wherein and $R_{12*}$, $R_{13*}$, $R_9$ and $R_{9*}$ are independently selected from the group consisting of F, Cl, Br, I and $R_5$ as previously defined, $R_{11}$ has the meaning of $R_1$ as previosly defined, $R_{12}$ has the meaning of $R_6$ as previously defined, $R_{13}$ is selected from the group consisting of F, Cl, Br, I, $R_6$ as previously defined, and $R_{200}$, wherein $R_{200}$ is selected from the group consisting of
CN,
NCO,
NCS,
OCN,
SCN,
$N_3$,
$OR_{60}$,
$D_1C(D_2)R_{60}$,
$D_1C(D_2)D_3R_{60}$,
$D_1C(D_2)NR_{60}R_{61}$,
$NR_{60}C(D)R_{61}$,
$NR_{60}C(D_1)D_2R_{61}$,
$NR_{60}C(D_1)NR_{61}R_{62}$,
$NR_{60}OR_{61}$,
amidino,
guanidino,
$S(O)R_{60}$,
$S(O)_2D_1R_{60}$,
$S(O)NR_{60}R_{61}$,
$S(O)_2NR_{60}R_{61}$,
$D_1S(O)R_{60}$,
$D_1S(O)_2OR_{60}$,
$D_1S(O)NR_{60}R_{61}$,
$D_1S(O)_2NR_{60}R_{61}$,
$P(D_1)(D_2R_{60})R_{61}$,
$P(D_1)(D_2R_{60})D_3R_{61}$,
$P(D_1)(D_2R_{60})NR_{61}R_{62}$,
$P(D_1)R_{60}R_{61}$,
$D_1P(D_2)(D_3R_{60})R_{61}$,
$D_1P(D_2)(D_3R_{60})D_4R_{61}$,
$D_1P(D_2)(D_3R_6)NR_{61}R_{62}$,
$D_1P(D_2)R_{60}R_{61}$,
$NR_{60}NR_{61}R_{62}$ and
$ONR_{60}R_{61}$, wherein $D_1$, $D_2$, $D_3$ and $D_4$ independently have the meaning of D as previously defined, and $R_{60}$, $R_{61}$ and $R_{62}$ independently have the meaning of $R_6$ as previously defined or any two or more of $R_{60}$, $R_{61}$, and $R_{62}$ form part of a saturated or unsaturated cyclic, bicyclic or fused ring system as defined below, or $R_{12}$ and $R_{13}$ together are selected from the group consisting of =O, =S, =$NOR_{60}$, =$NR_{60}$, —OQO—, —SQS— and —SQO—, wherein Q is optionally substituted $(C_1-C_{12})$alkylidene as defined below and $R_{60}$ is as previously defined ;

B' is selected from the group consisting of

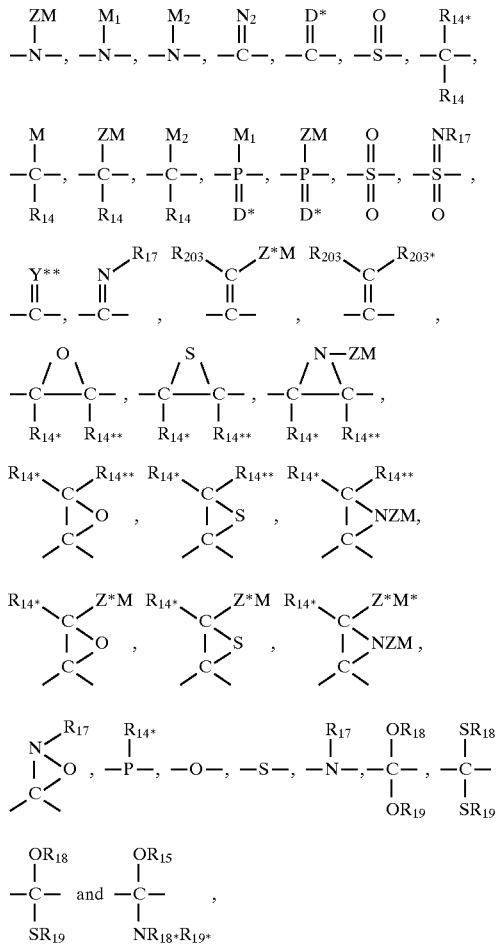

wherein $R_{203}$ and $R_{203*}$ independently have the meaning of $R_6$ as previously defined, $R_{14*}$ and $R_{14**}$ are independently selected from the group consisting of hydrogen,
$R_{20}$ as previously defined,
$CF_3$,
$C(D^*)OR_{40}$,
$C(D^*)SR_{40}$ and
$C(D^*)NR_{40}R_{41}$, wherein $R_{40}$ and $R_{41}$ independently have the meaning of $R_{21}$ and $R_{22}$ as previously defined or $R_{40}$ and $R_{41}$ form part of a saturated or unsaturated cyclic, bicyclic or fused ring system as defined below, $R_{14}$ is selected from the group consisting of F, Cl, Br, I, $R_{14*}$ as previously defined and $R_{200}$ as previously defined, $R_{17}$ and $R_{17*}$ independently have the meaning of $R_6$ as previously defined, D* has the meaning of D as previously defined, Z is a saturated or unsaturated $(C_2-C_4)$alkylidene radical which is optionally substituted with one or more groups selected from F, Cl, Br, I and $R_{14}*$ as previously defined, Z* is a saturated or unsaturated $(C_1-C_3)$alkylidene radical which is optionally substituted with one or more groups selected from F, Cl, Br, I and $R_{14}*$ as previously defined, $M_1$ is selected from the group consisting of $OR_{15}$, $SR_{15}$ and $NR_{15}R_{17}$,
  wherein $R_{15}$ is selected from the group consisting of:
    Px as previously defined,
    $R_6$ as previously defined, and
    a glycosyl radical which is derived from a synthetic or naturally occurring aldose, ketose, deoxyaldose, deoxyketose, aminoaldose, aminoketose or an oligosaccharide thereof, and
    $R_{17}$ is as previously defined, or
  $R_{15}$ and $R_{17}$ together form a saturated or unsaturated cyclic, bicyclic or fused ring system as defined below, M and M* are independently selected from the group consisting of $M_1$ as previously defined, OCN, SCN, $Y'R_2$, $Y*$ and $N=CR_{30}R_{31}$, wherein Y', Y* and $R_2$ are as defined below, and $R_{30}$ and $R_{31}$ independently have the meaning of $R_{20}$ as previously defined, $M_2$ is selected from the group consisting of $R_{14}*$ as previously defined, $-CR_{30}*=Y**$ and $-CR_{30}*=NR_{17}*$, where Y** is as defined below, $R_{30}*$ has the meaning of $R_{20}$ as previously defined, and $R_{17}*$ is as previously defined, $R_{18}$ and $R_{19}$ independently have the meaning of $R_{20}$ as previously defined or $R_{18}$ and $R_{19}$ together form part of a saturated or unsaturated cyclic, bicyclic or fused ring system as defined below, and $R_{18}*$ and $R_{19}*$ together form part of a saturated or unsaturated cyclic, bicyclic or fused ring system as defined below;

V' is selected from the group consisting of $Y'R_2$, $Y*$ and $C(R_{30})=Y**$, wherein
  Y' is selected from the group consisting of

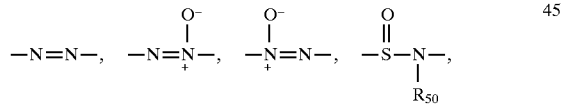
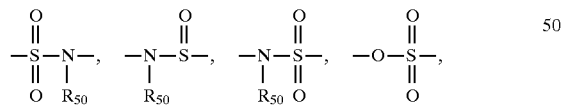
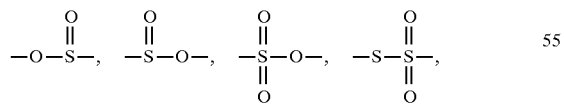
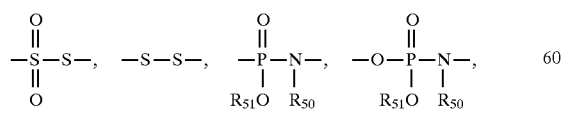
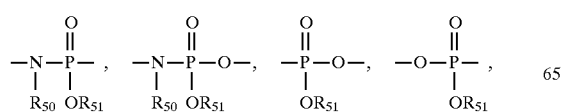
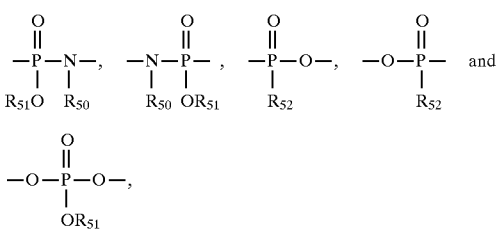

wherein $R_{50}$ has the meaning of $R_6$ as previously defined, $R_{51}$ has the meaning of $R_{15}$ as previously defined and $R_{52}$ has the meaning of $R_{20}$ as previously defined, or $R_{50}$ and $R_{51}$ together form part of a saturated or unsaturated cyclic, bicyclic or fused ring system as defined below, and $R_2$ has the meaning of $R_6$ as previously defined, Y* is selected from the group consisting of

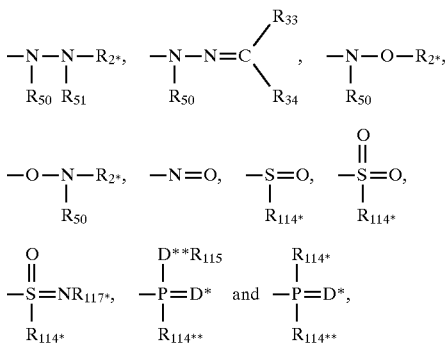

wherein D* and D** independently have the meaning of D as previously defined; $R_{114}*$, $R_{114}**$, $R_{115}$ and $R_{117}*$ have the meaning of $R_{14}*$, $R_{14}**$, $R_{15}$ and $R_{17}*$ respectively, as previously defined; $R_{50}$ and $R_{51}$ are as previously defined or $R_{50}$ and $R_{51}$ together form part of a saturated or unsaturated cyclic, bicyclic or fused ring system as defined below; $R_{2}*$ is selected from the group consisting of $R_2$ as previously defined, $S(O)_zOR_{120}$ and $S(O)_zNR_{120}R_{121}$, wherein z is 1 or 2; $R_{33}$ and $R_{34}$ are independently selected from the group consisting of hydrogen and $R_{20}$ as previously defined, or $R_{33}$ and $R_{34}$ together form a saturated or unsaturated cyclic, bicyclic or fused ring system as defined below, and $R_{120}$ and $R_{121}$ independently have the meaning of $R_{20}$ as previously defined, or $R_{120}$ and $R_{121}$ together form a saturated or unsaturated cyclic, bicyclic or fused ring system as defined below, $R_{30}$ is as previously defined, and Y** is selected from $=N-NR_{115}R_{117}$ and $=N-OR_{115}$, wherein $R_{115}$ and $R_{117}$ have the meaning of $R_{15}$ and $R_6$ respectively, as previously defined, or $R_{115}$ and $R_{117}$ together form a saturated or unsaturated cyclic, bicyclic or fused ring system as defined below, and wherein any group selected from $R_1$, $R_1*$, $R_2$, $R_2*$, $R_9$, $R_{11}$, $R_{12}$, $R_{50}$ and $R_{51}$ may, together with any other group selected from $R_1$, $R_1*$, $R_2$, $R_2*$, $R_9*$, $R_{10}$, $R_{11}$, $R_{12}$, $R_{50}$ and $R_{51}$ form one or more saturated or unsaturated cyclic, bicyclic or fused ring system(s) as defined below, and wherein any tertiary amino nitrogen atom may be replaced by the group

and, where the sequence W'—(A')$_n$'—B'—(A'*)$_m$'—V' contains a grouping of three heteroatoms together, one atom of those three heteroatoms is oxidised sulfur in the form of S(O) or S(O)$_2$, or oxidised phosphorus in the form of P(O), or the three heteroatoms comprise two nitrogen atoms which form part of a heterocycle, provided that the sequence W'—(A')$_n$'—B'—(A'*)$_m$'—V' does not contain two oxygen atoms together or three sulfur atoms together;

and wherein (a) when W' is R$_{1*}$X* wherein X* is NR$_{10}$, and V' is Y* wherein Y* is

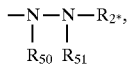

and B' is

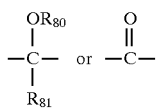

wherein R$_{81}$ is selected from the group consisting of hydrogen, —R$_{100}$H, —R$_{100}$C(O)OR$_{101}$, —R$_{100}$C(O)NR$_{101}$R$_{102}$, —R$_{100}$NR$_{102}$C(O)R$_{100*}$ and —R$_{100}$C(O)R$_{100*}$, wherein R$_{101}$ and R$_{102}$ are independently selected from the group consisting of hydrogen, optionally substituted (C$_1$–C$_{18}$)alkyl, optionally substituted (C$_3$–C$_{18}$) cycloalkyl, optionally substituted (C$_3$–C$_{18}$) cycloalkyl-(C$_1$–C$_{18}$)alkyl, optionally substituted (C$_6$–C$_{24}$)aryl, optionally substituted (C$_7$–C$_{25}$) aralkyl, optionally substituted (C$_2$–C$_{18}$)alkenyl, optionally substituted (C$_8$–C$_{26}$)-aralkenyl, optionally substituted (C$_2$–C$_{18}$)-alkynyl, optionally substituted (C$_8$–C$_{26}$)-aralkynyl and optionally substituted heterocyclic, and wherein R$_{100}$ and R$_{100*}$ are independently divalent radicals derived from a member selected from the group consisting of (C$_1$–C$_{18}$)alkyl, (C$_3$–C$_{18}$) cycloalkyl, (C$_3$–C$_{18}$)cycloalkyl(C$_1$–C$_{18}$)alkyl, (C$_6$–C$_{24}$)aryl, (C$_7$–C$_{25}$)aralkyl, (C$_2$–C$_{18}$)alkenyl, (C$_8$–C$_{26}$)aryl, (C$_7$–C$_{25}$)aralkenyl, (C$_2$–C$_{18}$)-alkynyl, (C$_8$–C$_{26}$) aralkynyl and heterocyclic, any of which may be optionally substituted as defined below, and R$_{80}$ is selected from the group consisting of R$_{81}$ as previously defined and a solubilising and/or protecting group Px which is labile in vivo, then at least one of the following applies:

(i) R$_{50}$ is a group R$_{53}$, wherein R$_{53}$ is selected from the group consisting of C(D*)OR$_{21*}$, C(D*)NR$_{21*}$R$_{22*}$, C(D*)SR$_{21*}$, C(D*)R$_{55}$, CF$_3$, R$_{55}$ and a solubilising group Px which is labile in vivo, wherein D* has the meaning of D as previously defined, R$_{21*}$ and R$_{22*}$ have the meaning of R$_{21}$ and R$_{22}$ respectively, as previously defined, and wherein R$_{55}$ is selected from the group consisting of optionally substituted (C$_1$–C$_{18}$)alkyl(C$_6$–C$_{24}$)aryl, optionally substituted (C$_2$–C$_{18}$)alkenyl(C$_6$–C$_{24}$)aryl, optionally substituted (C$_2$–C$_{18}$)-alkynyl(C$_6$–C$_{24}$) aryl, optionally substituted (C$_3$–C$_{18}$)cycloalkyl-(C$_2$–C$_{18}$)alkenyl, optionally substituted (C$_3$–C$_{18}$) cyclo-alkyl(C$_2$–C$_{18}$)alkynyl, optionally substituted (C$_3$–C$_{18}$)cycloalkyl -(C$_6$–C$_{24}$)aryl, optionally substituted acyl(C$_6$–C$_{24}$)aryl, optionally substituted heterocyclic(C$_1$–C$_{18}$)allyl, optionally substituted heterocyclic(C$_2$–C$_{18}$)alkenyl, optionally substituted heterocyclic-(C$_2$–C$_{18}$)alkynyl and optionally substituted heterocyclic(C$_2$–C$_{18}$)-(C$_6$–C$_{24}$)aryl, and n', m', R$_{1*}$, R$_{10}$, A', A'*, R$_{51}$ and R$_{2*}$ are as previously defined, (ii) one of R$_{2*}$ and R$_5$, is a group R$_{54*}$ wherein R$_{54}$ is selected from the group consisting of R$_{55*}$, C(D*) NR$_{21*}$R$_{22*}$, C(D*)OR$_{55*}$, C(D*)R$_{55*}$, C(D*)SR$_{21*}$, CF$_3$, S(O)$_z$OR$_{120}$, S(O)$_z$NR$_{120}$R$_{121}$, and a solubilising group Px which is labile in vivo, wherein z is 1 or 2 and R$_{120}$ and R$_{121}$ are as previously defined or R$_{120}$ and R$_{121}$ together form a saturated or unsaturated cyclic, bicyclic or fused ring system as defined below, and wherein R$_{21*}$ and R$_{22*}$ have the meaning of R$_{21}$ and R$_{22}$ respectively, as previously defined, and R$_{55*}$ has the meaning of R$_{55}$, as previously defined, and n', m', R$_{1*}$, R$_{10}$, A', A'*, R$_{50}$ and the other of R$_{2*}$ and R$_{51}$ are as previously defined, (iii) at least one A'or A'* is selected from the group consisting of CR$_{12}$R$_{13}$, CR$_{12}$R$_{113}$, CR$_{112}$R$_{13*}$ and CR$_{12*}$R$_{113}$, wherein R$_{112}$ and R$_{113}$ are independently selected from the group consisting of R$_{55}$ as previously defined, C(D)OR$_{21*}$, C(D)SR$_{21*}$, C(D)NR$_{21*}$R$_{22*}$, F, Cl, Br and I, wherein R$_{21*}$ and R$_{22*}$ have the meaning of R$_{21}$ and R$_{22}$ respectively, as previously defined, and D, n', m', R$_{1*}$, R$_{2*}$, R$_{10}$, R$_{11}$, R$_{12}$, R$_{12*}$, R$_{13}$, R$_{13*}$, R$_{50}$ and R$_{51}$ are as previously defined, (iv) R$_1$, is selected from the group consisting of optionally substituted (C$_2$–C$_{18}$)alkenyl, optionally substituted (C$_2$–C$_{18}$)alkynyl, optionally substituted (C$_3$–C$_{18}$) cycloalkyl(C$_2$–C$_{18}$)alkenyl, optionally substituted (C$_3$–C$_{18}$)cycloalkyl(C$_2$–C$_{18}$)alkynyl, optionally substituted (C$_6$–C$_{24}$)aryl-(C$_2$–C$_{18}$)alkenyl, optionally substituted (C$_6$–C$_{24}$)aryl(C$_2$–C$_{18}$)alkynyl, optionally substituted (C$_2$–C$_{18}$)acyl, wherein the optional substituent is other than amino, optionally substituted (C$_6$–C$_{24}$)aryl (C$_2$–C$_{18}$)acyl, optionally substituted heterocyclic (C$_1$–C$_{18}$)alkyl, optionally substituted heterocyclic (C$_2$–C$_{18}$)alkenyl, optionally substituted heterocyclic (C$_2$–C$_{18}$)alkynyl, C(O)OR$_{90}$, C(O)NR$_{91}$R$_{92}$, CF$_3$, S(O)$_z$ OR$_{120}$, S(O)$_z$NR$_{120}$R$_{121}$ and a solubilising group Px which is labile in vivo, wherein z is 1 or 2 and R$_{120}$ and R$_{121}$ are as previously defined, wherein R$_{90}$ is selected from the group consisting of (C$_3$–C$_{18}$)cycloalkyl, (C$_3$–C$_{18}$)cycloalkyl(C$_1$–C$_{18}$) alkyl, heterocyclic, (C$_1$–C$_{18}$)alkyl-heterocyclic, (C$_6$–C$_{24}$)aryl, (C$_6$–C$_{24}$)aryl(C$_1$–C$_{18}$)alkyl and (C$_6$–C$_{24}$)aryl(C$_1$–C$_{18}$)alkylheterocyclic, and wherein R$_{91}$ and R$_{92}$ are independently selected from the group consisting of optionally substituted (C$_2$–C$_{18}$) alkenyl, optionally substituted (C$_2$–C$_{18}$)alkynyl, optionally substituted (C$_3$–C$_{18}$)cycloalkyl, optionally substituted (C$_3$–C$_{18}$)cycloalkyl-(C$_1$–C$_{18}$)alkyl, optionally substituted (C$_3$–C$_{18}$)cycloalkyl-(C$_2$–C$_{18}$) alkenyl, optionally substituted (C$_3$–C$_{18}$)cycloalkyl-(C$_2$–C$_{18}$)alkynyl, optionally substituted (C$_6$–C$_{24}$) aryl-(C$_2$–C$_{18}$)alkenyl, optionally substituted (C$_6$–C$_{24}$)aryl-(C$_2$–C$_{18}$)alkynyl, optionally substituted (C$_2$–C$_{18}$)acyl, optionally substituted (C$_6$–C$_{24}$) aryl(C$_2$–C$_{18}$)acyl, optionally substituted heterocyclic, optionally substituted heterocyclic ($C_1$–$C_{18}$)alkyl, optionally substituted heterocyclic ($C_2$–$C_{18}$)alkenyl, and optionally substituted heterocyclic($C_2$–$C_{18}$)alkynyl, or $R_{91}$ and $R_{92}$ together form a saturated or unsaturated cyclic, bicyclic or fused ring system as defined below, and m', n', A', A'*, $R_2$*, $R_{50}$, $R_{51}$ and $R_{10}$ are as previously defined, (v) a group selected from $R_1$, $R_{1*}$, $R_2$, $R_{2*}$, $R_9$, $R_{11}$, $R_{12}$, $R_{50}$ and $R_{51}$, taken together with another group selected from $R_1$, $R_{1*}$, $R_2$, $R_{2*}$, $R_{9*}$, $R_{10}$, $R_{11}$, $R_{12}$, $R_{50}$ and $R_{51}$ is selected from the group consisting of —C(O)— and optionally substituted methylene;

(b) when W' is $R_{1*}$X* wherein X* is $NR_{10}$, and V' is Y* wherein Y* is

and B' is selected from —CH(OH)— and —C(O)— then at least one of the following also applies when one of the conditions (i) to (iv) defined above in (a) applies:
(vi) n'>1,
(vii) n'=0,
(viii) m'>1,
(ix) m'=0,
(x) $R_{50}$ and $R_{51}$ together form part of a saturated or unsaturated cyclic, bicyclic or fused ring system as defined below,
(xi) $R_{50}$ is a group $R_{56}$, wherein $R_{56}$ is selected from the group consisting of C(D*)O$R_{21*}$, C(D*)N$R_{21*}R_{22*}$, C(D*)S$R_{21*}$, C(D*)$R_{55}$ and a solubilising and/or protecting group Px which is labile in vivo, wherein $R_{21*}$ and $R_{22*}$ are as previously defined, and
(xii) n'=m'=1 and A'* is other than —$CH_2$—, and (c) when B' is selected from

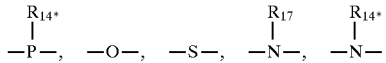

and

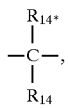

wherein $R_{14}$, $R_{14*}$ and $R_{17}$ are as previously defined, then at least one group selected from $R_2$ or $R_{2*}$, $R_{11}$, $R_{12}$, $R_{50}$ and $R_{51}$ together with another group selected from $R_1$, or $R_{1*}$, $R_{10}$, $R_{11}$ and $R_{12}$ forms a saturated or unsaturated cyclic, bicyclic or fused ring system as defined below, said ring being substituted with at least one polar group selected from =O, =S, OH, SH, $NHR_{10*}$ and C(O)OH, wherein $R_{10*}$ has the meaning of $R_{10}$ as previously defined, said polar group being sterically capable of being located within the compound of formula (I) not more than 5 ångstrom units from the P, O, S, N or C atom of group B, provided that when W' is $R_{1*}$X* and X* is NH and V' is Y* wherein Y* is

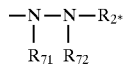

wherein $R_{1*}$ is other than H and $R_{71}$ and $R_{72}$ are independently selected from the group consisting of H, ($C_1$–$C_6$)alkyl, optionally substituted phenyl, optionally substituted naphthyl, optionally substituted phenyl($C_1$–$C_2$)alkyl and optionally substituted naphthyl-($C_1$–$C_2$)alkyl, and when (a) B' is —CH(OH)— and (A'), is —CH($R_{73}$)—wherein $R_{73}$ is selected from the group consisting of ($C_1$–$C_6$) alkyl optionally substituted with 1–5 fluorine atoms, ($C_3$–$C_6$)alkenyl, ($C_1$–$C_6$)alkoxy-$CH_2$-, $(CH_2)_p$phenyl, $(CH_2)_p$naphthyl, $(CH_2)_p$-($C_5$–$C_6$)cycloalkyl and $(CH_2)_p$indolyl, wherein said $(CH_2)_n$phenyl, $(CH_2)_n$naphthyl, $(CH_2)_n$($C_5$–$C_6$)cycloalkyl and $(CH_2)_n$indolyl are optionally substituted with nitro, halogen, ($C_1$–$C_4$) alkyl, ($C_1$–$C_4$)alkoxy or ($C_1$–$C_4$)alkylthio and wherein p is 0, 1 or 2, then (A'*)$_{m'}$ is other than

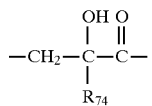

wherein $R_{74}$ has the meaning of $R_{73}$ as previously defined, and
when
(b) B' is

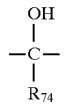

wherein $R_{74}$ has the meaning of $R_{73}$ as previously defined and (A')$_{n'}$ is

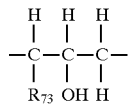

wherein $R_{73}$ is as previously defined, then (A'*)$_{m'}$ is other than —C(O)—, and when
(c) B' is —C(O)— and (A')$_{n'}$ is

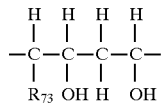

wherein $R_{73}$ is as previously defined, then m' is other than 0.

As used herein, the term "($C_1$–$C_{18}$)alkyl" includes within its meaning straight and branched chain alkyl groups having from 1 to 18 carbon atoms. Examples of such groups are methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1- or 2-pentylheptyl, tridecyl, tetradecyl, hexadecyl, octadecyl and the like.

Typically an alkyl group is $(C_a-C_b)$alkyl, in which a is selected from a value presented in the column headed "a" in Table A below at one of entries 1–17, and b has one of the values presented in the column headed "b" at that entry.

TABLE A

| Entry | a | b |
|---|---|---|
| 1 | 1 | 2, 3, 4, 5, 6, 7, 8, 9, 10, 11, 12, 13, 14, 15, 16, 17, 18 |
| 2 | 2 | 3, 4, 5, 6, 7, 8, 9, 10, 11, 12, 13, 14, 15, 16, 17, 18 |
| 3 | 3 | 4, 5, 6, 7, 8, 9, 10, 11, 12, 13, 14, 15, 16, 17, 18 |
| 4 | 4 | 5, 6, 7, 8, 9, 10, 11, 12, 13, 14, 15, 16, 17, 18 |
| 5 | 5 | 6, 7, 8, 9, 10, 11, 12, 13, 14, 15, 16, 17, 18 |
| 6 | 6 | 7, 8, 9, 10, 11, 12, 13, 14, 15, 16, 17, 18 |
| 7 | 7 | 8, 9, 10, 11, 12, 13, 14, 15, 16, 17, 18 |
| 8 | 8 | 9, 10, 11, 12, 13, 14, 15, 16, 17, 18 |
| 9 | 9 | 10, 11, 12, 13, 14, 15, 16, 17, 18 |
| 10 | 10 | 11, 12, 13, 14, 15, 16, 17, 18 |
| 11 | 11 | 12, 13, 14, 15, 16, 17, 18 |
| 12 | 12 | 13, 14, 15, 16, 17, 18 |
| 13 | 13 | 14, 15, 16, 17, 18 |
| 14 | 14 | 15, 16, 17, 18 |
| 15 | 15 | 16, 17, 18 |
| 16 | 16 | 17, 18 |
| 17 | 17 | 18 |

As used herein, the term "$(C_2-C_{18})$alkenyl" includes within its meaning ethylenically mono-, di- or poly-unsaturated alkyl groups having from 2 to 18 carbon atoms, and may be straight-chain or branched. Examples of such alkenyl groups are vinyl allyl, 1-methylvinyl, 1-propenyl, 1-butenyl, 2-butenyl, 3-butenyl, 1,3-butadienyl, 2-methyl-1-propenyl, 2-methyl-2-propenyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 3-heptenyl, 1-octenyl, 1,3-octadienyl, 1-nonenyl, 2-nonenyl, 3-nonenyl, 1-decenyl, 3-decenyl, 1-undecenyl, oleyl, linoleyl and linolenyl.

Typically an alkenyl group is $(C_a-C_b)$alkenyl, in which a is selected from a value presented in the column headed "a" in Table A above at one of entries 2–17, and b has one of the values presented in the column headed "b" at that entry.

As used herein, the term "$(C_2-C_{18})$alkynyl" includes within its meaning mono-, di- and poly-acetylenically unsaturated alkyl groups having from 2 to 18 carbon atoms, and may be straight-chain or branched. Examples of such alkynyl groups are ethynyl, propynyl, n-butynyl, n-pentynyl, 3-methyl-1-butynyl, n-hexynyl, methyl-pentynyl and $(C_7-C_{12})$alkynyl.

Typically an alkynyl group is $(C_a-C_b)$alkynyl, in which a is selected from a value presented in the column headed "a" in Table A above at one of entries 2–17, and b has one of the values presented in the column headed "b" at that entry.

As used herein, the term "$(C_3-C_{18})$cycloalkyl" refers to otionally unsaturated mono-, di- or polycyclic alkyl groups having from 3 to 18 carbon atoms. Examples of such groups include cyclopropyl, cyclobutyl, cyclopentyl, cyclopentenyl, cyclopentadienyl, cyclohexyl, cyclohexenyl, cyclohexadienyl, cycloheptyl, cycloheptenyl, cycloheptadienyl, cycloheptatrienyl, cyclooctyl, cyclooctenyl, cyclooctadienyl, cyclooctatrienyl, cyclooctatetraenyl, cyclononyl, cyclodecyl, cycloundecyl, cyclododecyl, $(C_9-C_{12})$cycloalkynyl, bicyclo[2.2.1] heptanyl, bicyclo[2.2.1]heptenyl, bicyclo[2.2.1]-heptadienyl, bicyclo[2.2.2]octanyl, bicyclo[2.2.2]octenyl, bicyclo[3.3.1]nonyl, bicyclo-[3.1.0.]hexyl, bicyclo[4.1.0] heptyl, bicyclo[3.2.1.]octyl, bicyclo[3 .3.0]octyl, bicyclo-[3.3.0]octenyl, bicyclo[3.3.1]nonyl, bicyclo[4.4.0]decyl, adamantyl, tricyclo[5.2.1.0$^{2,6}$]decyl and the like.

Typically a cycloalkyl group is $(C_a-C_b)$cycloalkyl, in which a is selected from a value presented in the column headed "a" in Table A above at one of entries 3–17, and b has one of the values presented in the column headed "b" at that entry.

As used herein, the term "$(C_3-C_{18})$cycloalkyl$(C_1-C_{18})$ allyl" refers to a $(C_1-C_{18})$alkyl group as defined above, substituted with a $(C_3-C_{18})$cycloalkyl group as defined above. Examples of cycloalkylalkyl groups include cycloalkyl-loweralkyl groups, such as cycloalkylmethyl, cycloalkylethyl, cycloalkylpropyl, cycloalkylbutyl, cycloalkylisopropyl, cycloalkylisobutyl, cycloalkylpentyl and cycloalkylhexyl, wherein the cycloalkyl is as exemplified in the preceding paragraph.

As used herein, the term "$(C_3-C_{18})$cycloalkyl$(C_2-C_{18})$ alkenyl" refers to a $(C_2-C_{18})$alkenyl group as defined above, substituted with a $(C_3-C_{18})$cycloalkyl group as defined above. Examples of cycloalkylalkenyl groups include cycloalkyl-loweralkenyl groups, such as cycloalkylethenyl, cycloalkylpropenyl, cycloalkylbutenyl, cycloalkylisobutenyl, cycloalkylpentenyl and cycloalkylhexenyl, wherein the cycloalkyl is as exemplified above under "$(C_3-C_{18})$cycloalkyl".

As used herein, the term "$(C_3-C_{18})$cycloalkyl$(C_2-C_{18})$ alkynyl" refers to a $(C_2-C_{18})$alkynyl group as defined above, substituted with a $(C_3-C_{18})$cycloalkyl group as defined above. Examples of cycloalkylalkynyl groups include cycloalkyl-loweralkynyl groups, such as cycloalkylethynyl, cycloalkylpropynyl, cycloalkylbutynyl, cycloalkylpentynyl and cycloalkylhexynyl, wherein the cycloalkyl is as exemplified above under "$(C_3-C_{18})$cycloalkyl".

As used herein, the term "$(C_6-C_{24})$aryl" refers to single, polynuclear, conjugated and fused residues of aromatic hydrocarbons having from 6 to 24 carbon atoms. Examples of such groups are phenyl, biphenyl, terphenyl, quaterphenyl, naphthyl, tetrahydronaphthyl, acenaphthyl, anthracenyl, dihydroanthracenyl, benzanthracenyl, dibenzanthracenyl, phenanthrenyl, fluorenyl, pyrenyl, indenyl, indanyl, azulenyl, chrysenyl and the like. In all cases, any available position of the fused or conjugated bicyclic system can be used for attachment to the remainder of the molecule of formula (I).

Typically an aryl group is $(C_a-C_b)$aryl, in which a is selected from a value presented in the column headed "a" in Table B below at one of entries 1–18, and b has one of the values presented in the column headed "b" at that entry.

TABLE B

| Entry | a | b |
|---|---|---|
| 1 | 6 | 10, 12, 13, 14, 15, 16, 17, 18, 19, 20, 21, 22, 23, 24 |
| 2 | 10 | 12, 13, 14, 15, 16, 17, 18, 19, 20, 21, 22, 23, 24 |
| 3 | 12 | 13, 14, 15, 16, 17, 18, 19, 20, 21, 22, 23, 24 |
| 8 | 13 | 14, 15, 16, 17, 18, 19, 20, 21, 22, 23, 24 |
| 9 | 14 | 15, 16, 17, 18, 19, 20, 21, 22, 23, 24 |
| 10 | 15 | 16, 17, 18, 19, 20, 21, 22, 23, 24 |
| 11 | 16 | 17, 18, 19, 20, 21, 22, 23, 24 |
| 12 | 17 | 18, 19, 20, 21, 22, 23, 24 |
| 13 | 18 | 19, 20, 21, 22, 23, 24 |
| 14 | 19 | 20, 21, 22, 23, 24 |
| 15 | 20 | 21, 22, 23, 24 |
| 16 | 21 | 22, 23, 24 |
| 17 | 22 | 23, 24 |
| 18 | 23 | 24 |

As used herein, the term "$(C_6-C_{24})$aryl$(C_1-C_{18})$alkyl" refers to a $(C_1-C_{18})$alkyl substituted with one or more $(C_6-C_{24})$aryl groups as previously defined. Examples of such groups are aryl-loweralkyl groups such as arylmethyl, arylethyl, arylisopropyl, arylpropyl, arylbutyl, arylisobutyl, arylpentyl and arylhexyl, wherein the aryl is as exemplified in the preceding paragraph, such as benzyl, diphenylmethyl, 2-phenylethyl, 1-phenylethyl, naphthylmethyl, 3-phenylpropyl, triphenylmethyl, 1,3-diphenylpropyl, 2- or 3-β-naphthylpropyl, 2-benzyl-propyl and the like.

As used herein, the term "$(C_7-C_{25})$aralkyl" refers to an alkyl group substituted with an aryl group, wherein the total number of carbon atoms in the aryl-substituted alkyl group is from 7 to 25. Optional substituents for $(C_7-C_{25})$aralkyl are as defined below with respect to $(C_6-C_{24})$aryl$(C_1-C_{18})$alkyl.

As used herein, the term "$(C_6-C_{24})$aryl$(C_1-C_{18})$alkenyl" refers to a alkenyl group substituted with one or more $(C_6-C_{24})$aryl groups as previously defined. Examples of such groups are aryl-loweralkenyl groups such as arylethenyl, arylpropenyl, arylbutenyl, arylisobutenyl, arylpentenyl and arylhexenyl, wherein the aryl is as exemplified above under "$(C_6-C_{24})$aryl" such as styryl, cinnamyl, 2-naphthylethenyl, 1phenyl-2-methyl-1-propenyl, 2-phenyl-2-butenyl and the like.

As used herein, the term "$(C_8-C_{26})$aralkenyl" refers to an alkenyl group substituted with an aryl group, wherein the total number of carbon atoms in the aryl-substituted alkenyl group is from 8 to 26. Optional substituents for $(C_8-C_{26})$ aralkenyl are as defined below with respect to $(C_6-C_{24})$aryl $(C_2-C_{18})$alkenyl.

As used herein, the term "$(C_6-C_{24})$aryl$(C_1-C_{18})$alkynyl" refers to a alkynyl group substituted with one or more $(C_6-C_{24})$aryl groups as previously defined. Examples of such groups are aryl-loweralkenyl groups such as arylethenyl, arylpropenyl, arylbutenyl, arylisobutenyl, arylpentenyl and arylhexenyl, wherein the aryl is as exemplified above under "$(C_6-C_{24})$aryl" such as phenylethynyl and the like.

As used herein, the term "$(C_8-C_{26})$aralkynyl" refers to an alkynyl group substituted with an aryl group, wherein the total number of carbon atoms in the aryl-substituted alkynyl group is from 8 to 26. Optional substituents for $(C_8-C_{26})$ aralkynyl are as defined below with respect to $(C_6-C_{24})$aryl $(C_2-C_{18})$alkynyl.

As used herein, the term "$(C_1-C_{18})$acyl" refers to a group $R_{300}C(O)$— or $R_{300}C(S)$—, wherein $R_{300}$ is selected from the group consisting of hydrogen, $(C_1-C_{18})$alkyl, $(C_2-C_{18})$ alkenyl, $(C_2-C_{18})$alkynyl, $(C_3-C_{18})$cycloalkyl $(C_3-C_{18})$ cycloalkyl-$(C_1-C_{18})$alkyl, $(C_3-C_{18})$cycloalkyl$(C_2-C_{18})$ alkenyl, $(C_3-C_{18})$cycloalkyl$(C_2-C_{18})$alkynyl, $(C_6-C_{24})$aryl, $(C_6-C_{24})$aryl$(C_1-C_{18})$alkyl, $(C_6-C_{24})$aryl$(C_2-C_{18})$alkenyl, $(C_6-C_{24})$aryl-$(C_2-C_{18})$alkynyl, heterocyclic, heterocyclic $(C_1-C_{18})$alkyl, heterocyclic$(C_2-C_{18})$alkenyl, and heterocyclic$(C_2-C_{18})$alkynyl.

Typically an acyl group is $(C_a-C_b)$acyl, in which a is selected from a value presented in the column headed "a" in Table A above at one of entries 1–17, and b has one of the values presented in the column headed "b" at that entry.

Examples of acyl groups include loweralkylcarbonyl such as formyl, acetyl, propionyl, butyryl; loweralkenylcarbonyl such as pivaloyl, acryloyl, vinylacetyl, crotonoyl, 3-pentenoyl, 4-pentenoyl; and loweralkynylcarbonyl such as propioloyl, 2-butynoyl and 3-butynoyl, any of which may be substituted with cycloalkyl, aryl or heterocyclic as exemplified herein, as, for example, cyclopropylcarbonyl, cyclobutylcarbonyl, cyclopentylcarbonyl, 1-cyclopentenylcarbonyl, cyclopentylacetyl, 1-cyclohexenylcarbonyl, 1,4-cyclohexadienylcarbonyl, cyclohexylacetyl, cyclohexenylacetyl, 1,4cyclohexadienylacetyl, bicyclo[2.2.1]hept-2-ylcarbonyl, bicyclo-[2.2.1]heptylacetyl, bicyclo[2.2.1]hepten-2-ylcarbonyl, bicyclo[2.2.2]oct-2-ylcarbonyl, bicyclo[2.2.2] octylacetyl, bicyclo[2.2.2]octyl-3-propionyl, bicyclo[2.2.2] octen-2-yl-carbonyl, bicyclo[3.3.1]non-9-ylcarbonyl, bicyclo[3.3.1]non-9-ylacetyl, bicyclononyl-3-propionyl, bicyclo[4.4.0]dec-2-ylcarbonyl, bicyclo[4.4.0]dec-2-ylacetyl, 1-adamantylcarbonyl, 2-adamantylcarbonyl, 1-adamantylacetyl, 2-adamantylacetyl, tricyclo[5.2.1.0$^{2,6}$] dec-8-ylacetyl, benzoyl, phenylacetyl, diphenylacetyl, triphenylacetyl, 3-phenylpropionyl, dibenzylacetyl, α-naphthoyl, β-naphthoyl, α-naphthylacetyl, β-naphthylacetyl, indenylcarbonyl, indanylcarbonyl, phenanthrenylcarbonyl, 9-fluorenylcarbonyl, pyrrolylcarbonyl, pyrrolylacetyl, furylcarbonyl, furylacetyl, thienylcarbonyl, thienylacetyl, pyrazinylcarbonyl, pyrazinylacetyl, pyrrolidinylcarbonyl, pyrrolidinylacetyl, pyridylcarbonyl, pyridylacetyl, pyrimidinylcarbonyl, pyrimidinylacetyl, piperidylcarbonyl, piperidylacetyl, piperazinylcarbonyl, piperazinylacetyl, morpholinylcarbonyl, morpholinylacetyl, thiomorpholinylcarbonyl, thiomorpholinylacetyl, indolylcarbonyl, indolylacetyl, quinolylcarbonyl, quinolylacetyl, isoquinolylcarbonyl, isoquinolylacetyl, quinoxalinylcarbonyl, benzofuranylcarbonyl, benzofuranylacetyl, indolinylcarbonyl, indolinylacetyl, 1,2, 3,4-tetrahydroquinolylcarbonyl, 1,2,3,4-tetrahydroquinolylacetyl, 1,2,3,4-tetrahydroisoquinolylcarbonyl, 1,2,3,4-tetrahydroisoquinolylacetyl, cyclohexylacryloyl, cinnamoyl, styrylacetyl and phenylpropioloyl.

As used herein, the term "heterocyclic" refers to any saturated or unsaturated 3- to 16-membered monocyclic, bicyclic or polycyclic ring containing one or more heteroatom independently selected from oxygen, nitrogen and sulphur. The term "heterocyclic" includes any group in which a heterocyclic ring is fused to one or more benzene, naphthalene or cycloalkane rings. Sulfur-containing heterocyclics may be substituted at sulfur with one or two oxygen atoms. Examples of heterocyclics are pyridyl, thienyl, furyl, pyrrolyl, indolyl, pyridazinyl, perhydropyridazinyl, pyrazolyl, pyrazoldinyl, 2,3,5,6-tetrahydropyrazinyl, phthalazinyl, 1,2,3,4-tetrahydrophthalazinyl, perhydrophthalazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl, piperidyl, tetrahydrofuryl, imidazolyl, oxazolyl, thiazolidino, oxazolidinyl, isoxazolyl, isothiazolyl, isoxazolidinyl, imidazolidinyl, morpholinyl, pyrrolidinyl, pyrazolinyl, benzothienyl, benzisoxazolyl, benzoisothiazolyl, benzothiadiazolyl, tetrazolyl, triazolyl, thiadiazolyl, benzimidazolyl, pyrrolinyl, quinuclidinyl, 1,4-thioxanyl, 1,3-thioxanyl, azanorbornyl, isoquinuclidinyl, pyranyl, furazanyl, azepinyl, 1H-indazolyl, 2,3-dihydro-1H-indazolyl, quinoxalinyl, cinnolyl, 1,2,3,4-tetrahydrocinnolinyl, pteridinyl, naphthyridinyl, 4H-quinolizinyl, benz[e]indolyl, benzoxazinyl, benzoxadiazolyl, benzothiazinyl, benzotriazolyl, carbazolyl, β-carbolinyl, 1,2,3,4,5,6-hexahydro-β-carbolinyl, phenanthridyl, phenoxazinyl, phenothiazinyl, 1-azaacenaphthenyl, thiatriazolyl, oxadiazolyl, thiadiazolyl, chromanyl, thiachromanyl, isochromanyl, chromenyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, 2-imidazolinyl, 2,3-dihydropyridyl, piperazinyl, thiomorpholinyl, S,S-dioxo-thiomorpholinyl, indolinyl, S,S-dioxo-1,2,3-benzothiadiazolyl, S,S-dioxo-1,2-thioxanyl, S,S-dioxo-1,4-thioxanyl, isoindolinyl, 4,5,6,7-tetrahydroindolyl, 1,2,3,4-tetra-hydroquinolyl, 1,2,3,4-tetrahydroisoquinolyl, hexahydroquinolyl, hexahydroisoquinolyl, 1,2,3,4-tetrahydro-3,1-benzodiazinyl, 3,4-dihydro-3H4,1-benzoxazinyl, 3,4-dihydro-3H-4,1-benzothiazinyl, 2,3,4,5-tetrahydro-1H-5,1-benzazepinyl and 5,6-dihydro-phenanthridinyl and the like.

Configurations which result in unstable heterocyclics are not included within the scope of the definition of "heterocyclic" or "saturated or unsaturated cyclic, bicyclic or fused ring system".

As used herein, the term "heterocyclic($C_1$–$C_{18}$)alkyl" refers to a ($C_1$–$C_{18}$)alkyl group as previously defined, which is substituted with a heterocyclic group as previously defied. Examples of such groups are heterocyclic-loweralkyl groups such as heterocyclicmethyl, heterocyclicethyl, heterocyclicisopropyl, heterocyclicpropyl, heterocyclicbutyl, heterocyclicisobutyl, heterocyclicpentyl and heterocyclichexyl, wherein the heterocyclic is as exemplified in the preceding paragraph.

As used herein, the term "heterocyclic($C_1$–$C_{18}$)alkenyl" refers to a ($C_1$–$C_{18}$)alkenyl group as previously defined, which is substituted with a heterocyclic group as previously defined. Examples of such groups are heterocyclic-loweralkenyl groups such as heterocyclicethenyl, heterocyclicpropenyl, heterocyclicbutenyl, heterocyclicisobutenyl, heterocyclicpentenyl and heterocyclichexenyl, wherein the heterocyclic is as exemplified above under "heterocyclic".

As used herein, the term "heterocyclic($C_1$–$C_{18}$)alkynyl" refers to a ($C_1$–$C_{18}$)alkynyl group as previously defined, which is substituted with a heterocyclic group as previously defined.

As used herein, the term "alkylidene" refers to divalent radicals derived from alkyl groups. Examples of such radicals are —$CH_2$—, —$CH_2CH_2$—, —CH=CH—, —$CH_2CH_2CH_2$—, —C(=$CH_2$)$CH_2$—, —$CH_2$CH =CH—, —($CH_2$)$_4$—, —$CH_2CH_2$CH =CH—, —$CH_2$CH=$CHCH_2$— and —($CH_2$)r— where r is 5–12. The term also refers to such radicals in which one or more of the bonds of the radical from part of a cyclic system, and to such radicals wherein one or more carbon atoms is replaced by O, S or NH. Examples of such radicals are groups of the structure

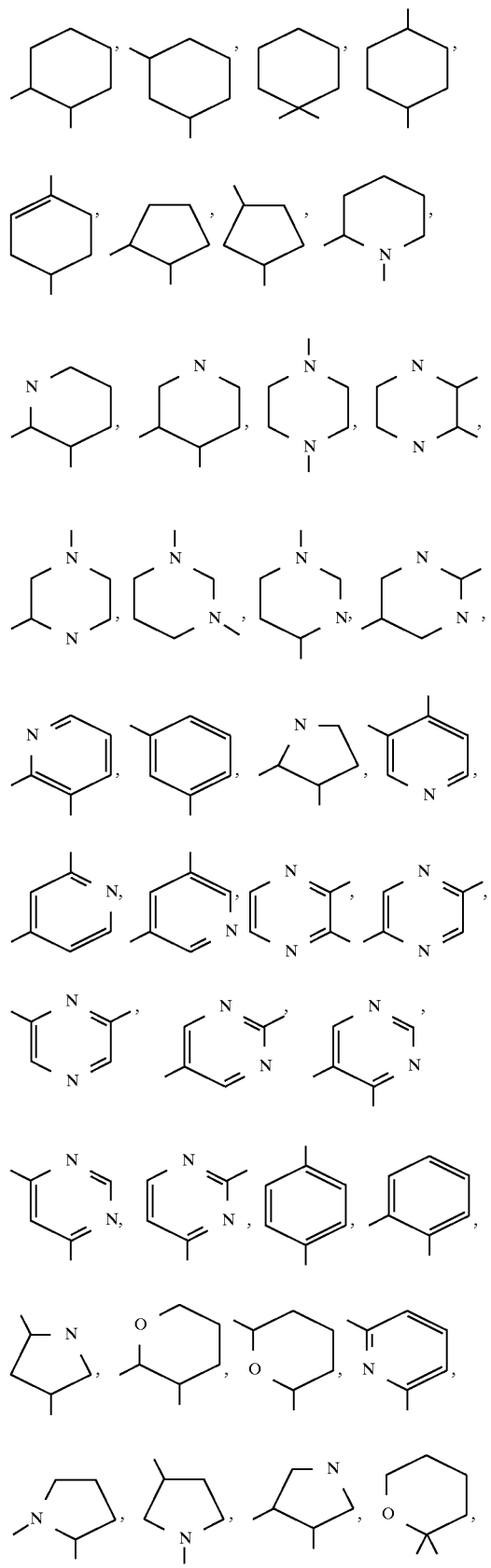

-continued

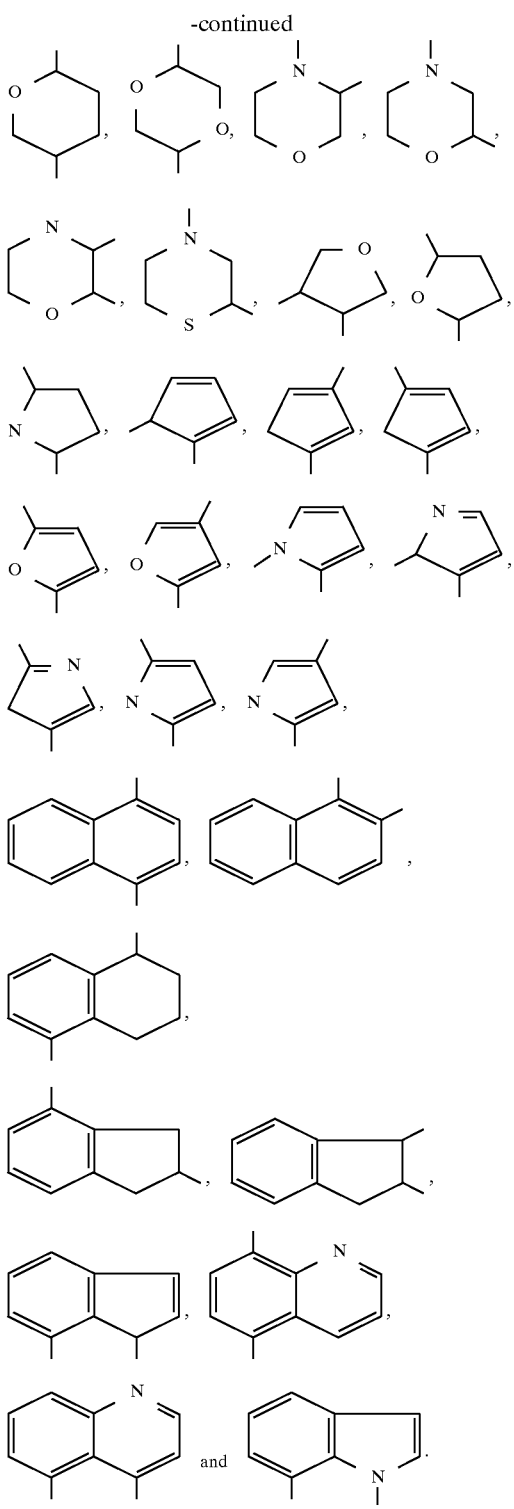

and similar groups, including those shown above wherein any N or O atom is replaced by S.

As used herein the term "saturated or unsaturated cyclic, bicyclic or fused ring system" refers to a stable cyclic system of up to 16 carbon atoms, wherein said ring system may contain: for 3- and 4-membered rings, one heteroatom; for 5-membered rings, one or two heteroatoms; for 6- and 7-membered rings, one to three heteroatoms; for 8- and 9-membered rings, from one to four heteroatoms; for 10- and 11-membered rings, from one to five heteroatoms; for 12- and 13-membered rings, from one to six heteroatoms; for 14- and 15-membered rings, from one to seven heteroatoms; and for 16-membered rings, from one to eight heteroatoms; the heteroatom(s) being independently selected from oxygen, nitrogen and sulphur; which ring system may be substituted with one or more substituents independently selected from: $R_{150}$ and a group T, where $R_{150}$ has the meaning of $R_{20}$ as previously defined, and where T is selected from the group consisting of —F, —Cl, —Br, —I, —CF$_3$, —CN, —NCO, —NCS, —OCN, —SCN, —N$_3$, —OR', —NR''', —NR'C(O)R'', —NR'C(O)OR'', —NR'C(O)NR''R'', —NO$_2$, —SR', —S(O)R', —S(O)$_2$R', —S(O)OR', —S(O)$_2$OR', —S(O)NR'R'', —S(O)$_2$NR'R'', =O, =S, =N$_2$, =NOH, =NOR', —NR''OR', —CHO, —OC(O)R', —OC(O)OR', —OC(O)NR'R'', —C(O)R', —C(O)OR', —C(O)NR'R'', —OC(S)R', —OC(S)OR', —OC(S)NR'R'', —C(S)R', —C(S)OR', —C(S)NR'R'', —SC(O)R', —SC(O)OR', —SC(O)NR'R'', —C(O)SR', —SC(S)R', —SC(S)OR', —SC(S)NR'R'', —C(S)SR', —C(=NR')OR'', —C(=NR')SR'', —C(=NR')NR''R''', —OS(O)R', —OS(O)$_2$R', —OS(O)OR', —OS(O)$_2$OR', —OS(O)NR'R'', —OS(O)$_2$NR'R'', NR'S(O)2NR''R''', —NR'S(O)$_2$R'', —NHC(=NH)NR', —C(=NH)NR', —P(O)(OR')R'', —P(O)(SR')R'', —P(O)(OR')OR'', —P(O)(OR')NR''R''', —P(O)R'R'', —OP(O)(OR')R'', —OP(O)(OR')OR'', —OP(O)(SR')OR'', —OP(O)(OR')NR''R''', —OP(O)R'R'', and —B(OR')(OR''), wherein R', R'' and R''' are independently selected from the group consisting of hydrogen, (C$_1$–C$_{18}$)alkyl, typically (C$_1$–C$_{12}$) alkyl; (C$_3$–C$_{18}$)cycloalkyl, typically (C$_3$–C$_{12}$)cycloalkyl; (C$_3$–C$_{18}$)cycloalkyl(C$_1$–C$_{18}$)alkyl, typically (C$_3$–C$_{12}$) cycloalkyl(C$_1$–C$_6$)alkyl; (C$_6$–C$_{24}$)aryl, typically (C$_6$–C$_6$) aryl; (C$_6$–C$_{24}$)aryl(C$_1$–C$_{18}$)alkyl, typically (C$_6$–C$_{10}$)aryl (C$_1$–C$_6$)alkyl; (C$_2$–C$_{18}$)alkenyl, typically (C$_2$–C$_{12}$)alkenyl; (C$_6$–C$_{24}$)-aryl(C$_2$–C$_{18}$)alkenyl, typically (C$_6$–C$_{10}$)aryl (C$_2$–C$_6$)alkenyl; (C$_2$–C$_{18}$)alkynyl, typically (C$_2$–C$_{12}$) alkynyl; (C$_6$–C$_{24}$)aryl(C$_2$–C$_{18}$)aralkynyl, typically (C$_6$–C$_{10}$) aryl(C$_1$–C$_6$)alkynyl, heterocyclic, heterocyclic(C$_1$–C$_{18}$) alkyl, typically heterocyclic(C$_1$–C$_{12}$)alkyl, heterocyclic-(C$_2$–C$_{18}$)alkenyl, typically heterocyclic(C$_2$–C$_{12}$)alkenyl and heterocyclic(C$_2$–C$_{18}$)alkynyl, typically heterocyclic (C$_2$–C$_{12}$)alkynyl, and wherein R', R'' and R''' may be optionally substituted with up to six groups independently selected from hydroxy, (C$_1$–C$_6$)alkoxy, (C$_1$–C$_6$)aryloxy, (C$_1$–C$_6$) thioalkoxy, (C$_1$–C$_6$)thioaryloxy, (C$_1$–C$_6$)alkoxy(C$_1$–C$_6$) alkoxy, amino, (C$_1$–C$_6$)alkylamino, di(C$_1$–C$_6$)alkylamino, fluoro, chloro, bromo, iodo, carboxy, (C$_1$–C$_6$) alkoxycarbonyl, (C$_1$–C$_6$)alkylaminocarbonyl and di(C$_1$–C$_6$) alkylaminocarbonyl. Examples of saturated or unsaturated cyclic, bicyclic or fused ring systems are the heterocyclic and cyclic alkylidene groups exemplified above.

As used herein, the term "optionally substituted (C$_1$–C$_{18}$) alkyl" refers to a (C$_1$–C$_{18}$)alkyl group as defined above wherein one or more hydrogen atoms are replaced by one or more substitutents T as previously defined.

Examples of substituted (C$_1$–C$_{18}$)alkyl groups include hydroxy-loweralkyl such as hydroxymethyl, hydroxyethyl and 3-hydroxypropyl; loweralkoxy-loweralkyl such as methoxymethyl, 2-methoxyethyl, 2,2-dimethoxyethyl and 3-methoxypropyl; aryloxy-loweralkyl such as phenoxymethyl, phenoxyethyl, α-naphthyloxymethyl and β-naphthyloxyethyl; arylloweralkoxy-loweralkyl such as benzyloxymethyl, benzyloxyethyl and 3-benzyloxypropyl; halo-loweralkyl such as chloromethyl, trifluoromethyl, 2-fluoro-, 2-chloro-, 2-bromo- or 2-iodo-ethyl, 2,2,2-trifluoro-ethyl, 2,2,2-trichloro-ethyl, 3-chloropropyl and 3-bromopropyl; amino-loweralkyl such as aminomethyl, 2-aminoethyl, 3-aminopropyl, 5-aminopentyl, dimethylaminomethyl, 2-dimethylaminoethyl and 3-phenylaminopropyl; carboxy-loweralkyl such as carboxymethyl, carboxyethyl and 3-carboxypropyl; acylloweralkyl such as acylmethyl, acylethyl, acylpropyl, acylisopropyl, acylbutyl, acylisobutyl, acylpentyl and acylhexyl wherein the acyl is as exemplified above under "($C_1$–$C_{18}$)acyl"; acyloxy-loweralkyl such as acetoxymethyl, acetoxyethyl, 2-acetoxypropyl, 3-acetoxypropyl, propionyloxyethyl and 3-propionyloxypropyl; loweralkylcarbonylamino-loweralkyl such as acetylaminomethyl, acetylaminoethyl, 2-acetylaminopropyl, propionylaminomethyl and propionylaminoethyl; loweralkylaminocarbonylamino-loweralkyl, such as dimethylaminocarbonylaminoethyl; sulfonyl-loweralkyl such as methylsulfonyl-methyl, ethylsulfonyl-methyl, tert-butylsulfonyl-methyl, phenylsulfonylmethyl, phenylsulfonylethyl, 4-toluenesulfonylethyl and 4-toluenesulfonylmethyl; cyano-loweralkyl such as cyanomethyl, 2-cyanoethyl, 2-cyanopropyl, 3-cyanopropyl, 2-cyanobutyl, 3-cyanobutyl and 4-cyanobutyl; oxo-loweralkyl such as 2-oxo-propyl, 2-oxo-butyl, 3-oxo-butyl, 2-, 3- or 4-oxo-pentyl and 2,4-dioxo-pentyl; and lower-alkyl groups substituted with two or more than different substitutents as exemplified above.

As used herein, the term "optionally substituted ($C_1$–$C_{18}$) alkenyl" refers to a ($C_1$–$C_{18}$)alkenyl group as defined above wherein one or more hydrogen atoms are replaced by a substituent or substitutents T as previously defined.

As used herein, the term "optionally substituted ($C_1$–$C_{18}$) alkynyl" refers to a ($C_1$–$C_{18}$)alkynyl group as defined above wherein one or more hydrogen atoms are replaced by a substituent or substitutents T as previously defined.

As used herein, the term "optionally substituted ($C_3$–$C_{24}$) cycloalkyl" refers to a ($C_3$–$C_{24}$)cycloalkyl group as defined above wherein one or more hydrogen atoms are replaced by a substituent or substitutents independently selected from $R^{IV}$ and T as previously defined, wherein $R^{IV}$ is selected from ($C_1$–$C_{18}$)alkyl, ($C_2$–$C_{18}$)alkenyl, ($C_2$–$C_{18}$)alkynyl, ($C_3$–$C_{18}$)cycloalkyl, ($C_3$–$C_{18}$)cycloalkyl($C_1$–$C_{18}$)alkyl, ($C_3$–$C_{18}$)cycloalkyl($C_2$–$C_{18}$)alkenyl, ($C_3$–$C_{18}$)cycloalkyl ($C_2$–$C_{18}$)alkynyl, ($C_2$–$C_{18}$)acyl, ($C_6$–$C_{24}$)aryl($C_2$–$C_{18}$)acyl, heterocyclic, heterocyclic($C_1$–$C_{18}$)alkyl, ($C_2$–$C_{18}$)alkenyl, and heterocyclic($C_2$–$C_{18}$)alkynyl, and wherein $R^{IV}$ may be substituted with up to six groups independently selected from hydroxy, amino, ($C_1$–$C_6$)alkoxy, ($C_1$–$C_6$)alkoxy($C_1$–$C_6$)alkoxy, amino, ($C_1$–$C_6$)alkylamino, di($C_1$–$C_6$)alkylamino, fluoro, chloro, bromo, iodo, carboxy, ($C_1$–$C_6$)alkoxycarbonyl, ($C_1$–$C_6$) alkylaminocarbonyl and di($C_1$–$C_6$)alkylaminocarbonyl.

As used herein, the term "optionally substituted ($C_3$–$C_{24}$) cyclo-alkyl($C_1$–$C_{18}$)alkenyl" refers to a ($C_3$–$C_{24}$)cycloalkyl ($C_1$–$C_{18}$)alkenyl group as defined above which are substituted in the cycloalkyl group by a substituent or substitutents independently selected from the substituents defined above for ($C_3$–$C_{24}$)cycloalkyl, and/or substituted in the alkenyl group by one or more substituents T as previously defined.

As used herein, the term "optionally substituted ($C_3$–$C_{24}$) cyclo-alkyl($C_1$–$C_{18}$)alkynyl" refers to a ($C_3$–$C_{24}$)cycloalkyl ($C_1$–$C_{18}$)alkynyl group as defined above which are substituted in the cycloalkyl group by a substituent or substitutents independently selected from the substituents defined above for ($C_3$–$C_{24}$)cycloalkyl, and/or substituted in the alkynyl group by one or more substituents T as previously defined.

As used herein, the term "optionally substituted ($C_6$–$C_{24}$) aryl" refers to a ($C_6$–$C_{24}$)aryl group as defined above wherein one or more hydrogen atoms are replaced by a substituent or substitutents independently selected from $R^V$ and T*, wherein T* is selected from the group consisting of —F, —Cl, —Br, —I, —CF$_3$, —CN, —NCO, —NCS, —OCN, —SCN, —N$_3$, —OR', —NR'R", —NR'C(O)R", —NR'C(O)OR", —NR'C(O)NR"R"', —NO$_2$, —SR', —S(O)R', —S(O)$_2$R', —S(O)OR', —S(O)$_2$OR', —S(O) NR'R", —S(O)$_2$NR'R", —NR" OR', —CHO, —OC(O)R', —OC(O)OR', —OC(O)NR'R", —C(O)R', —C(O)OR', —C(O)NR'R", —OC(S)R', —OC(S)OR', —OC(S)NR'R", —C(S)R', —C(S)OR', —C(S)NR'R", —SC(O)R', —SC(O) OR', —SC(O)NR'R", —C(O)SR', —SC(S)R', —SC(S)OR', —SC(S)NR'R", —C(S)SR', —C(=NR')OR", —C(=NR') SR", —C(=NR')NR"R"', —OS(O)R', —OS(O)$_2$R', —OS (O)OR', —OS(O)$_2$OR', —OS(O)NR'R", —OS(O)$_2$NR'R", NR'S(O)$_2$NR"R"', NR'S(O)$_2$R", —NHC(=NH)NR', —C(=NH)NR', —OP(O)(OR')R", —OP(O)(OR')OR", —OP(O)(SR')OR", —OP(O)(OR')NR"R"', —OP(O)R'R", and —B(OR')(OR"), wherein R', R" and R"' are as defined above with respect to the substituent T; and wherein RV is selected from ($C_1$–$C_{18}$)alkyl, ($C_2$–$C_{18}$)alkenyl, ($C_2$–$C_{18}$) alkynyl, ($C_3$–$C_{18}$)cycloalkyl, ($C_3$–$C_{18}$)cycloalkyl($C_1$–$C_{18}$) alkyl, ($C_3$–$C_{18}$)cycloalkyl($C_2$–$C_{18}$)alkenyl, ($C_3$–$C_{18}$) cycloalkyl-($C_2$–$C_{18}$)alkynyl, ($C_2$–$C_{18}$)acyl, ($C_6$–$C_{24}$)aryl ($C_2$–$C_{18}$)acyl, heterocyclic, heterocyclic-($C_1$–$C_{18}$)alkyl, heterocyclic($C_2$–$C_{18}$)alkenyl, and heterocyclic($C_2$–$C_{18}$) alkynyl, and wherein RV may be substituted with up to six groups independently selected from hydroxy, amino, ($C_1$–$C_6$)alkoxy, ($C_1$–$C_6$)aryloxy, ($C_1$–$C_6$)thioalkoxy, ($C_1$–$C_6$)thioaryloxy, ($C_1$–$C_6$)alkoxy($C_1$–$C_6$)alkoxy, amino, ($C_1$–$C_6$)alkylamino, di($C_1$–$C_6$)alkylamino, fluoro, chloro, bromo, iodo, carboxy, ($C_1$–$C_6$)alkoxycarbonyl, ($C_1$–$C_6$) alkylaminocarbonyl and di($C_1$–$C_6$)alkylaminocarbonyl. The term "optionally substituted ($C_6$–$C_{24}$)aryl" includes mono-, di- and polysubstituted ($C_6$–$C_{24}$)aryl groups. Examples of substituted aryl groups are loweralkyl-aryl, loweralkenyl-aryl, aryl loweralkyl-arylloweralkylcarbonyl-aryl, heterocyclic-aryl and heterocyclicloweralkyl-aryl wherein the aryl group is as exemplified above; halo-aryl such as 4-chlorophenyl, 2,4-dichlorophenyl, 1-chloro-2-naphthyl and 4-chloro-l-naphthyl; hydroxy-aryl such as 2-hydroxyphenyl, 1-hydroxy-2-naphthyl, 2-hydroxy-1-naphthyl, 2-hydroxy-8-naphthyl, 3,4,5-trihydroxyphenyl and 2,4,5-trihydroxyphenyl; loweralkoxyaryl such as 4-methoxyphenyl, 3,4-dimethoxyphenyl, 2,4-dimethoxyphenyl and 1-methoxy-2-naphthyl; carboxyaryl such as 2-carboxy-phenyl, 2-carboxy-l-naphthyl, 1-carboxy-2-naphthyl and 9-carboxy-2-anthracyl; acylaryl, wherein the acyl group is as exemplifed above under "($C_1$–$C_{18}$) acyl", such as 4-formylphenyl, 4-acetylphenyl, 2-benzoylphenyl, 2-methoxycarbonyl-phenyl, 2-ethoxycarbonyl-1-naphthyl, 1-methoxycarbonyl-2-naphthyl, 9-methoxycarbonyl-2-anthracyl, 2-carbamoyl-phenyl, 2-carbamoyl-1-naphthyl, 1-carbamoyl-2-naphthyl, 4-dimethylaminocarbonyl-phenyl, $^4$-morpholinocarbonylphenyl, 4-(2-pyridylmethoxy) carbonyl-phenyl and 4-benzyloxycarbonyl-phenyl; nitroaryl such as 4-nitrophenyl and 2,4-dinitrophenyl; amino- or (substituted amino)-aryl such as 4-aminophenyl, 2,4-diaminophenyl, 4-dimethylaminophenyl, 4-anilinophenyl, 2-(2,6-dichloroanilino)-phenyl, 2,4-di-(benzyloxycarbonylamino)-phenyl and 4-(2-quinolinecarbonylamino)-phenyl; and cyano-aryl such as 4-cyanophenyl, as well as aryl groups substituted with two or more of the substituents exemplified above.

As used herein, the term "optionally substituted ($C_6$–$C_{24}$) aryl($C_1$–$C_{18}$)alkyl" refers to a ($C_6$–$C_{24}$)aryl($C_1$–$C_{18}$)alkyl group as previously defined substituted in the aryl group with one or more substitutents defined above for ($C_6$–$C_{24}$) aryl and/or substituted in the alkyl group with one or more substitutents defined above for ($C_1$–$C_{18}$)alkyl. Examples of such groups are (substituted aryl)-lower-alkyl such as (substituted aryl)methyl, (substituted aryl)ethyl, (substituted aryl)propyl, (substituted aryl)iso-propyl, (substituted aryl)butyl, (substituted aryl)pentyl and (substituted aryl)hexyl, aryl(substituted loweralkyl) such as phenyl(substituted loweralkyl), naphthyl(substituted loweralkyl), biphenyl(substituted loweralkyl), tetrahydronaphthyl(substituted loweralkyl), indenyl-(substituted loweralkyl) and indanyl(substituted loweralkyl), and (substituted aryl)-(substituted loweralkyl), wherein in each case substituted aryl is as exemplified above with respect to "optionally substituted $(C_6-C_{24})$aryl" and (substituted loweralkyl) is as exemplified above with respect to "optionally substituted $(C_1-C_{18})$alkyl".

As used herein, the term "optionally substituted $(C_6-C_{24})$aryl$(C_1-C_{18})$alkenyl" refers to a $(C_6-C_{24})$aryl$(C_1-C_{18})$alkenyl group as previously defined substituted in the aryl group with one or more substitutents defined above for $(C_6-C_{24})$aryl and/or substituted in the alkenyl group with one or more substitutents defined above for $(C_1-C_{18})$alkyl.

As used herein, the term "optionally substituted $(C_6-C_{24})$aryl$(C_1-C_{18})$alkynyl" refers to a $(C_6-C_{24})$aryl$(C_1-C_{18})$alkynyl group as previously defined substituted in the aryl group with one or more substitutents defined above for $(C_6-C_{24})$aryl and/or substituted in the alkynyl group with one or more substitutents defined above for $(C_1-C_{18})$alkyl.

As used herein, the term "optionally substituted $(C_1-C_{18})$acyl" refers to a $(C_1-C_{18})$acyl group as previously defined which may be substituted with one or more groups selected from the substituents defined for $(C_1-C_{18})$alkyl, and includes within its meaning an acyl residue of a naturally occurring or synthetic amino acid or azaamino acid, or an acyl residue of a peptide chain containing 24 naturally occurring or synthetic amino acids and/or azaamino acids.

Examples of substituted acyl groups include acyl residues of any of the naturally occurring or synthetic amino acids exemplified herein, hydroxyloweralkanoyl, loweralkoxyloweralkanoyl, acetylloweralkanoyl, cyanoloweralkanoyl, carboxyloweralkanoyl, hydroxycarboxyloweralkanoyl, fluoroloweralkanoyl, chloroloweralkanoyl, bromoloweralkanoyl, thioloweralkanoyl, loweralkanethioloweralkanoyl, aminoloweralkanoyl, loweralkylaminoloweralkanoyl, di-(loweralkylamino)loweralkanoyl, carbamoylloweralkanoyl, loweralkoxycarbonyl, carbamoyl, loweralkylaminocarbonyl and di-(loweralkylamino)-carbonyl, where loweralkanoyl is an alkanoyl group of from 1 to 6 carbon atoms, for example formyl, acetyl, propionyl, butyryl, isobutyryl, pentanoyl and hexanoyl, and where loweralkyl signifies a $(C_1-C_6)$alkyl group such as methyl, ethyl, n-propyl, iso-propyl, n-butyl, iso-butyl, sec-butyl, tert-butyl, n-pentyl, iso-pentyl, neo-pentyl and hexyl.

As used herein, the term "optionally substituted heterocyclic" refers to a heterocyclic group as previosly defined wherein one or more hydrogen atoms may be replaced with a group selected from the substitutents defined above with regard to optionally substituted $(C_6-C_{24})$aryl. Examples of substituted heterocyclic groups include loweralkylheterocyclic, arylheterocyclic, aryloxyheterocyclic, loweralkoxyheterocyclic, oxo-heterocyclic, hydroxyheterocyclic, loweralkoxycarbonyl-heterocyclic and loweralkanoylheterocyclic.

As used herein, the term "optionally substituted heterocyclic$(C_1-C_{18})$alkyl" refers to a heterocyclic$(C_1-C_{18})$alkyl group as previously defined substituted in the hetero-cyclic group with one or more substitutents defined above for heterocyclic and/or substituted in the alkyl group with one or more substitutents defined above for $(C_1-C_{18})$alkyl. Examples of such groups are (substituted heterocyclic)-lower-alkyl such as (substituted heterocyclic)methyl, (substituted heterocyclic)ethyl, (substituted heterocyclic)propyl, (substituted heterocyclic)iso-propyl, (substituted heterocyclic)butyl, (substituted heterocyclic)pentyl and (substituted heterocyclic)hexyl, heterocyclic(substituted loweralkyl) such as pyrrolyl(substituted loweralkyl), indolyl(substituted loweralkyl), quinolyl(substituted loweralkyl), tetrahydroquinolyl(substituted loweralkyl), pyridyl-(substituted loweralkyl), morpholinyl(substituted loweralkyl), piperidinyl(substituted loweralkyl), thiomorpholinyl(substituted loweralkyl), thienyl(substituted loweralkyl), furanyl(substituted loweralkyl), benzfuranyl(substituted loweralkyl), pyrrolidinyl-(substituted loweralkyl) and iso-quinolyl(substituted loweralkyl), and (substituted heterocyclic)(substituted loweralkyl), wherein in each case substituted heterocyclic is as exemplified above with respect to "optionally substituted heterocyclic" and (substituted loweralkyl) is as exemplified above with respect to "optionally substituted $(C_1-C_{18})$alkyl".

As used herein, the term "optionally substituted heterocyclic$(C_1-C_{18})$alkenyl" refers to a heterocyclic$(C_1-C_{18})$alkenyl group as previously defined substituted in the heterocyclic group with one or more substitutents defined above for heterocyclic and/or substituted in the alkenyl group with one or more substitutents defined above for $(C_1-C_{18})$alkenyl.

As used herein, the term "optionally substituted heterocyclic$(C_1-C_{18})$alkynyl" refers to a heterocyclic$(C_1-C_{18})$alkynyl group as previously defined substituted in the heterocyclic group with one or more substitutents defined above for heterocyclic and/or substituted in the alkynyl group with one or more substitutents defined above for $(C_1-C_{18})$alkynyl.

As used herein, the term "optionally substituted alkylidene" refers to an alkylidene radical as previously defined, in which one or more hydrogen atoms is replaced by substituent(s) independently selected from the substituents defined above in connection with "optionally substituted $(C_1-C_{18})$allyl".

As used herein, the term "naturally occurring or synthetic amino acid" refers to a compound of the formula $HN(R_{401})(CH(R_{400}))_pCOOH$, wherein $R_{400}$ and $R_{401}$ independently have the meaning of $R_{20}$ as previously defined, and p is 1, 2 or 3, and wherein $R_{400}$ and $R_{401}$ together with the carbon and nitrogen to which they are bound may together form a saturated or unsaturated cyclic, bicyclic or fused ring system. Examples of naturally occurring or synthetic amino acids include alanine, cyclohexylalanine, anthranilic acid, arginine, asparagine, aspartic acid, cysteine, β-phenylcysteine, cystine, glutamic acid, glutamine, glycine, cyclohexylglycine, tetrahydrofuranylglycine, histidine, homoserine, hydroxyproline, isoleucine, leucine, lysine, 4-azalysine, δ-hydroxylysine, methionine, norleucine, norvaline, ornithine, phenylalanine, 4-aminophenylalanine, 4-carboxyphenylalanine, 4-chlorophenylalanine, phenylglycine, 8-phenylserine, proline, serine, threonine, trans-3-hydroxyproline, trans4-hydroxyproline, tryptophan, tyrosine, valine, indoline-2-carboxylic acid, 1,2,3,4-tetrahydroisoquinoline-3-carboxylic acid, aminomalonic acid, aminomalonic acid monoamide, α-aminobutyric acid, α,γ-diaminobutyric acid and α,β-diaminopropionic acid. Other amino acids, and peptides derived therefrom, are disclosed in J. S. Davies, ed., *Amino Acids and Peptides*, Chapman and Hall, London, 1985, the disclosure of which is incorporated herein by reference.

As used herein, the term "residue of a naturally occurring or synthetic amino acid" refers to a group of the formula —N($R_{401}$)(CH($R_{400}$))$_p$C(O)—, wherein $R_{400}$, $R_{401}$, and p are as defined above with regard to "naturally occurring or synthetic amino acid".

As used herein, the term "azaamino acid" refers to an amino acid in which a —CH($R_{400}$)— group has been replaced by a group —($R_{401}$)—, wherein $R_{401}$ has the meaning of $R_{20}$ as previously defined.

Suitable pharmaceutically acceptable salts of the compound of formula (I) are, where the compound of formula (I) contains a basic nitrogen atom, acid addition salts of pharmaceutically acceptable inorganic acids such as hydrochloric, sulfuric, phosphoric, nitric, carbonic, boric, sulfamic, hydrobromic or hydriodic, or with pharmaceutically acceptable organic acids such as acetic, propionic, butyric, tartaric, maleic, hydroxymaleic, methylmaleic, fumaric, malic, citric, lactic, mucic, gluconic, glucoheptonic, glucaric, glucuronic, lactobionic, benzoic, naphthoic, succinic, oxalic, phenylacetic, methanesulphonic, ethanesulfonic, 2-hydroxyethanesulfonic, ethane-1,2-disulfonic, laurylsulfonic, toluenesulphonic, benzenesulphonic, naphthalene-2-sulfonic, salicylic, 4-aminosalicylic, sulphanilic, aspartic, glutamic, edetic, stearic, palmitic, oleic, lauric, pantothenic, tannic, ascorbic, valeric, glycolic, cinnamic, mandelic, 2-phenoxybenzoic, 2-acetoxybenzoic, embonic, nicotinic, isonicotinic, N-cyclohexylsulfamic or other acidic organic compounds, such as 2- or 3-phosphoglycerate and glucose-6-phosphate. Where the compound of formula (I) contains an acid group, suitable pharmaceutically acceptable salts of the compound of formula (I) are addition salts of pharmaceutically acceptable bases such as lithium, sodium, potassium, ammonium, magnesium, calcium and zinc salts, or salts formed with organic amines such as methylamine, dimethylamine, trimethylamine, ethylamine, diethylamine, triethylamine, N-methyl-N-ethylamine, mono-, bis- or tris-(2-hydroxyethyl)amine, 2-hydroxy-tert-butylamine, tris (hydroxymethyl)methylamine, N,N-dimethyl-N-(2-hydroxyethyl)-amine, tri-(2-hydroxyethyl)-amine, N-methyl-D-glucamine, or tributylamine. Compounds of formula I having acid and basic groups can also form internal salts. Other suitable salts are described, for example, in S. M. Berge, et al., "Pharmaceutical Salts" *J. Pharm. Sci.*, 66 1–19 (1977) which is incorporated herein by reference.

The expression "prodrug" as used herein refers to a pharmaceutically acceptable derivative of a compound of formula (I) which is transformed into a compound of formula (I) after administration of the prodrug to a living animal or human, and which has enhanced stability, delivery characteristics and/or therapeutic value compared to the compound of formula (I) from which it derives.

The expression "protecting group" as used herein refers to a group which may be used temporarily to modify a functional group, for example to prevent that functional group from being affected by, or from undesirably affecting the outcome of, a desired reaction involving another functional group in the molecule and/or to prevent premature metabolism of the compound of formula (I) after administration to a patient before the compound can reach the desired site of action. Suitable protecting groups are described, for example in Greene, T. W., Protective Groups in Organic Synthesis (John Wiley & Sons, New York, 1981) and McOmie, J. F. W., Protective Groups in Organic Chemistry (Plenum Press, London, 1973).

Examples of suitable protecting groups for hydroxyl or mercapto substituents include substituted methyl ethers, for example, methoxymethyl, benzyloxymethyl, t-butyloxymethyl, 2-methoxyethoxymethyl, 1-ethoxyethyl, methylthiomethyl, 1-methylthioethyl, benzyl, allyl, triphenylmethyl and the like, other etherifying groups such as 2-tetrahydrofuryl, 2-tetrahydropyranyl and vinyl, or by acyl and carbonate groups such as formyl, 2,2-dichloroacetyl, 2,2,2-trichloroacetyl, t-butyloxycarbonyl, benzyloxycarbonyl, 4-nitrobenzyloxycarbonyl, and 4-methoxybenzyloxycarbonyl, or by silyl groups such as trimethylsilyl, t-butyldimethylsilyl, tribenzylsilyl, triphenylsilyl and the like.

Suitable protecting groups for amino substituents include acyl groups such as formyl, acetyl, 3-phenylpropionyl, chloroacetyl, trifluoroacetyl, trichloroacetyl, benzoyl, 4-nitrobenzoyl, 4-methoxybenzoyl, t-butyloxycarbonyl, benzyloxycarbonyl, 4-nitrobenzyloxycarbonyl, 4-chlorobenzyloxycarbonyl, 4-methoxybenzyloxycarbonyl, 9-fluorenylmethoxycarbonyl, (2-pyridyl)methoxycarbonyl, quinoline-2-carbonyl, 2-trimethylsilylethoxycarbonyl, or trimethylsilyl, or an aminoacyl residue.

Suitable protecting groups for carboxyl substituents include esters, for example methyl, ethyl, tert-butyl, benzyl, 4-nitrobenzyl, 4-methoxybenzyl, methoxymethyl, 2-methoxyethoxymethyl, benzyloxymethyl, methylthiomethyl, 2,2,2-trichloroethyl, 2-bromoethyl, 2-iodoethyl, 2-trimethylsilylethyl, 2-triphenylsilylethyl, t-butyldimethylsilyl or trimethylsilyl esters.

Suitable protecting groups for carbonyl substituents include acetals such as dimethyl, diethyl, dibutyl and dibenzyl, thioacetals such as S,S-dimethyl and S,S-diethyl, cyclic acetals and thioacetlas such as 1,3-dioxanes, 1,3-dioxolanes, 1,3-oxathiolanes, 1,3-dithianes and 1,3-dithiolanes, and oximes and hydrazones such as O-benzyl oximes, O-phenylthiomethyl oximes and N,N-dimethyl hydrazones.

The expression "solubilising group Px" as used herein refers to a group which may be used to derivatise a functional group so as to enhance the solubility of the compound of formula (I) in water or aqueous media. Examples of solubilising groups for inclusion in the compound of formula (I) are groups of the formula Px* or salts thereof, where Px* is selected from:

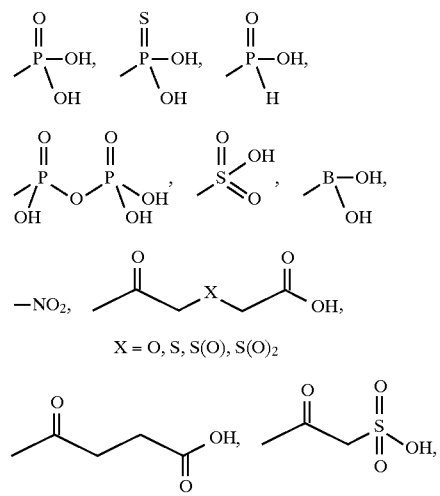

-continued

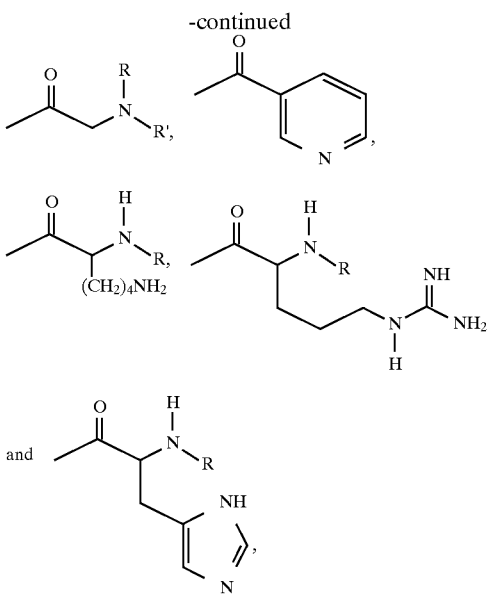

and wherein R and R' are independently hydrogen or $C_1$–$C_4$ alkyl. Also included within the meaning of Px are groups of the following formulae, wherein Px* and D are as previously defined, and R is H or $C_1$–$C_4$ alkyl:

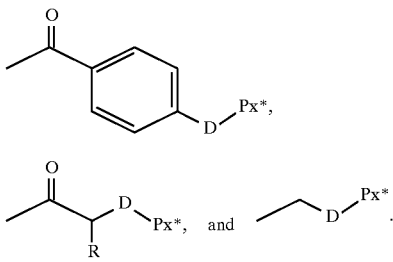

Where the compound of formula (I) includes two functional groups capable of being derivatised by a solubilising group, the two funtional groups being in sufficiently close proximity to one another, it will be appreciated that certain of the solubilising groups exemplified above are capable of forming cyclic structures, for example including the following structural units:

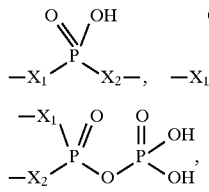

wherein $X_1$ and $X_2$ are independently selected from O, S and $NR_6$ wherein $R_6$ is as previously defined. Solubilising groups in a cyclic structure, such as those exemplifed above, also fall within the meaning of "solubilising group" as used herein.

Where the solubilising group is acidic, a salt thereof is typically a salt of an alkali metal or ammonia, such as $Na^+$, $K^+$ or $NH_4^+$. Where the solubilising group is basic, a salt thereof is typically a salt of a strong inorganic acid such as hydrochloric acid, sulfuric acid, phosphoric acid or nitric acid. Typically, the solubilising group is a sodium or potassium salt of a phosphate or phosphite residue.

Solubilising or protecting groups which are included in the compound of formula (I) must be amenable to hydrolytic or metabolic cleavage in vivo.

In one form of the present invention, in the compound of the general formula (I), B is typically selected from the group consisting of

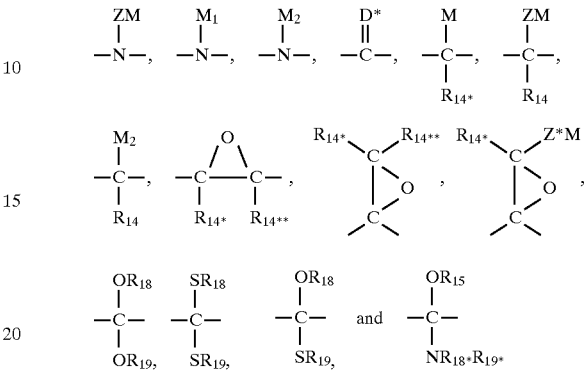

where Z, Z*, M, $M_1$, $M_2$, D*, $R_{14}$, $R_{14*}$, $R_{14**}$, $R_{15}$, $R_{18}$, $R_{18*}$, $R_{19}$ and $R_{9*}$ are as previously defined, and V is $YR_2$, Y* or $C(R_{30})$=Y, wherein $R_2$, $R_{30}$ and Y are as previously defined, and wherein Y is selected from the group consisting of

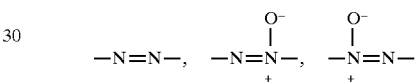

and Y* is selected from the group consisting of

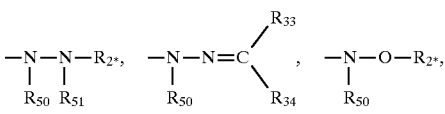

wherein $R_{33}$, $R_{34}$, $R_{50}$, $R_5$, and $R_{2*}$ are as previously defined.

More typically, the compound of the general formula (I) in this form of the invention has the structure represented by formula (IA):

$$R_{10}-N-\underset{\underset{R_{13}}{|}}{\overset{\overset{R_{1*}}{|}}{C}}-B^*-\underset{\underset{R_{13*}}{|}}{\overset{\overset{R_{12*}}{|}}{C}}-Y_1 \quad (IA)$$

with $R_{12}$ on the first C.

where $R_{1*}$, $R_{10}$, $R_{12}$, $R_{12*}$, $R_{13}$ and $R_{13*}$ are as previously defined, B* is selected from the group consisting of

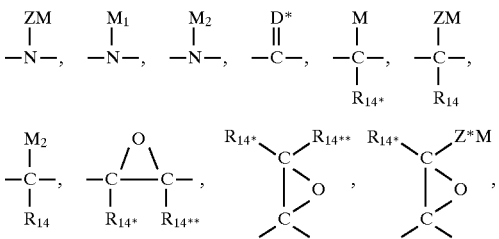

-continued

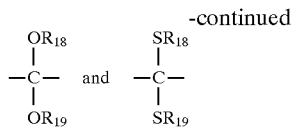

where $Z$, $Z^*$, $M$, $M_1$, $M_2$, $D^*$, $R_{14}$, $R_{14*}$, $R_{14**}$, $R_{18}$ and $R_{19}$ are as previously defined, and $Y_1$ is selected from the group consisting of

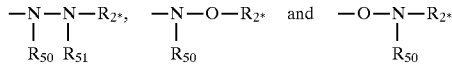

wherein $R_{50}$, $R_{51}$, and $R_{2*}$ are as previously defined.

Even more typically, the compound of the general formula (I) in this form of the invention has the structure represented by formula (IB):

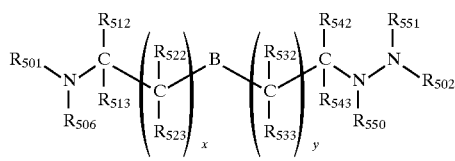

wherein x and y are independently 0 or 1, B is selected from the group consisting of

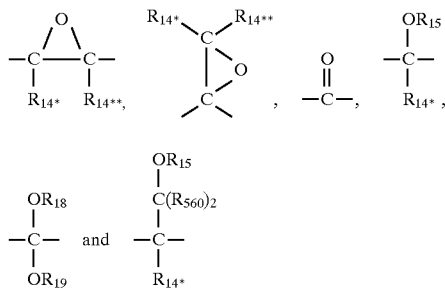

wherein $R_{14*}$, $R_{14**}$, $R_{15}$, $R_{18}$ and $R_{19}$ are as previously defined and each $R_{560}$ is independently hydrogen or $(C_1-C_4)$ alkyl, $R_{502}$ and $R_{506}$ are independently a group $R_{600}$, wherein $R_{600}$ is selected from the group consisting of hydrogen, C(O)$OR_{621}$, C(O)$SR_{621}$, C(O)$NR_{621}R_{622}$, $(C_1-C_6)$alkyl, $(C_2-C_6)$alkenyl, $(C_5-C_{10})$cycloalkyl, $(C_5-C_{10})$cycloalkyl$(C_1-C_6)$alkyl, $(C_5-C_{10})$cycloalkyl$(C_2-C_6)$alkenyl, $(C_6-C_{10})$aryl, $(C_6-C_{10})$aryl$(C_1-C_6)$allyl, $(C_6-C_{10})$aryl$(C_2-C_6)$alkenyl, $(C_1-C_6)$acyl, heterocyclic, heterocyclic$(C_1-C_6)$alkyl and heterocyclic$(C_2-C_6)$alkenyl, each of which may be substituted by up to three substituents selected from the substituents defined above for "optionally substituted $(C_1-C_{18})$alkyl" and $R_{621}$ and $R_{622}$ have the meaning of $R_{21}$ and $R_{22}$ respectively, as previously defined, or $R_{621}$ and $R_{622}$ together form a saturated or unsaturated cyclic, bicyclic or fused ring system as defined below, $R_{501}$ is selected from the group consisting of $R_{600}$ as previously defined, $S(O)OR_{632}$, $S(O)_2R_{632}$, $S(O)NR_{632}R_{633}$, $S(O)_2R_{632}R_{633}$, $NH_2$, $NHR_{631}$ and $NR_{631}R_{632}$, wherein $R_{631}$ has the meaning of $R_6$ as previously defined and $R_{632}$ and $R_{633}$ independently have the meaning of $R_{20}$ as previously defined, or $R_{50}$, and $R_{506}$ together form part of a saturated or unsaturated cyclic, bicyclic or fused ring system, or $R_{631}$ and $R_{632}$, or $R_{632}$ and $R_{633}$ together form a saturated or unsaturated cyclic, bicyclic or fused ring system as defined below, $R_{512}$ and $R_{542}$ independently have the meaning of $R_{600}$ as previously defined, $R_{522}$ and $R_{532}$ are independently selected from the group consisting of $R_{600}$ as previously defined, F, Cl, Br and I, $R_{513}$ and $R_{543}$ are independently selected from the group consisting of $R_{600}$ as previously defined and $R_{200}$ as previously defined, $R_{523}$ and $R_{533}$ are independently selected from the group consisting of $R_{600}$ as previously defined, F, Cl, Br, I, and $R_{200}$ as previously defined, $R_{550}$ has the meaning of $R_6$ as previously defined and $R_{551}$ is selected from the group consisting of $R_{650}$, hydrogen, $S(O)OR_{632}$, $S(O)_2R_{632}$, $S(O)NR_{632}R_{633}$ and $S(O)_2R_{632}R_{633}$, wherein $R_{650}$ has the meaning of $R_6$ as previously defined and $R_{632}$ and $R_{633}$ are as previously defined, or $R_{632}$ and $R_{633}$ together form a saturated or unsaturated cyclic, bicyclic or fused ring system as defined below, or $R_{550}$ and one of $R_{55}$, and $R_{502}$ together form a diazaheterocycle wherein $R_{550}$, $R_{551}$ or $R_{502}$ and the two nitrogen atoms to which they are bonded are part of a stable 5 to 10-membered ring which may comprise up to two further heteroatoms selected from O, S and N and to which may be fused one or more cycloalkyl, cycloalkenyl, aryl or heterocyclic residues, which diazaheterocycle may be substituted by one or more of the substituents defined above for "optionally substituted $(C_1-C_{18})$alkyl", and wherein two substituents may together form part of a ring, or one pair selected from $R_{512}$ and $R_{513}$, $R_{522}$ and $R_{523}$ (when present), $R_{532}$ and $R_{533}$ (when present), and $R_{542}$ and $R_{543}$, together are $=O$;

wherein, when B is other than

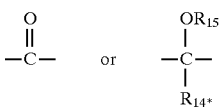

then at least one of conditions (i) to (xi) below applies:

(i) at least one of $R_{512}$ and $R_{542}$ is a group R wherein $R_{655}$ is selected from the group consisting of $(C_1-C_6)$alkyl $(C_6-C_{10})$aryl, $(C_2-C_6)$alkenyl-$(C_6-C_{10})$aryl, $(C_5-C_{10})$ cycloalkyl$(C_2-C_6)$alkenyl, $(C_5-C_{10})$cycloalkyl-$(C_6-C_{10})$aryl, acyl$(C_6-C_{10})$aryl, heterocyclic$(C_1-C_6)$ alkyl, heterocyclic$(C_2-C_6)$alkenyl, heterocyclic $(C_6-C_{10})$aryl, $C(D^*)OR_{21*}$, $C(D^*)SR_{21}^*$ and $C(D^*)$ $NR_{21*}R_{22*}$, wherein $D^*$, $R_{21*}$, and $R_{22*}$ are as previously defined, (ii) at least one of $R_{522}$ and $R_{532}$, when present, is selected from the group consisting of $R_{655}$ as previously defined, F, Cl, Br and I, (iii) at least one of $R_{513}$ and $R_{543}$, when present, is selected from the group consisting of $R_{655}$ as previously defined, and $R_{200}$ as previously defined, (iv) at least one of $R_{523}$ and $R_{533}$, when present, is selected from the group consisting of $R_{655}$ as previously defined, F,Cl Br, I and $R_{200}$ as previously defined, (v) $R_{550}$ is a group $R_{656}$, wherein $R_{656}$ is selected from the group consisting of $(C_1-C_6)$alkyl$(C_6-C_{10})$aryl, $(C_2-C_6)$alkenyl$(C_6-C_{10})$aryl, $(C_5-C_{10})$cycloalkyl $(C_2-C_6)$alkenyl, $(C_5-C_{10})$cycloalkyl$(C_6-C_{10})$aryl, acyl $(C_6-C_{10})$aryl, heterocyclic$(C_1-C_6)$alkyl, heterocyclic $(C_2-C_6)$alkenyl, heterocyclic$(C_6-C_{10})$aryl, (vi) $R_{551}$ is selected from the group consisting of $R_{656}$ as previously defined, $S(O)OR_{632}$, $S(O)_2R_{632}$, $S(O)$ $NR_{632}R_{633}$ and $S(O)_2R_{632}R_{633}$, wherein $R_{632}$ and $R_{633}$ are as previously defined, (vii) $R_{502}$ is selected from the group consisting of $R_{656}$ as previously defined, $C(D^*)SR_{21*}$ and $C(D^*)NR_{21*}R_{22*}$, wherein $D^*$, $R_{21*}$ and $R_{22*}$ are as previously defined, (viii) $R_{502}$ and $R_{551}$ are both hydrogen or are both $(C_1-C_6)$acyl, (ix) $R_{14*}$ is selected from the group consisting of $C(D^*)OR_{40}$, $C(D^*)SR_{40}$ and $C(D^*)NR_{40}R_{41}$, wherein $R_{40}$ and $R_{41}$, are as previously defined, (x) $R_{501}$ is selected from the group consisting of $R_{656}$ as previously defined, $S(O)OR_{632}$, $S(O)_2R_{632}$, $S(O)NR_{632}R_{633}$, $S(O)_2R_{632}R_{633}$, $NH_2$, $NHR_{631}$ and $NR_{631}R_{632}$, wherein $R_{632}$ and $R_{633}$ are as previously defined, (xi) $R_{501}$ and $R_{506}$ are both $(C_1-C_6)$acyl, and wherein when B is

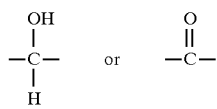

then at least one of the following conditions also applies:

(xii) x+y>0, (xiii) x+y=0 and at least one of $R_{532}$ and $R_{533}$ is other than hydrogen, (xiv) $R_{50}$ and $R_{51}$ together form a diazaheterocycle as previously defined, (xv) at least one of $R_{501}$, $R_{502}$, $R_{506}$ and $R_{551}$ is optionally substituted heterocyclic$(C_1-C_{18})$alkyl, and (xvi) at least one of $R_{512}$, $R_{542}$, $R_{522}$, $R_{532}$, $R_{513}$, $R_{543}$, $R_{523}$ and $R_{533}$ is selected from the group consisting of $C(O)O_{621}$, $C(O)SR_{621}$ and $C(O)NR_{621}R_{622}$, wherein $R_{621}$ and $R_{622}$ are as previously defined.

Examples of typical unsubstituted diazaheterocycles are:

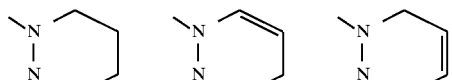

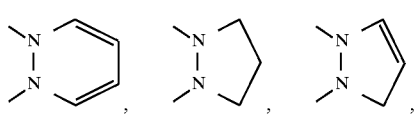

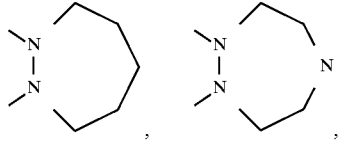

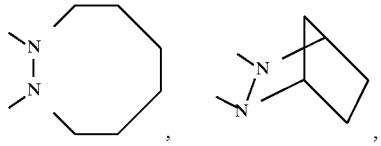

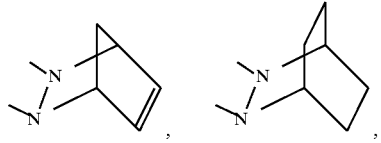

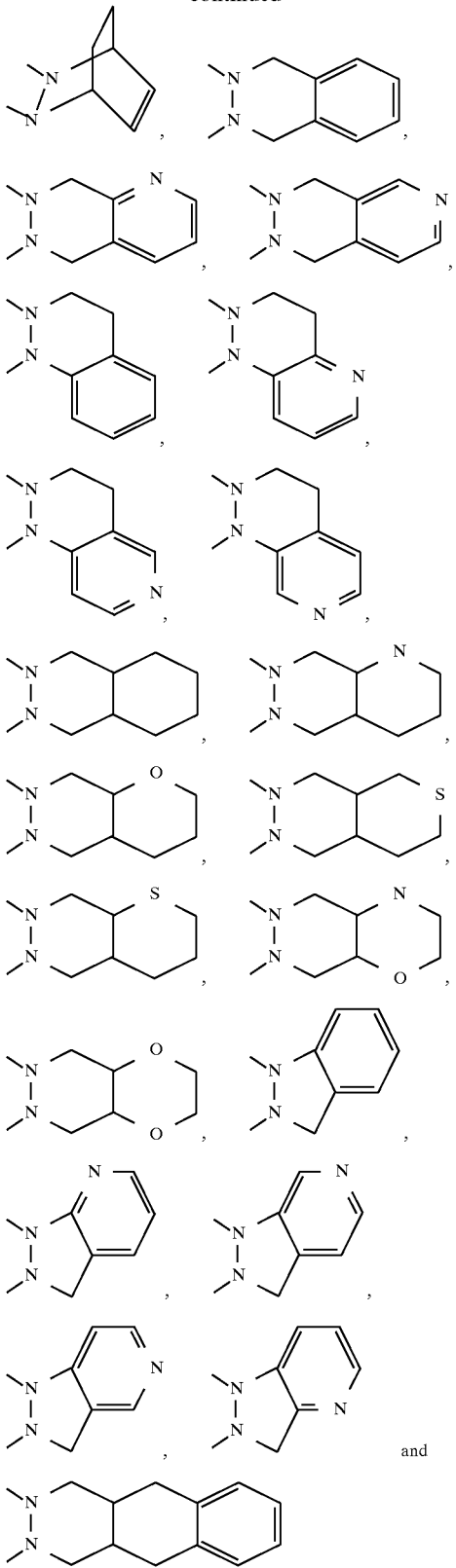

Other forms of the first embodiment of the invention have the structures represented by formulae (IC) to (IAW) below, in which each AA is independently a residue of a naturally occurring or synthetic amino acid as herein defined; $R_{1*}$, $R_1$, X and X* are as previously defined; Ra to Rj independently are —$(CH_2)_{a-6}$OPy, wherein a can be 0, 1, 2, 3, 4 or 5, halogen or $R_6$, more typically —$(CH_2)_{0-3}$OPy, fluoro, chloro or $R_{6*}$ wherein Py is a solubilising group Px as defined herein, $R_6$ is as previously defined and $R_{6*}$ is is selected from the group consisting of
hydrogen,
$R_{20*}$, wherein $R_{20*}$ is selected from the group consisting of
optionally substituted ($C_1$–$C_6$)alkyl,
optionally substituted ($C_2$–$C_6$)alkenyl,
optionally substituted ($C_2$–$C_6$)alkynyl,
optionally substituted ($C_3$–$C_8$)cycloalkyl,
optionally substituted ($C_3$–$C_8$)cycloalkyl($C_1$–$C_6$)alkyl,
optionally substituted ($C_3$–$C_8$)cycloalkyl($C_2$–$C_6$)alkenyl,
optionally substituted ($C_3$–$C_8$)cycloalkyl($C_2$–$C_6$)alkynyl,
optionally substituted ($C_6$–$C_{10}$)aryl,
optionally substituted ($C_6$–$C_{10}$)aryl($C_1$–$C_6$)alkyl,
optionally substituted ($C_6$–$C_{10}$)aryl($C_2$–$C_6$)alkenyl,
optionally substituted ($C_1$–$C_6$)acyl,
optionally substituted heterocyclic, and
optionally substituted heterocyclic($C_1$–$C_6$)alkyl,
C(O)O$R_{21}$,
C(O)S$R_{21}$, and
C(O)N$R_{21}R_{22}$, wherein $R_{21}$ and $R_{22}$ independently are selected from hydrogen and $R_{20*}$ as previously defined, or $R_{21}$ and $R_{22}$ together form a saturated or unsaturated cyclic, bicyclic or fused ring system as previously defined:

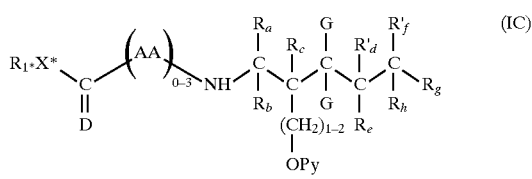

wherein D' is O or S, and each G is independently hydrogen or $R_{200}$ as previously defined and wherein R'$_d$ and R'$_f$ are $R_d$ and $R_f$ or, taken together, may be trimethylene or tetramethylene optimally substituted with —C(O)OR; or —C(O)N$R_iR_j$;

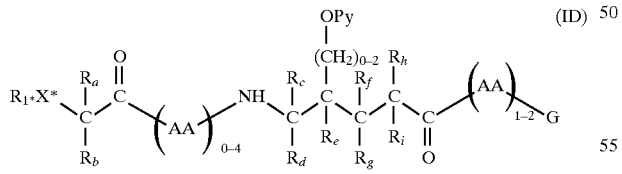

wherein G is selected from $R_{1*}$ and X*$R_{1*}$;

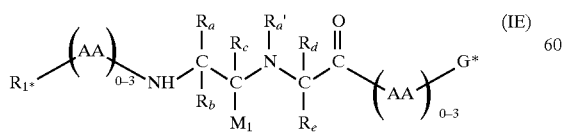

wherein $R_a$' is OPy or $R_6$ as previously defined, $M_1$ is $R_6$ as previously defined, $(CH_2)_{1-2}$OPy or $(CH_2)_{1-2}$NHPy, and G* is OR$_2$ or NR$_i$R$_2$;

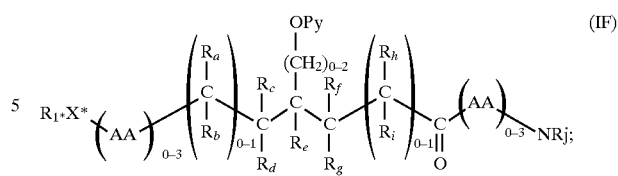

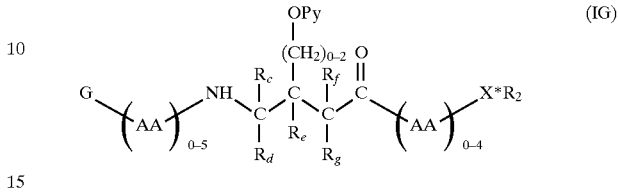

wherein G is hydrogen, $R_a$, $R_{1*}$X* or $R_{1*}$X*C($R_a$)($R_b$)C(O), and wherein $R_a$, $R_{1*}$, and the atoms to which they are bound may optionally form a saturated or unsaturated cyclic, bicyclic or fused ring system;

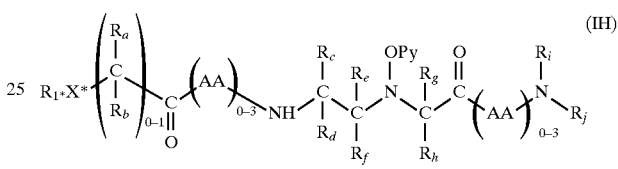

wherein $R_a$, $R_{1*}$, and the atoms to which they are bound may optionally form a saturated or unsaturated cyclic, bicyclic or fused ring system;

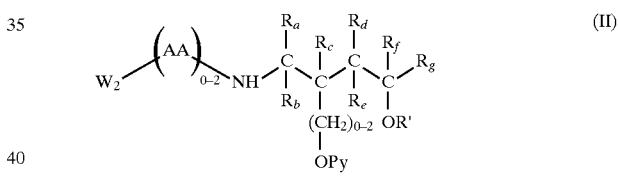

wherein $W_2$ is $R_1$X or $R_6$ as previously defined, and R' is Py or $R_6$ as previously defined, or R' and Py, taken together with the oxygen atoms to which they are attached form a group selected from

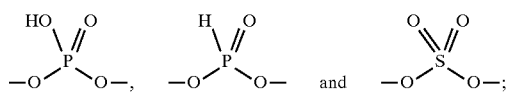

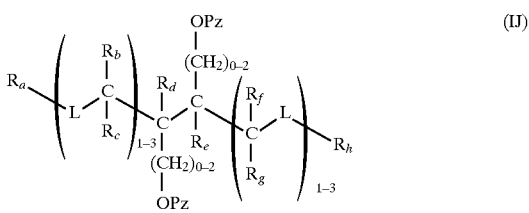

wherein each L is independently as previously defined and each Pz is independently hydrogen or Py, provided that at least one Pz is Py or, when each Pz is Py, the groups Py, together with the oxygen atoms to which the are bound define a cyclic group selected from

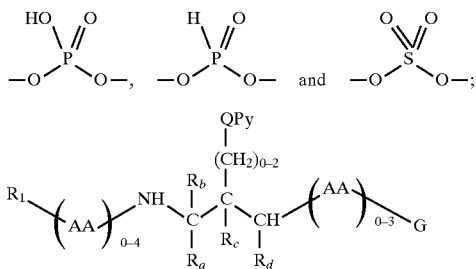

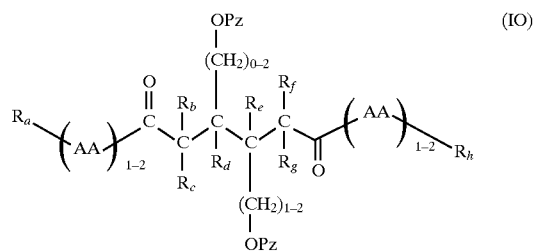

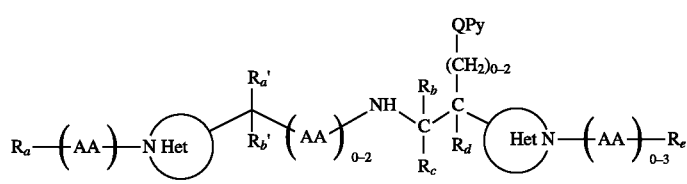

wherein Q is O or $NR_f$ and G is $R_{1*}$ or $X*R_{1*}$;

wherein each Pz is independently hydrogen or Py, provided that at least one Pz is Py;

wherein each

is independently a 5- or 6- membered saturated or unsaturated heterocycle containing a nitrogen atom and optionally additionally one or two heteroatoms selected from nitrogen, oxygen and sulfur, and wherein $R_a'$ and $R_b'$ independently have the meaning of $-(CH_2)_{0-6}OPy$ or $R_6$, or taken together are =O;

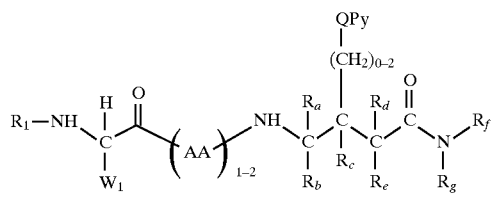

wherein $W_1$ is selected from $R_1X$ and $R_{1*}X*$, and Q is selected from O and $NR_h$;

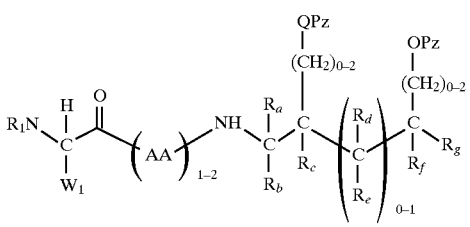

wherein $W_1$ is selected from $R_1X$ and $R_{1*}X*$, each Pz is independently hydrogen or Py, provided that at least one Pz is Py, and Q is selected from O and $NR_h$;

wherein

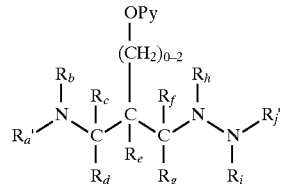

is a 5- or 6- membered saturated or unsaturated heterocycle containing a nitrogen atom and optionally additionally one or two heteroatoms selected from nitrogen, oxygen and sulfur;

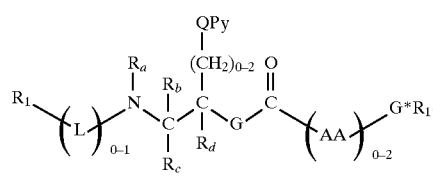

wherein $R_a'$ and $R_j'$ are independently selected from $R_1$ and $R_{1*}$, as previously defined;

wherein G is selected from

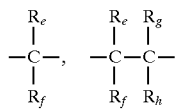

and a saturated or unsaturated cyclic, bicyclic or fused ring system, Q is O or NH, and G* is X or X* as previously defined;

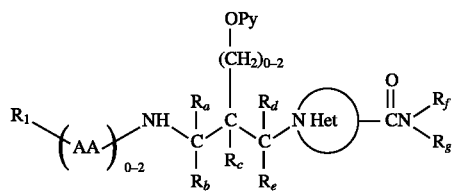 (IS)

wherein

is a 5–12 membered saturated or unsaturated cyclic, bicyclic or fused ring system containing a nitrogen atom and optionally additionally from 1 to 4 heteroatoms selected from nitrogen, oxygen and sulfur;

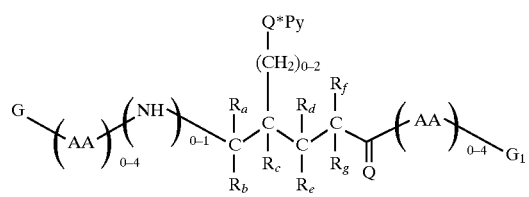 (IT)

wherein G is selected from hydrogen and $R_{1*}X^*$, Q is O, S or NH, Q* is O or NH, and $G_1$ is selected from $R_1$ and $R_{1*}X^*$;

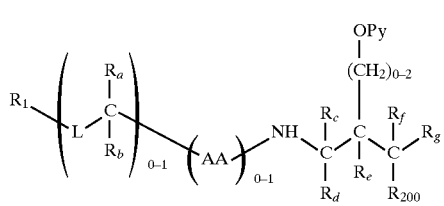 (IU)

wherein $R_2OO$ is as previously defined;

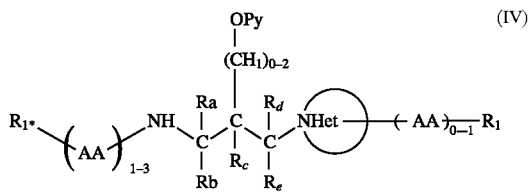 (IV)

wherein

is an optionally substituted 5–12 membered saturated or unsaturated cyclic, bicyclic or fused ring system containing a nitrogen atom and optionally additionally from 1 to 4 heteroatoms selected from nitrogen, oxygen and sulfur;

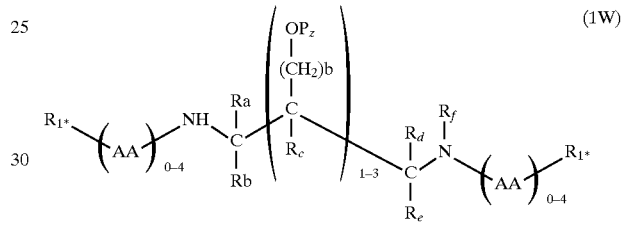 (1W)

wherein b is 0, 1 or 2, provided that at least one b is greater than 0, and each Pz is independently hydrogen or Py, provided that at least one Pz is Py;

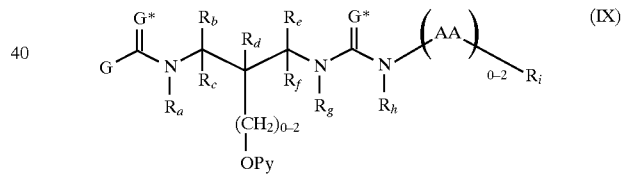 (IX)

wherein each G* is independently selected from O, S and $NR_6$ and G is selected from $OR_6$, $NHR_6$ and $R_{20}$;

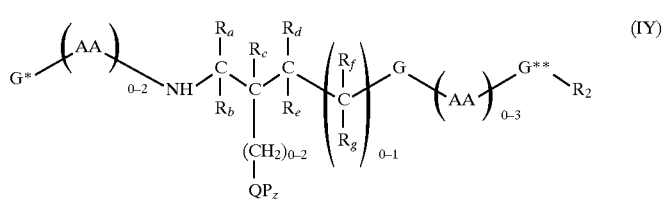 (IY)

wherein G is —C(O)— or —CH$_2$—, G* is $R_1$ or $R_{1*}$, G** is —O— or —NR$_h$—, Q is —O— or —NR$_i$ and Pz is selected from the group consisting of

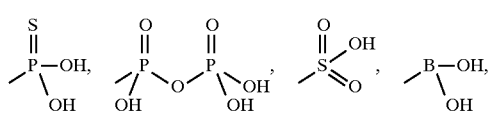

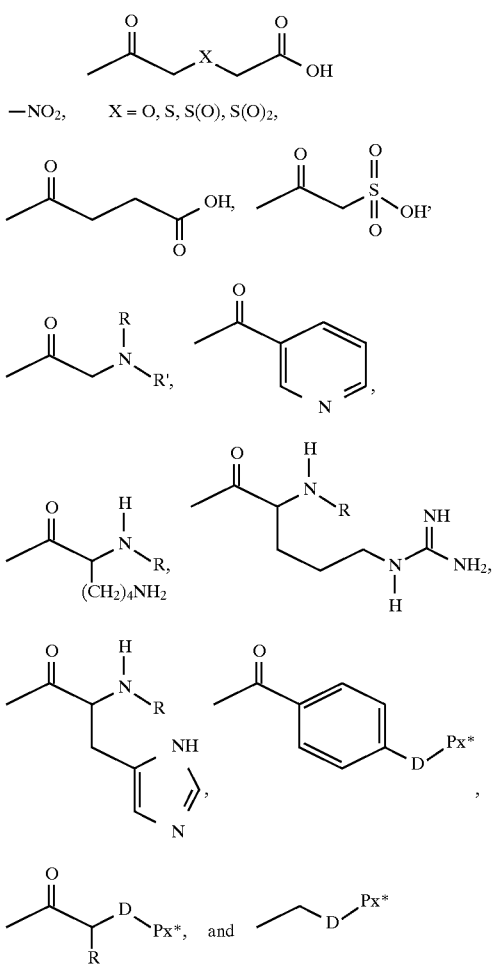
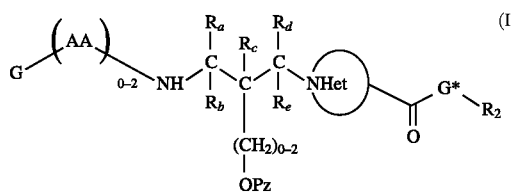
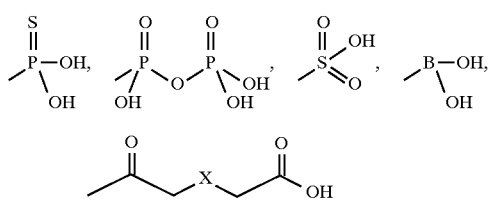

wherein R and R' are independently hydrogen or $C_1$–$C_4$ alkyl, D is O or S and Px* is as previously defined ;

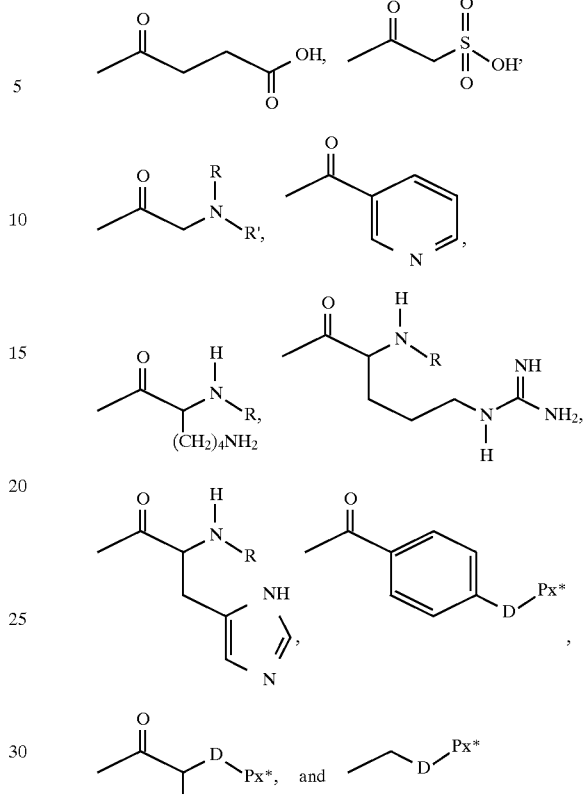

wherein G is $R_1$ or $R_{1*}$, G* is —O— or —$NR_f$— and Pz is selected from the group consisting of

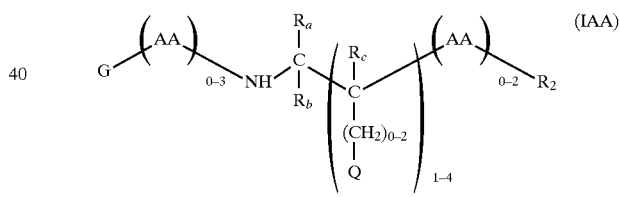

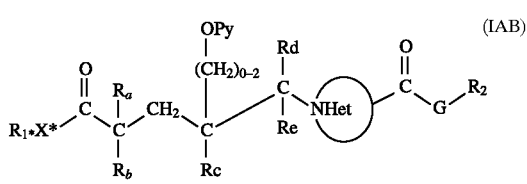

—$NO_2$, X = O, S, S(O), S(O)$_2$,

wherein R and R' are independently hydrogen or $C_1$–$C_4$ alkyl, D is O or S and Px* is as previously defined;

(IAA)

wherein G is $R_1$ or $R_{1*}$, and each Q is independently H, —OPz or —$NR_d$Pz, wherein each $P_z$ is independently hydrogen or Py, provided that at least one Pz is Py;

(IAB)

wherein

NHet is a saturated or unsaturated cyclic, bicyclic or fused nitrogen containing ring system and G is a bond or is —O— or —$NR_f$;

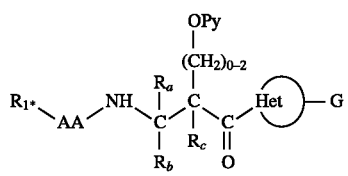
(IAC)

wherein G is absent or X*R$_{1*}$ and

is a 3 to 10-membered saturated or unsaturated heterocycle containing a nitrogen atom and optionally additionally one to three heteroatoms selected from nitrogen, oxygen and sulfur;

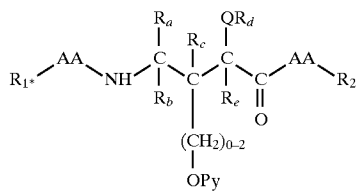
(IAD)

wherein Q is selected from —O—, —S— and —NR$_f$—;

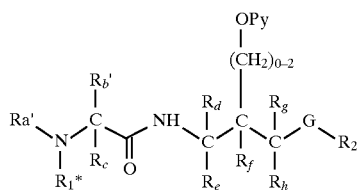
(IAE)

wherein G is O, S, S(O) or S(O)$_2$, and R$_a$' and R$_b$' have the meaning of R$_a$ and R$_b$ or R$_a$'. and R$_b$' together are trimethylene or tetramethylene;

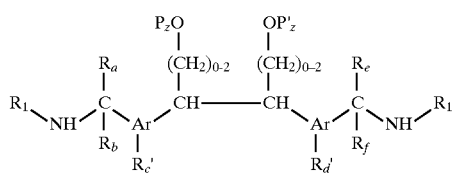
(1AF)

wherein each Ar is independently (C$_6$–C$_{14}$)aryl, R'$_c$ and R'$_d$ are R$_c$ and R$_d$ or, taken together, are —C(O)— or —CH(OH)—, and wherein Pz and Pz' are independently hydrogen or Py with the proviso that at least one of Pz and Pz' is Py, or Pz and Pz' together with the oxygen atoms to which they are attached form a group selected from

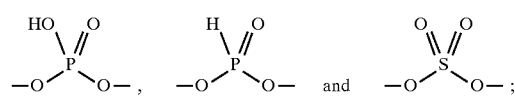

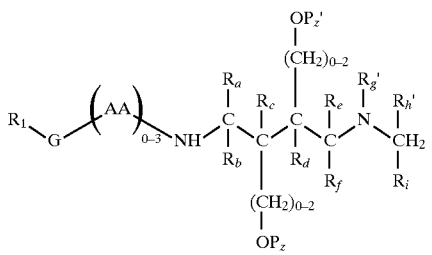
(IAG)

wherein G is a bond or X as previously defined, R$_g$' and R$_h$' are R$_g$ and R$_h$ or together form a saturated or unsaturated cylic, bicylic or fused ring system, and Pz and Pz' are independently hydrogen or Py with the proviso that at least one of Pz and Pz' is Py, or Pz and Pz' together with the oxygen atoms to which they are attached form a group selected from

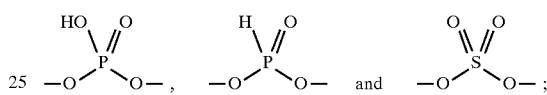

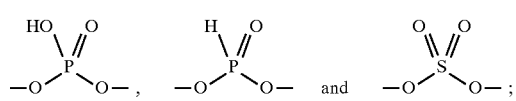
(IAH)

wherein G is a bond, O. S or NR$_j$, R$_g$' and R$_h$' are R$_g$ and R$_h$, or taken together may be —C(O)—, and Pz and Pz' are independently hydrogen or Py with the proviso that at least one of Pz and Pz' is Py, or Pz and Pz' together with the oxygen atoms to which they are attached form a group selected from

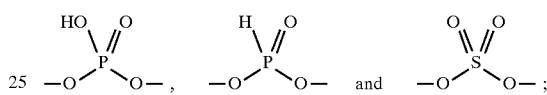

(IAI)

wherein G is OPy, NHR$_e$, NPyR$_e$ or R$_e$;

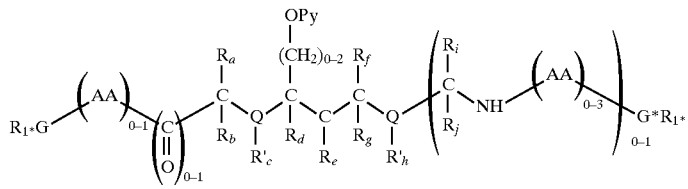
(IAJ)

wherein G and G* are independently a bond, O, S or NH, and R'$_d$ and R$_h$' are Rd and Rh or taken together are —CR'$_2$— or —CR$_2$'—CR$_2$'— wherein each R' independently has the meaning of R$_6$ as previously defined, Q and Q* are independently N or CR$_6$, or when Q* is CR$_6$ then R$_g$ and R$_6$ together may be a double bond;

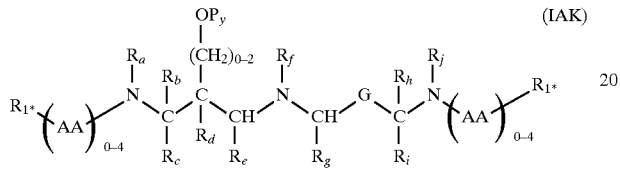
(IAK)

wherein G is —C(O)— or —C(R$_6$)(CH$_2$)$_{0-4}$OG* wherein G* is R$_6$ or Py;

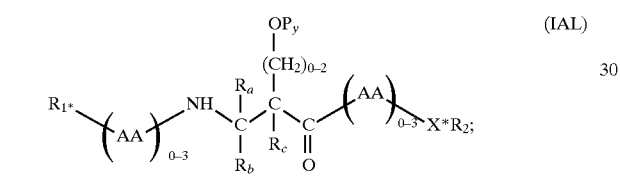
(IAL)

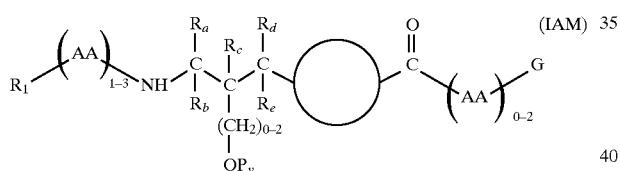
(IAM)

wherein G is selected from hydrogen and X*R$_{1*}$ and wherein

represents a 4–10 membered saturated or unsaturated cyclic, bicylic or fused ring system as defined herein;

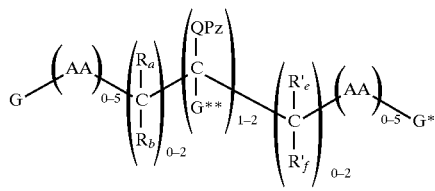
(IAN)

wherein Q is selected from O, S and NR$_g$, G and G* are independently selected from R$_1$, R$_{1*}$, —C(R$_5$)=NR$_3$ and —C(R$_5$)=NOR$_3$, wherein R$_3$ and R$_5$ are as previously defined, R'$_e$ and R'$_f$ are R$_e$ and R$_f$, and G** is R$_{20}$ as previously defined;

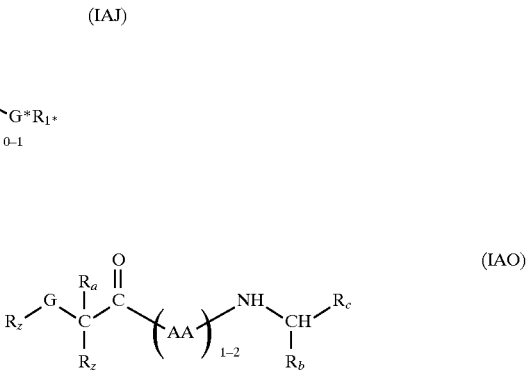
(IAO)

wherein each R$_z$ is independently selected from R$_1$ and PyOG* wherein G* is optionally substituted alkylelne, provided that at least one R$_z$ is PYOG*, and G is —NR$_d$— or CR$_d$R$_e$—;

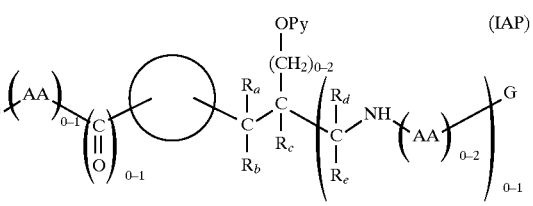
(IAP)

wherein

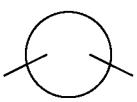

represents an optionally substituted saturated or unsaturated ring system optionally containing up to three heteroatoms selected from N, O and S, G is selected from R$_1$, XR$_1$ or X*R$_{1*}$ and R$_a$ and R$_b$ taken together may optionally be —C(O)—;

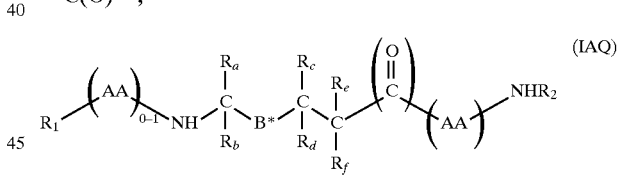
(IAQ)

wherein B* is a group B, as previously defined, derivatised with a solubilising group Py;

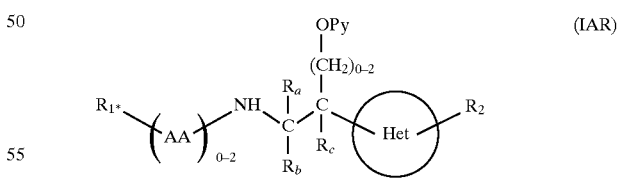
(IAR)

wherein

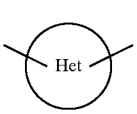

represents an optionally substituted cyclic, bicyclic or fused ring system containing a nitrogen atom and optionally additionally from 1 to 3 heteroatoms selected from N, O and S;

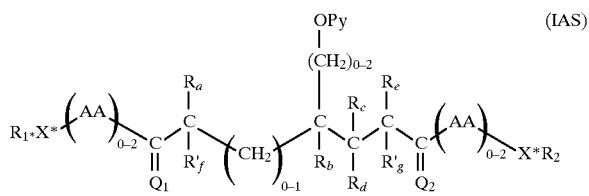

wherein $Q_1$ and $Q_2$ are independently selected from O and S, and $R'_f$ and $R'_g$ are respectively $R_f$ and $R_g$ or are selected from OR', SR' and $NR_hR'$ wherein R' is H, $R_i$ or Py;

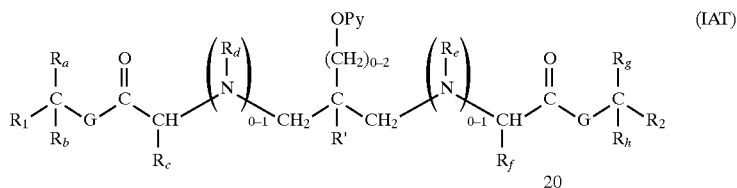

wherein each G is independently selected from O and $NR_i$, and R' is $(CH_2)_{1-2}OPy$ or $R_6$

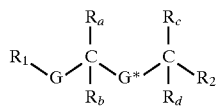

wherein G and G* are independently selected from

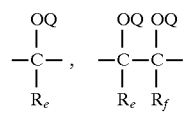

and L, wherein L is as previously defied and Q is H or Py, provided that at least one of G and G* is other than L and provided that at least one Q is Py, or wherein two groups OQ taken together are a cyclic group slected from

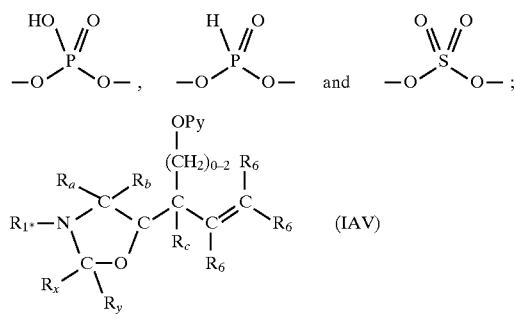

wherein $R_x$ and $R_y$ are independently $R_6$ or $(CH_2)_{1-2}OPy$;

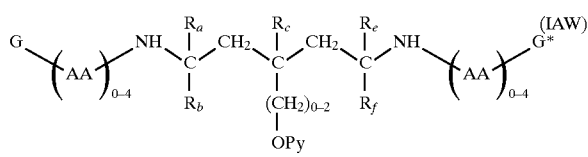

wherein G and G* are independently selected from $R_1$, $R_{1*}$, —$C(R_5)$=$NR_3$ and —$C(R_5)N$=$OR_3$, wherein $R_3$ and $R_5$ are as previously defined.

Still other compounds of the first embodiment are those compounds exemplified in International Patent Application no. WO 93/18006, namely:

(i) t-butyl 3-isopropyl-3-[(2R or S, 3S)-2-hydroxy-3-(phenylmethoxycarbonyl)-amino4-phenylbutyl] carbazate, (ii) t-butyl 3-isopropyl-3-[(2R or S, 3S)-2-hydroxy-3-(N-quinaldoyl-L-valyl)-amino4-phenylbutyl]carbazate, (iii) t-butyl 3-isopropyl-3-[(2R or S, 3S)-2-hydroxy-3-(N-quinaldoyl-L-asparaginyl)amino4-phenylbutyl]carbazate, (iv) t-butyl 3-(1-methyl-3-phenylpropen-3-yl)-3-[(2R or S, 3S)-2-hydroxy-3-(phenylmethoxycarbonyl)amino-4-phenylbutyl]carbazate, (v) t-butyl 3-(1-methyl-3-phenylpropyl)-3-[(2R or S, 3S)-2-hydroxy-3-(N-quialdoyl-L-asparaginyl)amino-4-phenylbutyl]carbazate, (vi) cis-1,6-3-t-butoxycarbonyl-4-[(2R or S, 3S)-2-hydroxy-3-amino4-phenylbutyl]-3,4-diazabicyclo[4.4.0]decane, (vii) cis-1,6-3-t-butoxycarbonyl4-[(2R or S, 3S)-2-hydroxy-3-(phenylmethoxycarbonyl)amino4-phenylbutyl]-diazabicyclo[4.4.0]decane, (viii) cis-1,6-3-t-butoxycarbonyl4-[(2R or S, 3S)-2-hydroxy-3-(N-quinaldoyl-L-valyl)amino4-phenylbutyl]-3,4-diazabicyclo[4.4.0]decane, (ix) cis-1,6-3-t-butoxycarbonyl4-[(2R or S, 3S)-2-hydroxy-3-[N-(2-pyridyl)-methoxycarbonyl)-L-valyl)amino4-phenylbutyl]-3,4-diaza-bicyclo[4.4.0]-decane, (x) cis-1,6-3-t-butoxycarbonyl4-[(2R or S, 3S)-2-hydroxy-3-(N-quinaldoyl-L-asparaginyl)amino4-phenylbutyl]-3,4-diazabicyclo[4.4.0]decane, (xi) cis-1,6-3-t-butoxycarbonyl4-[(2R or S, 3S)-2-hydroxy-3-(N-quinaldoyl-L-glutaminyl)amino4-phenylbutyl]-3,4-diazabicyclo[4.4.0]decane, (xii) cis-1,6-3-t-butoxycarbonyl4-[(2R or S, 3S)-2-hydroxy-3-(N-quinaldoyl-L-threonyl)amino4-phenylbutyl]-3,4-diazabicyclo[4.4.0]decane, (xiii) 2-t-butoxycarbonyl-3-[(2R or S, 3S)-2-hydroxy-3-(phenylmethoxycarbonyl)-amino4-phenylbutyl]-2,3-diazabicyclo[2.2.1]hept-5-ene, (xiv) 2-t-butoxycarbonyl-3-[(2R or S, 3S)-2-hydroxy-3-(phenylmethoxycarbonyl)-amino-4-phenylbutyl]-2,3-diaza-bicyclo[2.2.1]heptane, (xv) 2-t-butoxycarbonyl-3-[(2R or S, 3S)-2-hydroxy-3-(N-(2-pyridyl)methoxy-L-valyl)amino4-phenylbutyl]-2,3-diaza-bicyclo[2.2.1]heptane, (xvi) 2-[N-(1S)(2-methyl-1-methoxycarbonylpropyl) carbamoyl]-3-[(2R or S, 3S)-2-hydroxy-3-[N-(2-pyridyl) methoxy-L-valyl]amino-4-phenylbutyl]-2,3-diazabicyclo [2.2.1]heptane, (xvii) 2-t-butoxycarbonyl-3-[(2R or S, 3S)-2-hydroxy-3-(N-quinaldoyl-L-asparaginyl)amino4-phenylbutyl]-2,3-diazabicyclo[2.2.1]heptane, (xviii) 1-[2-(2-pyridyl)methoxycarbonylamino-]benzoyl-2-[ (2R or S, 3S)-2-hydroxy3-(N-quinaldoyl-L-asparaginyl) amino4-phenylbutyl]-2-isopropyl-hydrazine, (xix) 2-t-butoxycarbonyl-3-[(2R or S, 3S)-2-hydroxy-3-(N-quinaldoyl-L-asparaginyl)amino4-phenylbutyl]-1,2,3,4-tetrahydrophthalazine, (xx) 1-trimethylacetyl-2-[(2R or S, 3S)-2-hydroxy-3-(phenylmethoxycarbonyl)-amino4-phyenylbutyl]-2-isopropylhydrazine, (xxi) 1-trimethylacetyl-2-[(2R or S, 3S)-2-hydroxy-3-(N-quinaldoyl-L-asparaginyl) amino4-phenylbutyl]-2-isopropylhydrazine, (xxii) 1-(t-butylamino)carbonyl-2-[(2R or S, 3S)-2-hydroxy-3-(N-quinaldoyl-L-asparaginyl)amino4-phenylbutyl]-2-isopropylhydrazine, (xxiii) t-butyl 3-isopropyl-3-[(2R or S, 3S)-2-hydroxy-3-(N-picolinoyl-L-asparaginyl)amino4-phenylbutyl]carbazate, (xxiv) t-butyl 3-isopropyl-3-[(2R or S, 3S)-2-hydroxy-3-(N-(2-pyridyl)-methoxycarbonylanthraniloyl)amino4-phenylbutyl]carbazate.

(xxv) t-butyl 3-benzyl-3-[(2R or S, 3S)-2-hydroxy-3-(phenylmethoxycarbonyl)-amino4-phenylbutyl] carbazate, (xxvi) t-butyl 3-benzyl-3-[(2R or S, 3S)-2-hydroxy-3-(N-quinaldoyl-L-asparaginyl)-amino4-phenylbutyl] carbazate, (xxvii) t-butyl 3-cyclohexyl-3-[(2R or S, 3S)-2-hydroxy-3-(phenyl-methoxycarbonyl)amino4-phenylbutyl] carbazate, (xxviii) t-butyl 3-cyclohexyl-3-[(2R or S, 3S)-2-hydroxy-3-(N-quinaldoyl-L-asparaginyl)amino4-phenylbutyl] carbazate, (xxix) t-butyl 3-isopropyl-3-[(2R or S, 3S)-2-hydroxy-3-(N-(1-carbamoyl-methyl)-acryloyl)amino4-phenylbutyl] carbazate, (xxx) t-butyl 3-isopropyl-3-[(2R or S, 3S)-2-hydroxy-3-(N-(2(RS)-3-tert-butylthio2-carbamoyl-methylpropionyl) amino4-phenylbutyl]carbazate, (xxxi) t-butyl 3-isopropyl-3-[(2R or S, 3S)-2-hydroxy-3-(N-(1-benzoyl-L-asparaginyl)amino4-phenylbutyl] carbazate, (xxxii) 1-t-butyloxycarbonyl-2-[(2R or S, 3S)-2-hydroxy-3-(phenylmethoxycarbonyl)amino4-phenylbutyl] hexahydropyridazine, (xxxiii) 1-t-butyloxycarbonyl-2-[(2R or S, 3S)-2-hydroxy-3-(N-quinaldoyl-L-asparaginyl)amino4-phenylbutyl] hexahydropyridazine, and (xxxiv) cis-1,6-3-t-butoxycarbonyl4-[(2R or S, 3S)-2-hydroxy-3-(N-quinaldoyl-3-cyano-L-alanyl)amino4-phenylbutyl]-3 ,4-diaza-bicyclo[4,4,0]decane, wherein the 2-hydroxy group has been derivatised with a solubilising group Px as herein defined. Typically, in this form of the first embodiment, compounds (i) to (xxxiv) referred to above are derivatised with a solubilising group selected from

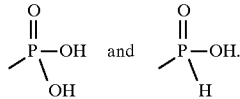

The compounds of formulae (I) to (IAW) can exist in optically isomeric forms and the present invention includes within its scope all these forms in all proportions including all diastereoisomers and mixtures thereof and all enantiomers, mixtures of enantiomers and racemic mixtures. Where a double bond occurs in the compound of the invention, the double bond may be present in the cis- (Z) or trans- (E) configuration. It will be understood that only compounds of formula (I) with combinations of substituents or functional groups which give rise to stable compounds, are within the scope of the present invention.

The compounds of general formula (I) may be prepared by methods known generally in the art. Suitable methods for the synthesis of compounds of formula (I) and intermediates thereof are described, for example, in Houben-Weyl, *Meth-oden der Organischen Chemie*; J. March, *Advanced Organic Chemistry*, 3rd Edition (John Wiley & Sons, New York, 1985); D. C. Liotta and M. Volmer, eds, *Organic Syntheses Reaction Guide* (John Wiley & Sons, Inc., New York, 1991); R. C. Larock, *Comprehensive Organic Transformations* (VCH, New York, 1989), H. O. House, *Modern Synthetic Reactions* 2nd Edition (W. A. Benjamin, Inc., Menlo Park, 1972); N. S. Simpkins, ed. 100 *Modern Reagents* (The Royal Society of Chemistry, London, 1989); A. H. Haines *Methods for the Oxidation of Organic Compounds* (Academic Press, London, 1988) and B. J. Wakefield *Organolithium Methods* (Academic Press, London, 1988).

For example, a compound of formula (I) may be prepared from synthons $W^*$, $\{(A)_n B\text{-}(A^*)_m\}^*$ and $V^*$, wherein each synthon identified thus * is a synthetic precursor of the corresponding portion of the molecule $W\text{—}(A)_n\text{—}B\text{—}(A^*)_m\text{—}V$. Thus, a compound of formula (I) may be prepared, for example, in any of the following ways:

(a) by reaction of $W\text{—}(A)_n\text{—}B\text{—}(A)_m\text{—}G$ with $H\text{—}V$;

(b) by reaction of $W\text{—}(A)_n\text{—}B\text{—}(A)_m\text{—}H$ with $G\text{—}V$;

(c) by reaction of $W\text{—}H$ with $G\text{—}(A)_n\text{—}B\text{—}(A)_m\text{—}V$; and (d) by reaction of $W\text{—}G$ with $H\text{—}(A)_n\text{—}B\text{—}(A)_m\text{—}V$;

wherein G is a leaving group such as halogen, typically chlorine, bromine or iodine; a sulfonate such as methanesulfonate, trifluoromethanesulfonate, benzenesulfonate or toluenesulfonate; an alkoxy, thioalkoxy, aryloxy or thioaryloxy group such as ethoxy, methoxy, thiomethoxy or phenoxy; acyloxy such as acetyl, trifluoroacetyl or benzoyl; hydroxy; amino or protonated amino; nitrate; phosphate; borate and the like. If appropriate these reactions may be carried out in the presence of a base such as triethylamine, pyridine or other tertiary amine, butyllithium, sodium tert-butoxide or similar, and/or a coupling reagent such as a carbodiimide.

When V is $YR_2$ where Y is $\text{—}N\text{=}N\text{—}$, or when V is $Y^*$ where $Y^*$ is a member of the group

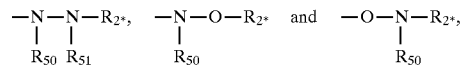

the compound of formula (I) may be prepared as shown in Scheme 1 or Scheme 1a. In the Schemes and in the Examples herein, the terms Me, Et, Pr, Ph and Bz signify methyl, ethyl, propyl, phenyl and benzyl respectively and the following additional abbreviations are used:

THP tetrahydropyranyl, t-Bu or But tertiary butyl n-Bu n-butyl iPr or Pr$^i$ isopropyl Hal halogen; i.e., fluorine, chlorine, bromine or iodine Ts para-toluenesulfonyl DMF dimethyl formamide CDI N,N'-carbonyldiimidazole BOP benzotriazol-1-yloxytris(dimethylamino)-phosphonium hexafluorophosphate HBT 1-hydroxybenzotriazole AcCN acetonitrile DMSO dimethyl sulfoxide Py.$xSO_3$ pyridine/sulfur trioxide complex QC quinoline-2-carbonyl PC 2-pyridinemethoxycarbonyl MC N-morpholinocarbonyl TMC N-thiomorpholinocarbonyl
Val valinyl
Asn asparaginyl
Ile isoleucyl
Gly glycinyl
Glu glutaminyl
Thr threonyl
Ala alanyl
(CN)Ala cyanoalanyl
(p-F)Bz 4-fluorobenzyl
(p-CN)Bz 4-cyanobenzyl
Z benzyloxycarbonyl
Boc t-butyloxycarbonyl
Ac acetyl
TFA trifluoroacetyl
$C_6H_{11}$ cyclohexyl.

metal carbonates and alkali metal hydroxides. The moiety W—$(A)_n$—B—$(A^*)_m$— may be represented by $R_a$, in which case $R_b$ represents $R_{50}$ as previously defined, and $R_c$ represents $R_2$ as previously defined, or W—$(A)_n$—B—$(A^*)_m$— may be represented by $R_c$, in which case $R_b$ represents $R_5$, and $R_a$ represents $R_2$.

When V is Y* where Y* is

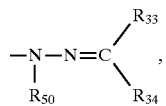

the compound of formula (I) may be prepared from by reacting a hydrazine wherein $R_{51}$ and $R_{2*}$ are both hydrogen, which may be prepared as shown in Scheme 1 or Scheme 1a, with an aldehyde or ketone.

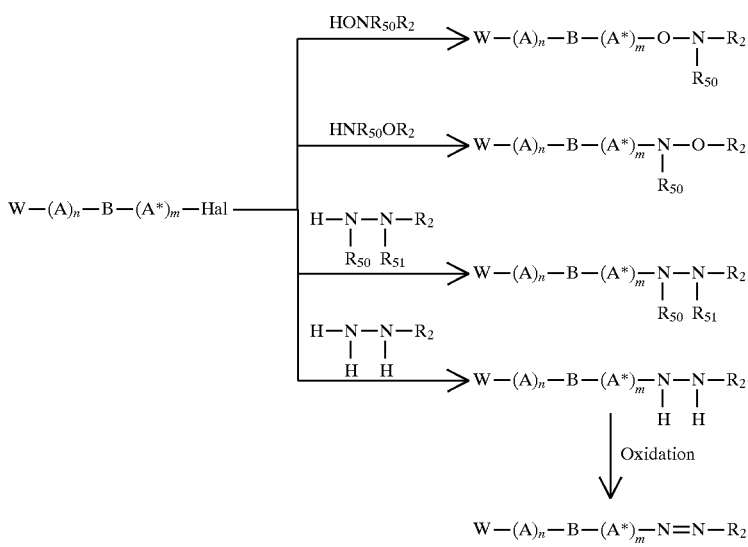

Other compounds of formula (I) may be prepared analogously, by reacting a synthon W—$(A)_n$—B—$(A^*)_m$—Hal with HV, if appropriate in the presence of a strong base.

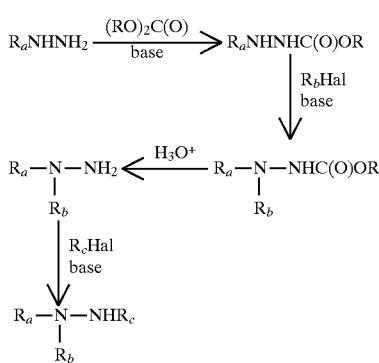

In Scheme 1a, R represents an alkyl, aryl or aralkyl group, such as t-butyl, phenyl or benzyl. Suitable bases include pyridine, triethylamine and other tertiary amines, alkali When V is $YR_2$ where Y is the compound of formula

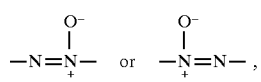

(I) may be prepared as shown in Scheme 1b Scheme 1b

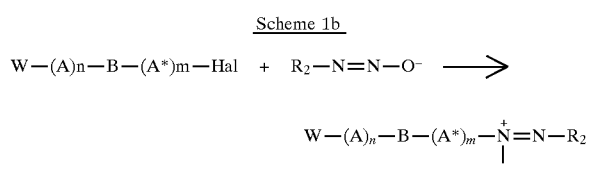

Scheme 1b -continued
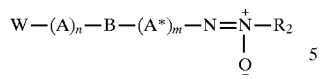
When V is YR$_2$ where Y is a member of the group
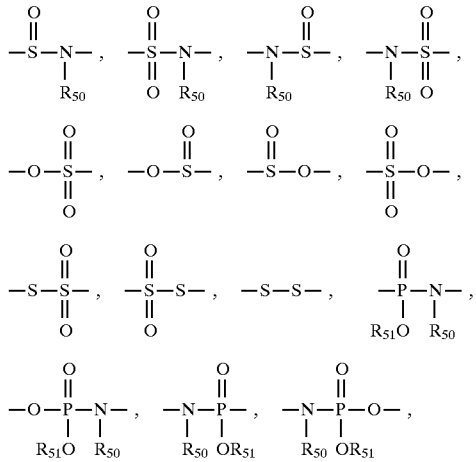
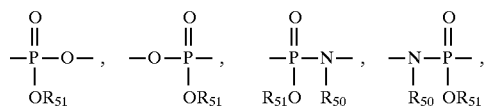
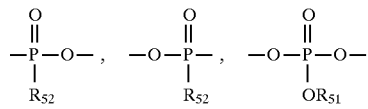
and
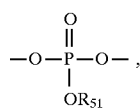
the compound of formula (I) may be synthesised by coupling a synthon W—(A)$_n$—B—(A*)$_m$—Z$_a$ with a synthon Z$_b$, where Z$_a$ includes one of the heteroatoms of Y, and Z$_b$ includes the other heteroatom or atoms, as shown in schemes 2a and 2b:
Scheme 2a
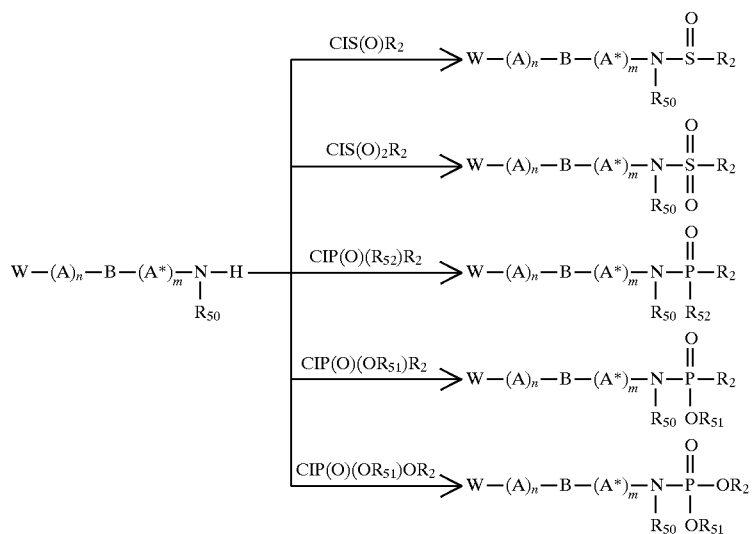

-continued
Scheme 2a
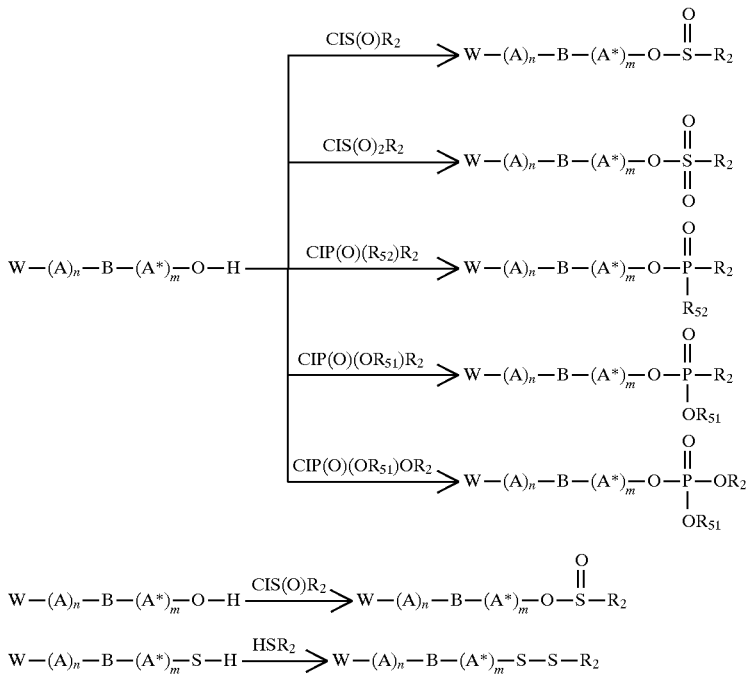
Scheme 2b
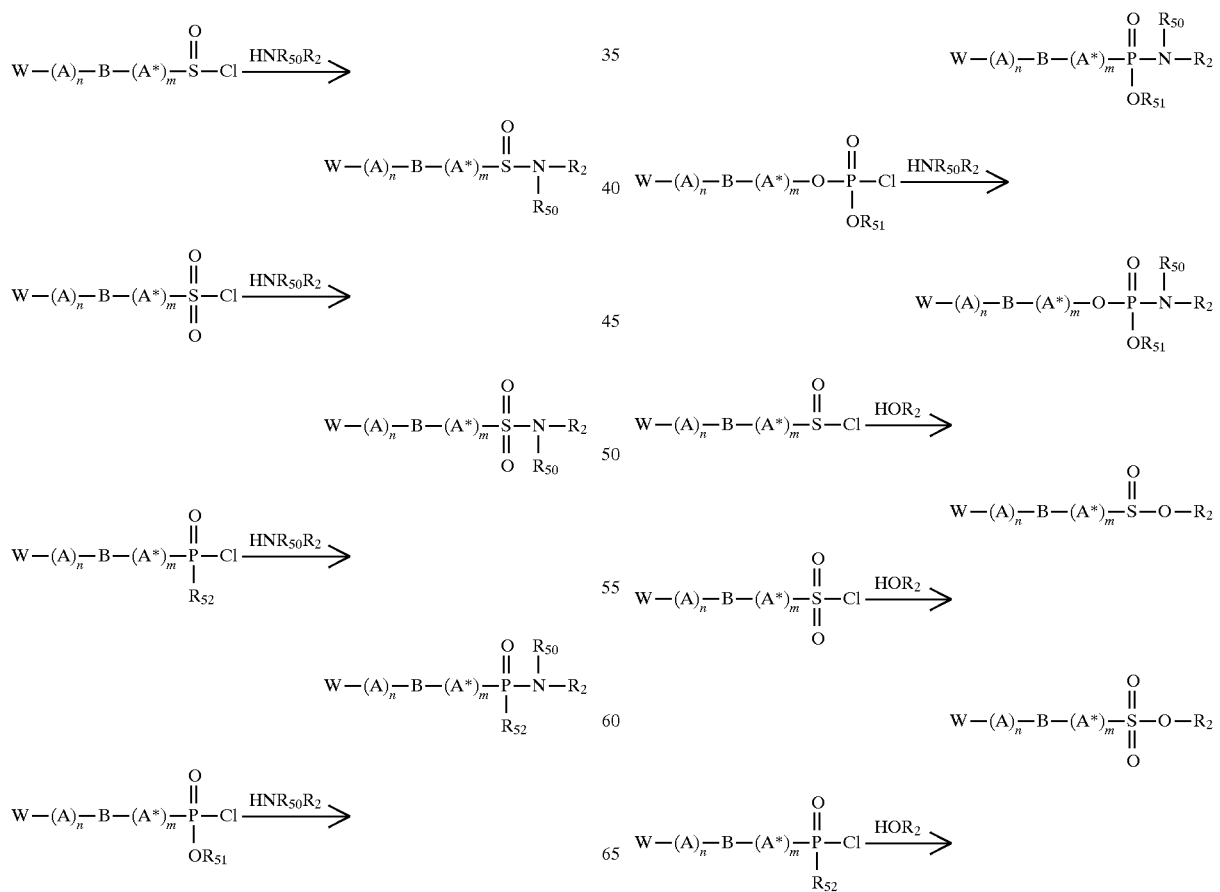

-continued
Scheme 2b

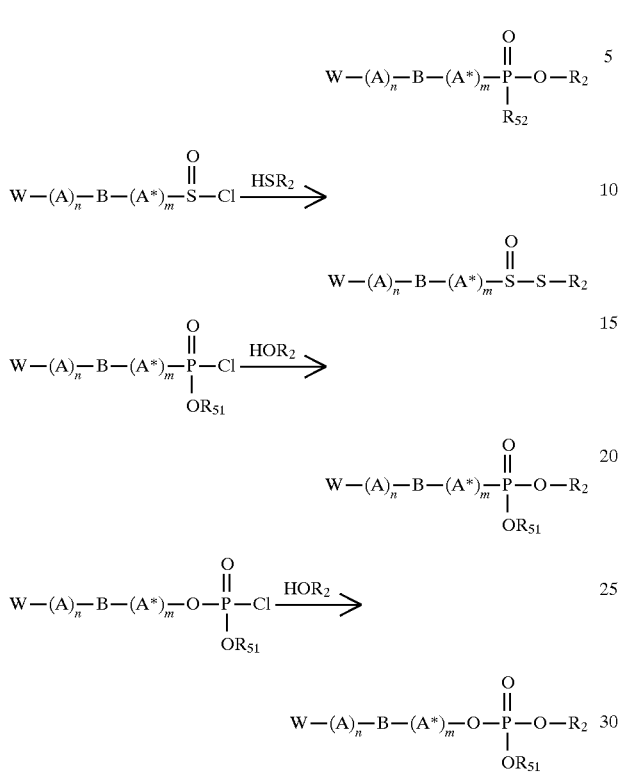

Analogous methods may be used to obtain the corresponding thionophosphates and thionophosphonates.

When V is $C(R_{30})=Y^{}$ the compound of formula (I) may be prepared from a synthon having a ketone or aldehyde function, by condensation with a substituted hydrazine or substituted hydroxylamine corresponding to $Y^{}$.

When V is $Y^*$, where $Y^*$ is $-N=O$, the compound of formula (I) may be prepared by oxidising the corresponding primary amine, for example with Caro's acid, or $H_2O_2$ in acetic acid, or $H_2O_2$ with sodium tungstate. It will be appreciated that a compound of formula (I) wherein $Y^*$ is $-N=O$ will only be isolable as a nitroso compound when the carbon atom bearing $Y^*$ has no α-hydrogens.

When V is $Y^*$, where $Y^*$ is

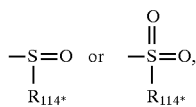

the compound of formula (I) may be prepared by oxidation of the corresponding thioether $$W-(A)_n-B-(A^*)_m-S-R_{114}. \qquad (IV)$$

with hydrogen peroxide and acetic acid. The thioether (IV) may be synthesised by coupling a halide $W-(A)_n-B-(A^*)_m-Hal$ with a thiol $R_{114^*}$ under basic conditions, or by reacting a disulfide $R_{114^*}SSR_{114^*}$ with an organolithium reagent $W-(A)_n-B-(A^*)_m-Li$ derived from the corresponding halide.

When V is $Y^*$, where $Y^*$ is

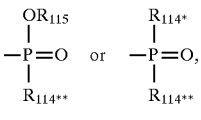

the compound of formula
(I) may be prepared by the Arbuzov reaction as shown in scheme 3:

Scheme 3

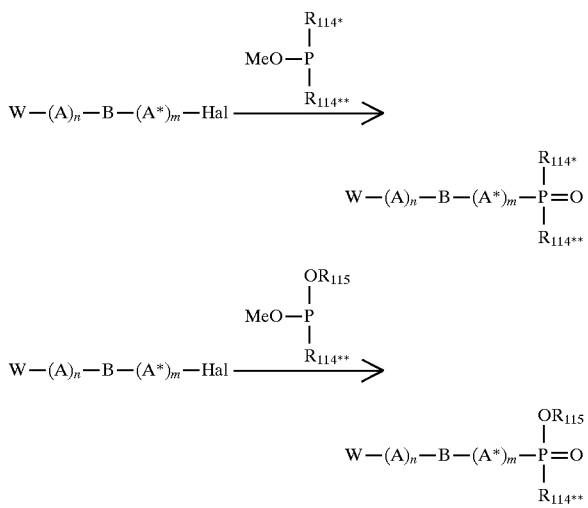

The synthon $W-(A)_n-B-(A^*)_m-Z$, where Z is any of the functional groups bound to $(A^*)_m$ which are represented in schemes 1 to 3, may be prepared by coupling a suitably functionalised fragment $W^*$ with a correspondingly functionalised fragment $Z^*-(A)_n-B-(A^*)_m-Z$. Alternatively, the compound of formula (I) may be synthesised by first coupling V to $(A)_{-n}-B-(A^*)_m-$ as described above with reference to schemes 1 to 3, and then coupling the resulting molecule to a functionalised fragment $W^*$. Methods for coupling a precursor of group W with a functionalised fragment $Z^*-(A)_n-B-(A^*)_m-Z$ are well known in the art, and include methods analogous to those represented in schemes 1 to 3. For example, when W is $R_1X$ and X is Y, the coupling may be achieved as described in schemes 1 to 3 above. When W is $R_1X$ and X is $NR_{10}$, O or S, the coupling may be achieved by any of the known methods for the alkylation of amines, and the synthesis of ethers and thioethers, respectively. That is, the coupling may be achieved by reacting a fragment $Z^*-(A)_n-B-(A^*)_m-Z$ wherein $Z^*$ is a leaving group such as halogen, sulfonate ester, acetate or trialkylammonium salt, with $R_1R_{10}NH$, $R_1OH$ or $R_1SH$, if necessary in the presence of strong non-nucleophilic base such as butyllithium, sodamide or potassium tert-butoxide. Compounds in which X is S(O) or $S(O)_2$ may be prepared by the oxidation of the corresponding compound in which X is S. Compounds in which W is $-CN$, $-C(R_5)=NR_3$, $-C(R_5)=NOR_3$, $-C(D)OR_3$, $-C(D)SR_3$ or $-C(D)NR_3R_4$ may be prepared from the fragment $Z^*-(A)_n-B-(A^*)_m-Z$ wherein $Z^*$ is an aldehyde, ketone or carboxyl group as shown in Scheme 3a.

Scheme 3a

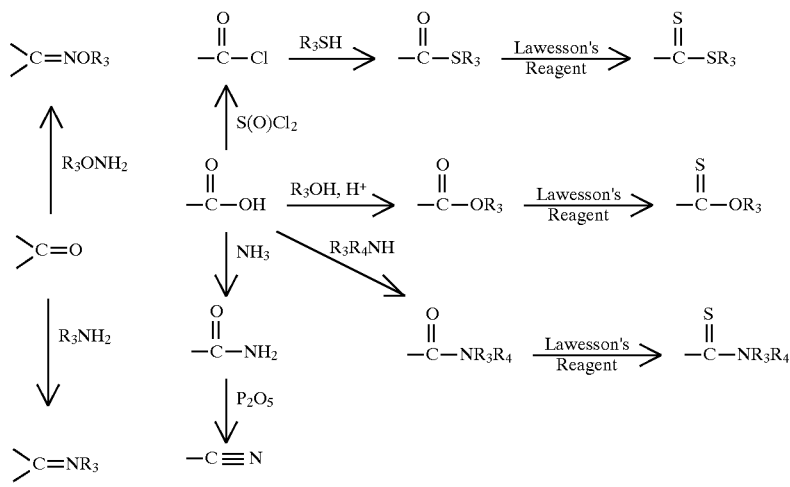

Compounds in which W is $-N=CR_5R_{5*}$ may be prepared by reacting the fragment $Z^*-(A)_n-B-(A^*)_m-Z$, where $Z^*$ is $NH_2$, with an aldehyde or ketone having group(s) $R_5$ and $R_{5*}$ bound to the carbonyl.

The fragment $Z^*-(A)_n-B-(A^*)_m-Z$ may be prepared by methods which depend on the nature of B. Where B is a substituted carbon atom, the fragment may be conveniently prepared from a fragment $E-C(O)-E^*$, in which E is a fragment $Z^*-(A)_n$ and $E^*$ is a fragment $(A^*)_m-Z$, as shown in scheme 4:

Scheme 4

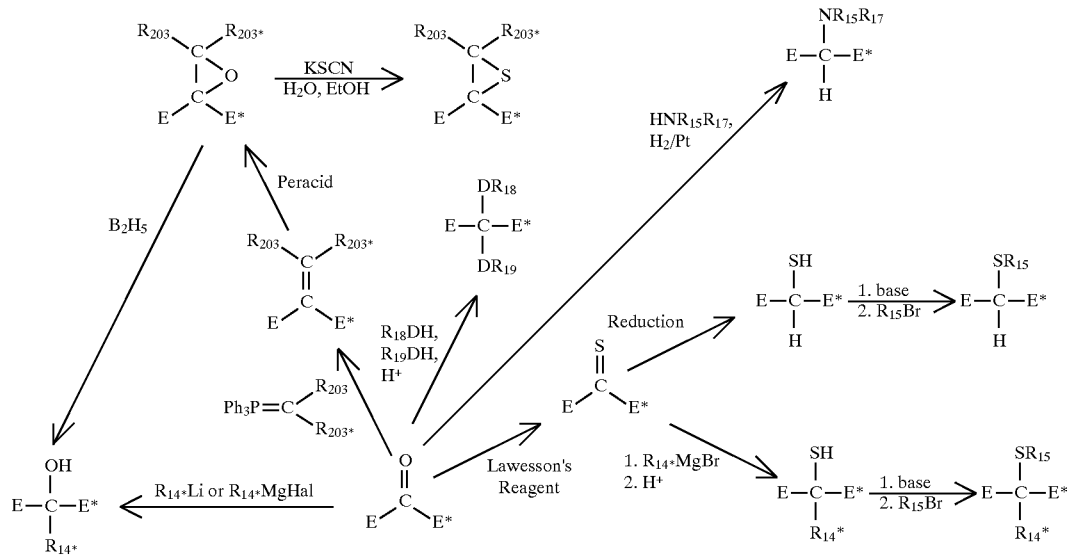

-continued
Scheme 4

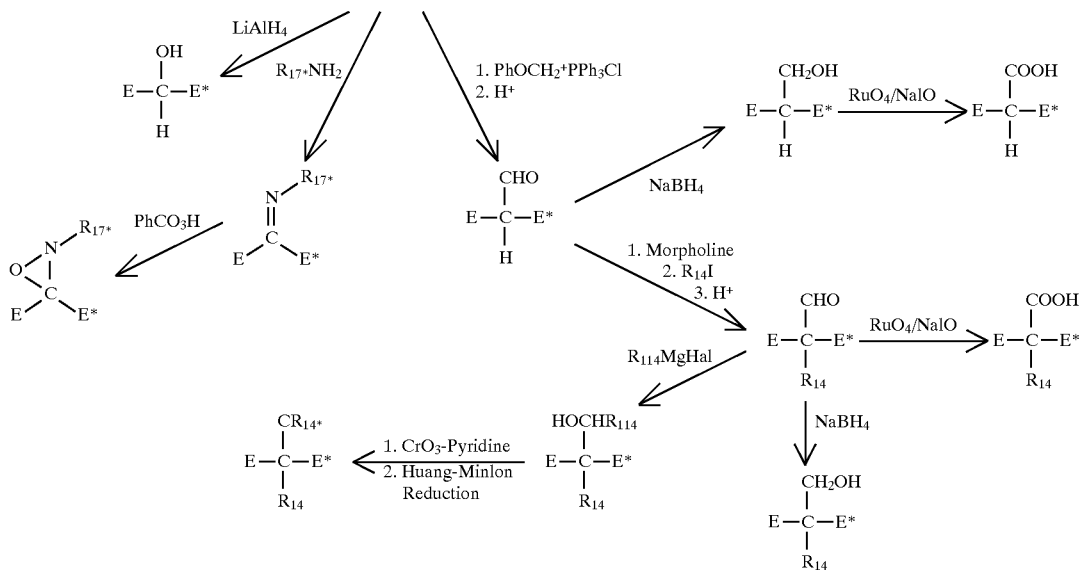

Fragments

which are starting materials for compounds of formula (I) are known compounds or analogs of known compounds which can be prepared by methods analogous to methods used for preparation of the known compounds. The synthesis of known fragments

may be found with reference, for example, to Beilsteins Handbuch der Organischen Chemie or to J. Buckingham, ed., *Dictionary of Organic Compounds* 5th Edition (Chapman & Hall, New York, 1982). Alternatively, a functionalised group E may be coupled to a group E*C(O)H, or a functionalised group E* may be coupled to a group EC(O)H, followed by oxidation. For example, a halide EBr may be coupled to E*C(O)H with an organolithium or organomagnesium reagent derived from EBr, followed by oxidation of the resulting secondary alcohol to the corresponding ketone, if desired. Alternatively a carboxylic acid EC(O)OH may be converted to an activated derivative, such as an ester or amide: for example an amide obtained by reaction of the carboxylic acid with N,O-imethyl hydroxylamine hydrochloride in the presence of a carbodiimide and tertiary base, followed by addition of an organolithium or organomagnesium reagent derived from E*Br, E*Cl or E*I.

When B is an epoxide of the type

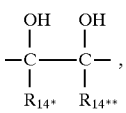

the fragment E—B—E* may be prepared from the corresponding olefin by reaction with a per-acid such as trifluoroperacetic acid, perbenzoic acid or m-chloroperbenzoic acid. Suitable olefins for conversion to the fragment E—B—E* are commercially available or may be synthesised by known methods, for example by means of the Wittig reaction or by an elimination reaction of an alcohol, alcohol sulfonate, ester, halide or the like.

When B is a diol of the type $$\begin{array}{cc} OH & OH \\ | & | \\ -C\!\!-\!\!-\!\!C\!\!-\!\!, \\ | & | \\ R_{14^*} & R_{14^{**}} \end{array}$$

the compound of formula (I) may conveniently be prepared by reductive coupling of aldehydes EC(O)H and E*C(O)H as described in *J. Org. Chem SS*, 4506 (1990) and U.S. Pat. No. 5,294,720.

When B is a heteroatom or substituted heteroatom, the fragment Z*—(A)$_n$—B—(A*)$_m$—Z is a substituted amine, phosphine or phosphine oxide, or is an ether, thioether, sulfoxide or sulfone. Substituted amines, ethers, thioethers, sulfoxides and sulfones may be prepared as described above. Secondary or tertiary phosphines may be prepared by alkylation of the corresponding primary or secondary phosphine as described, for example, in J. D. Roberts and M. C. Caserio, *Basic Principles of Organic Chemistry* (W. A. Benjamin, Inc., New York, 1965).

In any of the reactions described above, it may be necessary to protect reactive group(s) in the compound of formula (I) other than those participating in a desired coupling or oxidation reaction using suitable protecting group(s) in order to carry out the desired coupling or oxidation reaction without chemically affecting those reactive groups. Suitable protecting groups for this purpose are described in the works of Greene and McOmie referenced above.

The compounds of formula (IB) wherein x and y are both 1 may be prepared as generally described above. A compound of formula (IB) which is

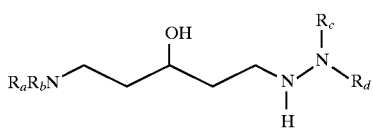

where $R_a$ and $R_b$ have the meaning of $R_{50}$, and $R_{506}$ as previously defined and $R_c$ and $R_d$ have the meaning of $R_{551}$ and $R_{502}$ as previously defined, may be prepared from ethylene cyanohydrin by the method shown in Scheme 5.

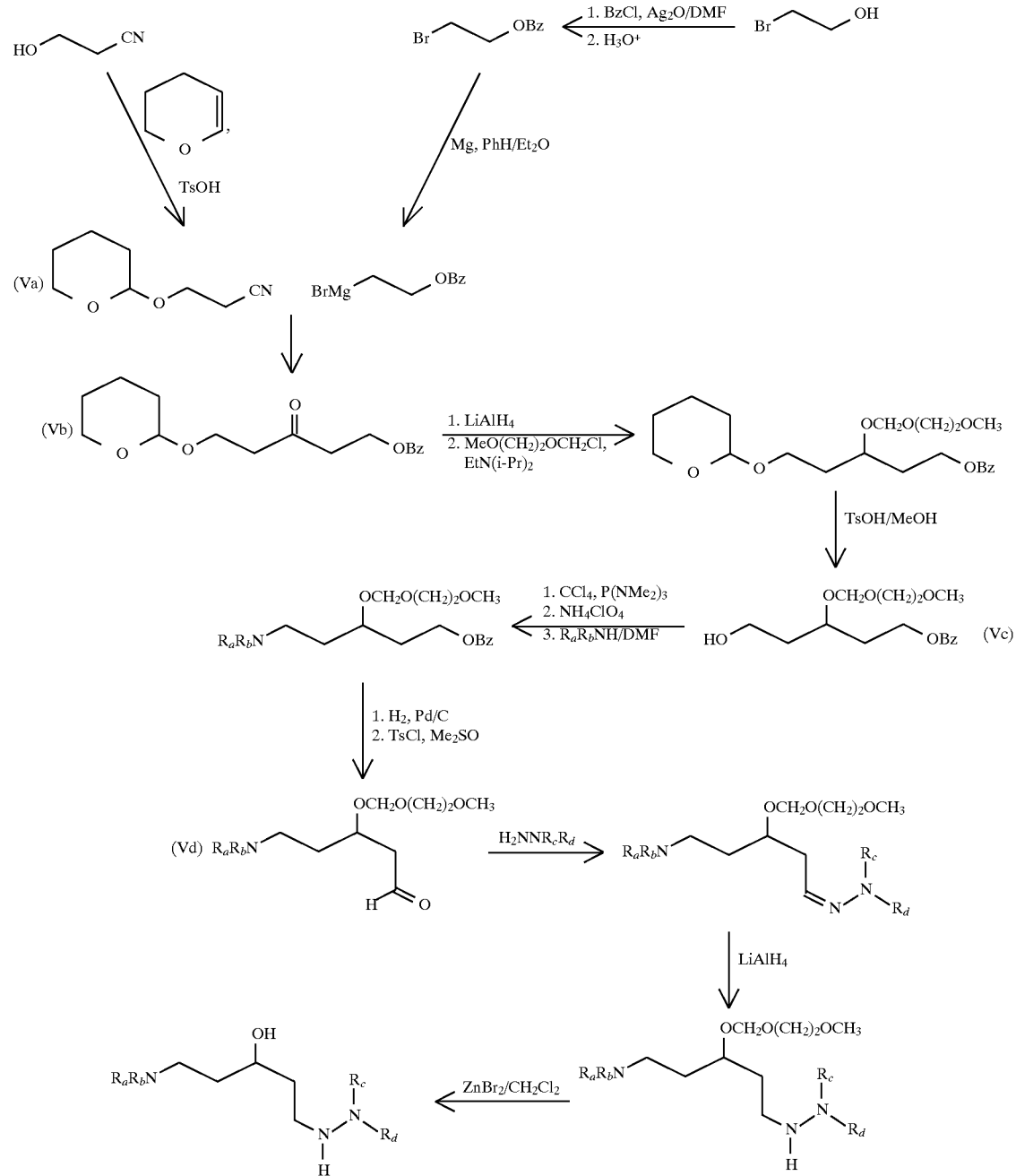

A substituted compound of formula (IB) may be prepared by the general method of Scheme 5, with the substituents $R_{512}$, $R_{513}$, $R_{522}$, $R_{523}$, $R_{532}$, $R_{533}$, $R_{542}$, $R_{543}$ and $R_{550}$ being introduced, as desired, into the compounds of formula (Va), (Vb), (Vc) and (Vd) shown in Scheme 5 by the methods illustrated in Scheme 5a.

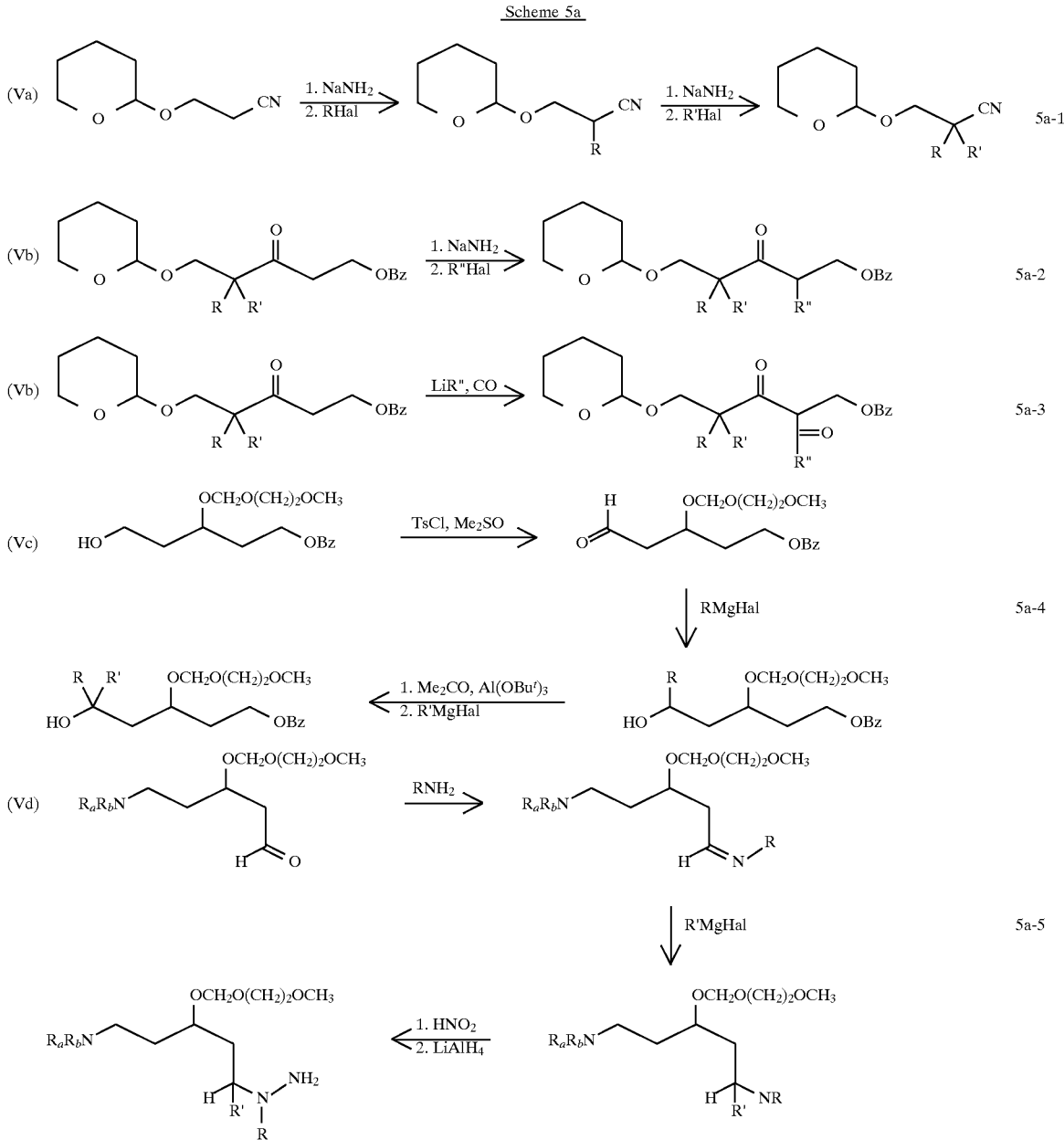

In reaction 5a-1 shown above, it will be appreciated that the step of introducing the second substituent R' will only be carried out if it is desired that both $R_{522}$ and $R_{523}$ be other than hydrogen. The reactions shown in 5a-2 and 5a-3 may be repeated, if desired, so as to introduce a second substituent on the carbon atom bearing R" or R"C(O). The second substituent can be the same as or different from the first. Where one or both of $R_{522}$ and $R_{523}$ is acyl, this group may be introduced as shown in reaction 5a-3 with respect to compound (Vb). Where $R_{522}$ and $R_{523}$ are both hydrogen, the reactions shown in 5a-2 and 5a-3 may give mixtures of products and in that case it may be preferable to introduce the desired groups $R_{532}$, $R_{543}$, $R_{542}$ and $R_{543}$ by replacing the ethylene bromohydrin shown in Scheme 5 with a suitably substituted bromohydrin obtained from the corresponding olefin as shown in Scheme 5b. It will be appreciated that the nature of the groups $R_{532}$, $R_{543}$, $R_{542}$ and $R_{543}$ will determine the stereochemistry of the addition of HOBr to the olefin and of the opening of the epoxide.

Scheme 5b

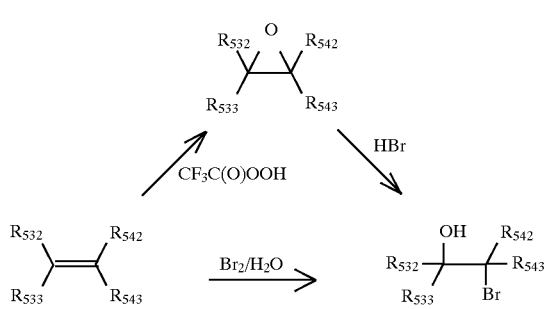

Compounds of formula (IB) wherein B is other than —CH(OH)— may be prepared by the methods shown in Scheme 4 after oxidation of the secondary alcohol to the corresponding ketone.

The compounds of formula (IB) wherein B is a substituted carbon atom and y is 0 can be prepared by reacting a compound of formula (II), (IIA) or (IIB)

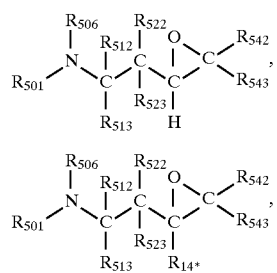

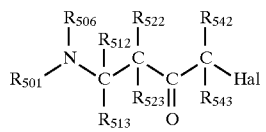

wherein $R_{14^*}$, $R_{501}$, $R_{502}$, $R_{506}$, $R_{512}$, $R_{513}$, $R_{522}$, $R_{523}$, $R_{542}$ and $R_{543}$ have the significance given earlier and Hal is a group selected from —Cl, —Br or —I, with a compound of formula (III)

wherein $R_{502}$, $R_{550}$ and $R_{55}$, have the significance given earlier. Where a compound of formula (II) is used, the reaction may be followed by oxidation of the resultant secondary alcohol to the corresponding ketone. This ketone may be used for elaboration of the substituents on B as shown in Scheme 4.

A compound of formula (II), (IIA) or (IIB) may be prepared from a β-amino acid or a β-amido acid as shown in Scheme 6. A compound of formula III may be prepared as shown in Scheme 1a.

Scheme 6

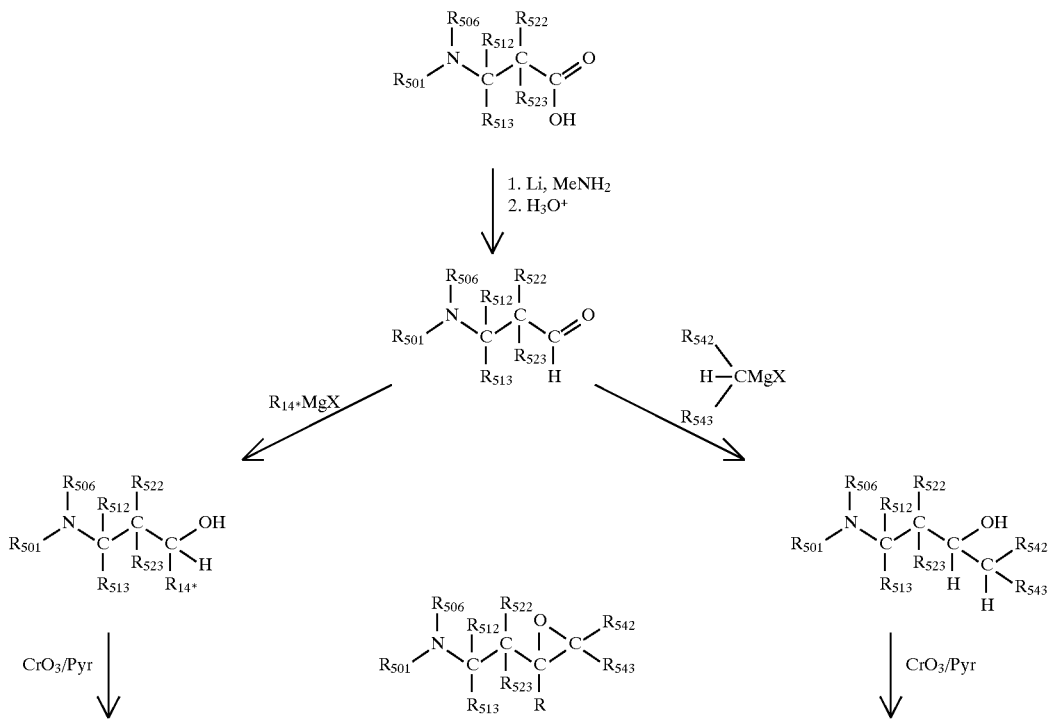

-continued
Scheme 6

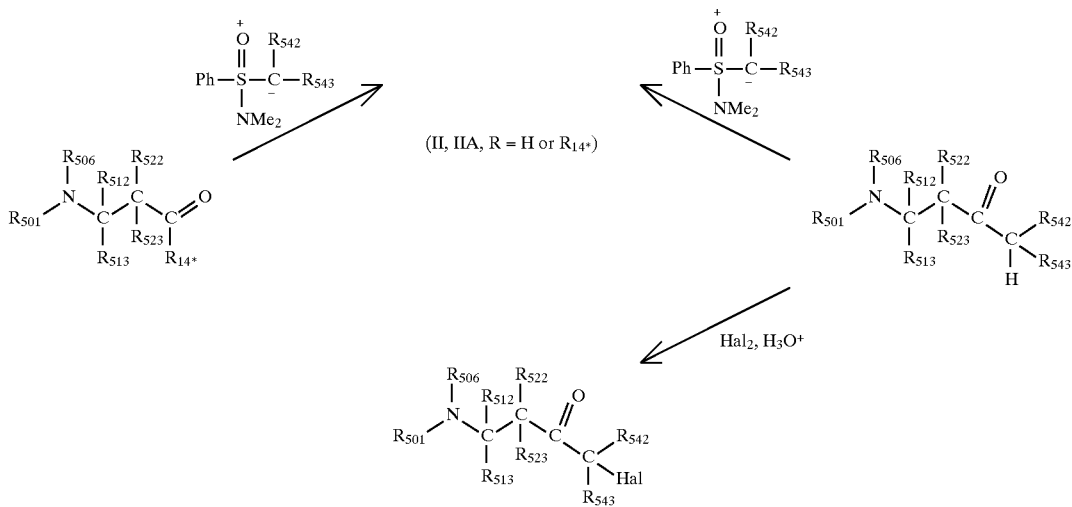

An alternative route to the β-aminoaldehyde shown in Scheme 6 is by reduction of the methyl ester of the corresponding β-amino acids using diisobutylaluminium hydride.

β-amino acids, or β-amido acids, may conveniently be prepared by the Mannich reaction of an amine or amide with an enolisable ketone in the presence of formaldehyde or another aldehyde.

A compound of formula (IB) wherein x and y are both 0 may be prepared by reacting a compound of formula (IIC) or (IID)

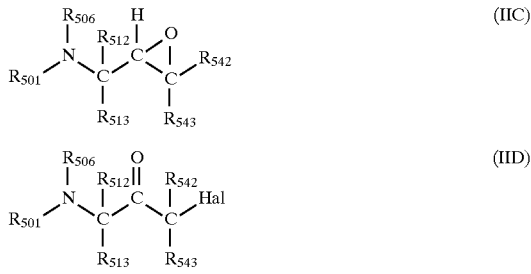

with a compound of formula (III) as shown above. An analogous procedure, utilising a primary or secondary amine rather than a hydrazine as shown in formula (II) yields a hydroxy diamine. A compound of formula (IIC) may be prepared from an α-amino acid by a method analogous to that shown in Scheme 6, such as described in the following:

Evans, B. E., et al., *J. Org. Chem.,* 50, 4615–4625 (1985);

Luly, J. R., et al., *J. Org. Chem.,* 52, 1487–1492 (1987);

Handa, B. K., et al., European Patent Application No. 346,847-A2 (1989) and

Marshall, G. R., et al., International Patent Application No W091/08221.

Suitable α-amino acids may be prepared, for example, by the Strecker synthesis, starting from an appropriate ketone. The overall route to the compound of formula (IIC) is shown in Scheme 7. Other suitable methods are described in Coppola, et al. *Asymmetric Synthesis. Construction of Chiral Molecules using Amino Acids* (Wiley Interscience, New York, 1987).

Scheme 7

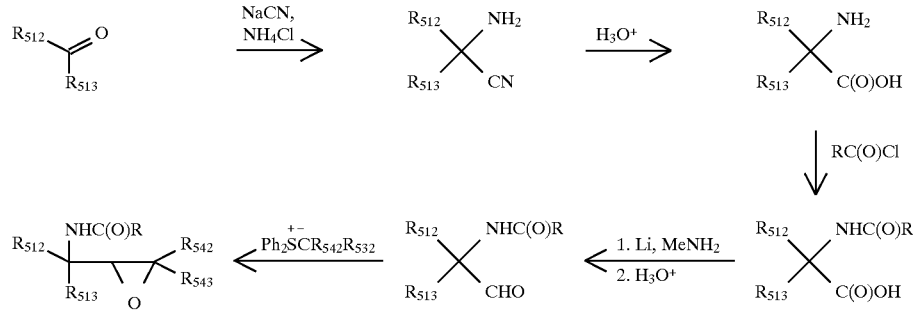

Where W is a nitrogen-containing group, and one of $R_1$ and $R_{10}$ is a protected amino acid residue, the coupling of the protected amino acid residue may be accomplished as shown in Scheme 8, in which the amino acid (designated AA) protecting group is benzyloxycarbonyl, designated Z. Methods for the formation of peptide bonds and for the protection of peptide residues are described, for example, in Gross and Meienhofer, eds., *The Peptides*, (Academic Press, New York, 1983). Suitable other coupling agents include 1-(3-dimethylaminopropyl)-3-ethylcarbodiimide hydrochloride (EDC) and diphenylphosphoryl azide (DPPA).

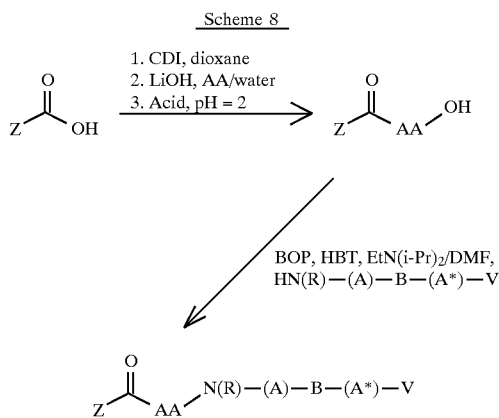

Numerous synthetic routes exist to substituted hydrazines, including the hydrazines of formula (III), useful in the synthesis of compounds of formula (I). The hydrazine intermediates (III) can be obtained using known methods such as those described in the following:

Dutta, A. S., et al., *J. Chem. Soc. Perkin Trans. I*, (1975) 1712–1720,

Ghali, N. I., et al., J. Org. Chem., 46, 5413–5414 (1981), Gante, J., Synthesis (1989) 405–413 and Houben-Weyl's *Methoden der Organische Chemie*, vol. 16a, Part 1, pp 421–855; Georg Thieme Verlag, Stuttgart (1990)

Other methods for preparing substituted hydrazines are illustrated in Scheme 9.

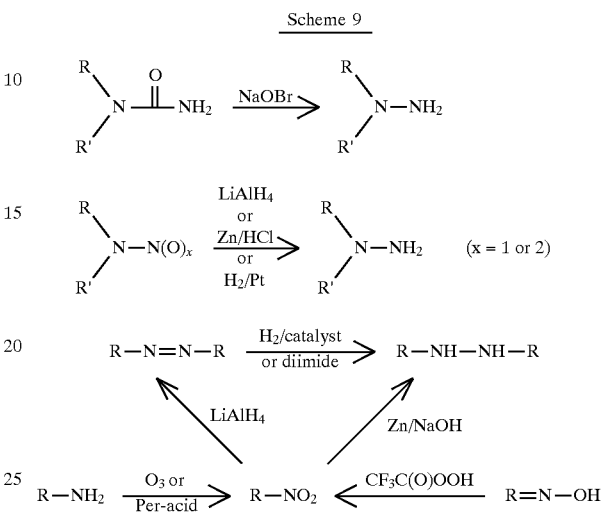

Compounds of formula (I) wherein a group selected from $R_1$, $R_{1*}$, $R_2$, $R_{2*}$, $R_9$, $R_{11}$, $R_{12}$, $R_{50}$ and $R_{51}$, together with another group selected from $R_1$, $R_{1*}$, $R_2$, $R_{2*}$, $R_{9*}$, $R_{10}$, $R_{11}$, $R_{12}$, $R_{50}$ and $R_{51}$ forms a cyclic, bicyclic or fused ring system may be prepared by variants on the above methods which will be readily apparent to persons skilled in the art in the light of the foregoing.

An example of a method of preparing one class of cyclic compounds of formula (I) is presented in Scheme 10:

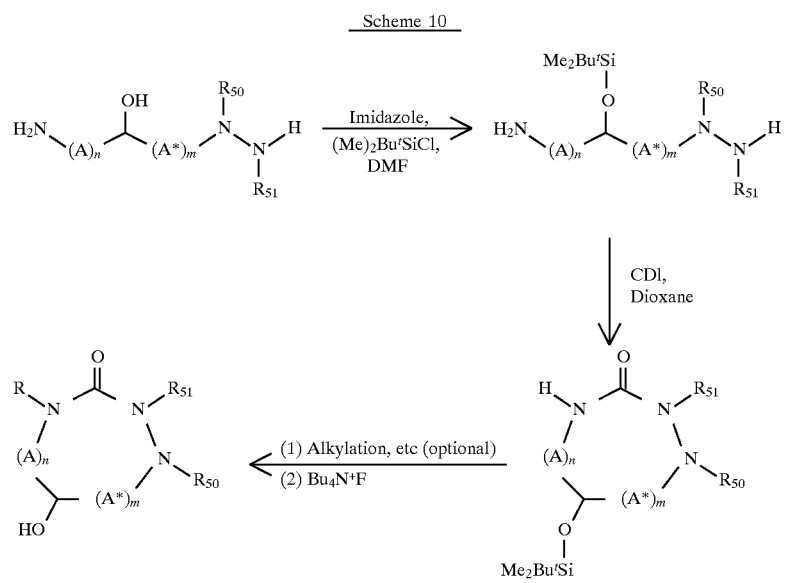

Compounds in accordance with the present invention which do not include a solubilising group Px typically exhibit low to very low water solubility. Inhibitors of HIV proteases which have hitherto been described, and many other pharmaceutically or veterinarily active substances also typically exhibit low to very low water solubility. This property tends to cause the bioavailability of such substances to be relatively low. There is thus a need for a HIV protease inhibitor having enhanced water solubility. Surprisingly, it has been found that the inclusion of a solubilising group Px as defined herein in a substance having low to very low water solubility results in enhancement of the water solubility of the substance. Thus, substances in accordance with the invention which include a solubilising group Px exhibit superior bioavailability, including superior oral bioavailability, compared to compounds in accordance with the invention which do not include a solubilising group Px.

Thus, according to a second embodiment of the present invention, there is provided process for enhancing the water-solubility of a pharmaceutical or veterinary substance, comprising derivatising a functional group of said substance with a solubilising group Px, wherein Px is selected from the group consisting of Px*,

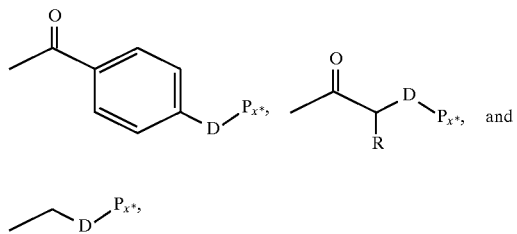

wherein D is 0 or S, R is H or $C_1$-$C_4$ alkyl, and wherein Px* is selected from:

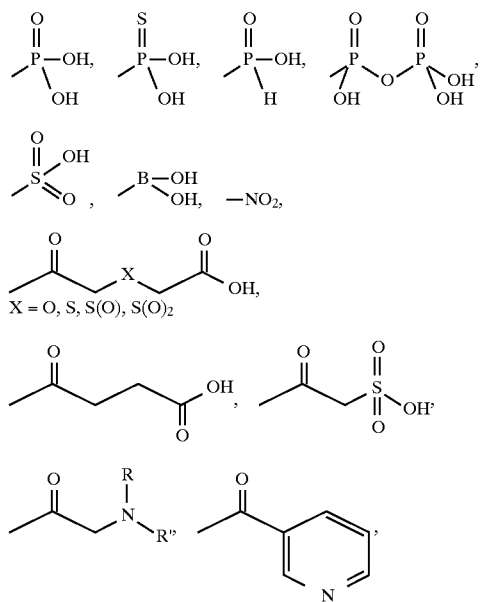

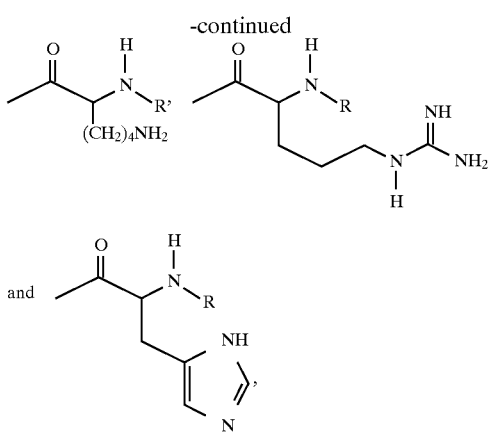

said functional group being capable of being derivatised with said solubilising group Px.

Generally, a compound according to the first embodiment includes at least one solubilising group Px as defined above. More generally, a solubilising group in a compound of the first embodiment or in the method of the second embodiment is selected from

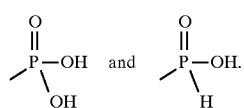

Typically, a solubilising group is introduced into the molecule as the last stage of its synthesis. For example, a solubilising group $P(O)(OH)_2$ may be introduced to a free amino, hydroxy or mercapto group by reaction of the amino, hydroxy or mercapto group with dimethyl chlorophosphate, followed by mild hydrolysis to remove the methyl ester groups. Other solubilising groups referred to above may be introduced by analogous methods: that is, by reaction of an amino, hydroxy, mercapto or other group capable of being derivatised with a solubilising group, with a reagent PxX', suitably protected if necessary (for example as methyl or benzyl esters), wherein Px is as defined above and X' is a leaving group such as Cl, Br, OH, $OS(O)_2R$ and the like, where R is $C_1$–$C_6$ alkyl, for example methyl, $C_6$–$C_{10}$ aryl, for example phenyl or 4-methylphenyl, or $C_7$–$C_{11}$ arylalkyl, for example benzyl. Alternatively, a solubilising group $P(O)(OH)_2$ may be introduced to a free hydroxy group by reaction with phosphorous acid and mercuric salts in the presence of a tertiary amine, as described by Obata and Mukaiyama in *J. Org. Chem.*, 32, 1063 (1967). As a further alternative, an amino, hydroxyl or mercapto group may be reacted with phosphorous acid preferably in the presence of a coupling agent such as dicyclohexylcarbodiimide and pyridine to yield a molecule possessing the solubilising group —OP(O)(OH)H. Optionally, this group may be oxidised to the corresponding phosphate derivative, for example using bis(trimethylsilyl) peroxide (see Scheme 14 below for an illustration of this method). A further process for the introduction of a 1 group —P(O)(OH)$_2$ is described in Australian patent application no. 54311/86, and involves the reaction of an amino, hydroxy or mercapto group with certain diesters of amides of phosphorus acid, followed by oxidation and hydrolysis of the resulting intermediate compounds.

Suitable reagents for the introduction of a solubilising group —NO$_2$ are lower alkyl nitrates such as methyl nitrate or ethyl nitrate, and acyl nitrates such as acetyl nitrate or benzoyl nitrate.

Other methods for the preparation of compounds of formulae (I) to (IAW) referred to herein are disclosed in U.S. Pat. Nos. 5,116,835, 5,126,326; 5,132,400; 5,145,957; 5,198,426; 5,212,157; 5,215,968; 5,212,667; 5,294,720; and 5,296,604; International Patent Application Nos. 91/08221; 91/10442; 92/151319 and 92/21696; European Patent Application Nos. 0528242; 0519433 and 0432595 and Australian Patent Application Nos. 35700/89; 53716/90; 63221/90; 71319/91; 71320/91; 71323/91; 82313/91; 83206/91; 87594/91; 90531/91; 90851/94; 90925/91; 91251/91; 91332/91; 18355/92; 26424/92; 37160/93; 38808/93 and 44930/93, the disclosures of each of which are incorporated herein by reference.

A third embodiment of the invention is directed to pharmaceutical compositions comprising a compound of formula (I) together with one or more pharmaceutically acceptable carriers, diluents, adjuvants and/or excipients.

In a fourth embodiment of the invention there is provided a method for inhibiting retroviral proteases in a mammal in need of such inhibition, comprising administering to the mammal an effective amount of a compound of the first embodiment or of a composition of the second embodiment. In one form of the third embodiment, there is provided a method for the treatment or prophylaxis of HIV viral infections such as AIDS.

For inhibiting retroviral proteases or the treatment of HIV viral infections, a composition of the second embodiment may be administered orally, topically, parenterally, e.g. by injection and by intra-arterial infusion, rectally or by inhalation spray.

For oral administration, the pharmaceutical composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as gum acacia or gum tragacanth.

For topical administration, the pharmaceutical composition may be in the form of a cream, ointment, gel, jelly, tincture, suspension or emulsion. The pharmaceutical composition may contain pharmaceutically acceptable binders, diluents, disintegrating agents, preservatives, lubricants, dispersing agents, suspending agents and/or emulsifying agents as exemplified above.

For parenteral administration, the compound of formula I or its salt may be prepared in sterile aqueous or oleaginous solution or suspension. Suitable non-toxic parenterally acceptable diluents or solvents include water, Ringer's solution, isotonic salt solution, 5% dextrose in water, buffered sodium or ammonium acetate solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example. Aqueous solutions for parenteral administration are also suitable for administration orally or by inhalation.

For rectal administration, the compound of formula I is suitably administered in the form of an enema or suppository. A suitable suppository may be prepared by mixing the active substance with a non-irritating excipient which is solid at ordinary temperatures but which will melt in the rectum. Suitable such materials are cocoa butter, waxes, fats, glycerol, gelatin and polyethylene glycols. Suitable enemas may comprise agents as exemplified above with reference to forms for topical administration.

Suitably, an inhalation spray comprising a compound of formula I will be in the form of a solution, suspension or emulsion as exemplified above. The inhalation spray composition may further comprise an inhalable propellant of low toxicity. Suitable propellants include carbon dioxide or nitrous oxide.

The dosage form of the compound of formula I will comprise from 0.01% to 99% by weight of the active substance. Usually, dosage forms according to the invention will comprise from 0.1% to about 10% by weight of the active substance.

The compound of formula I may be administered together or sequentially with one or more other active substances known or believed to have anti-viral activity. Examples of such other active substances include AZT, acyclovir, ddC, ddA, trisodium phosphonoformate, castanospermine, rifabutin, ribaviran, bropirimine, phosphonothioate oligodeoxynucleotides, dextran sulfate, α-interferon and ampligen.

BEST MODE OF CARRYING OUT THE INVENTION

Figure 1:
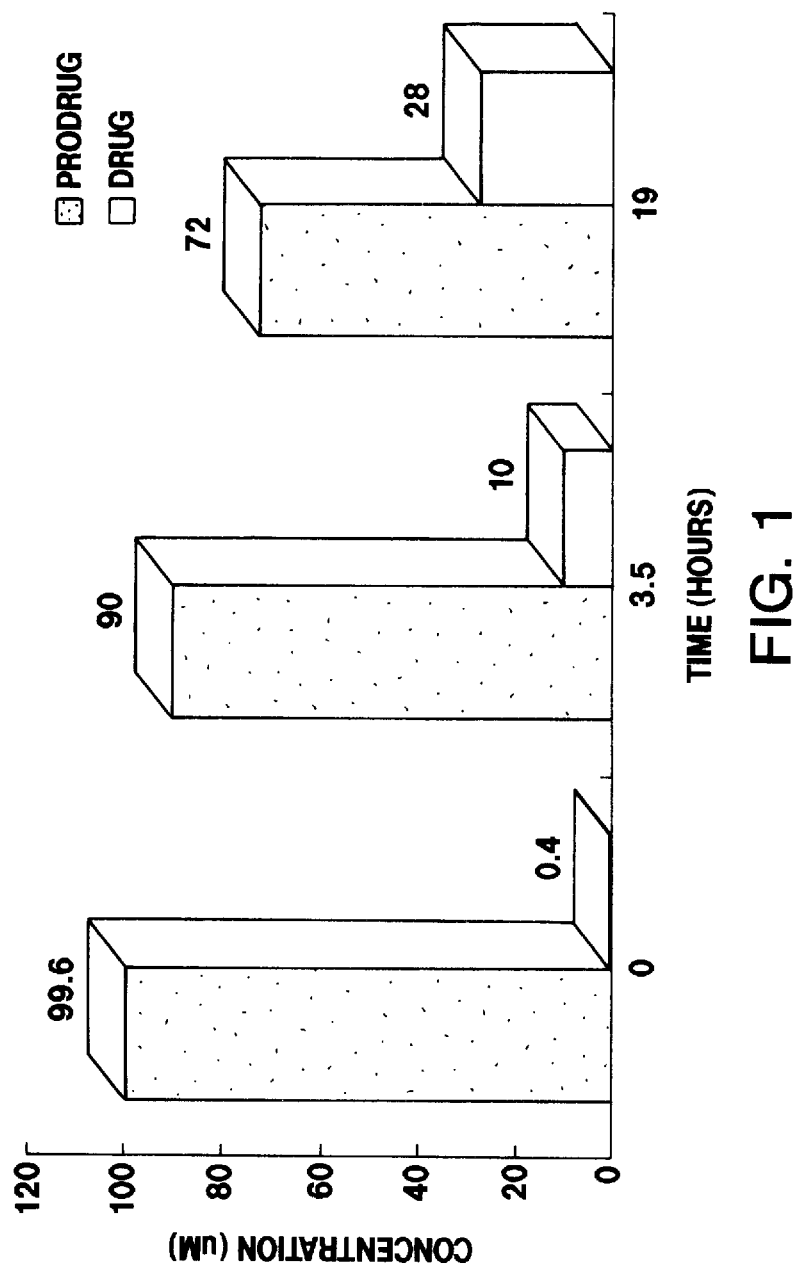
FIG. 1 is a graph showing the transformation of the compound of Example 5 ("Prodrug") into the compound of Example 20 of International Patent Application No. PCT/AU93/00103 ("Drug") in rabbit's blood in vitro.

Methods for the preparation of compounds of formula (IB) wherein x and y are both 0, B is —CH(OH)— and $R_{506}$, $R_{513}$, $R_{542}$ and $R_{543}$ are hydrogen are described in the following Schemes 11 and 12:

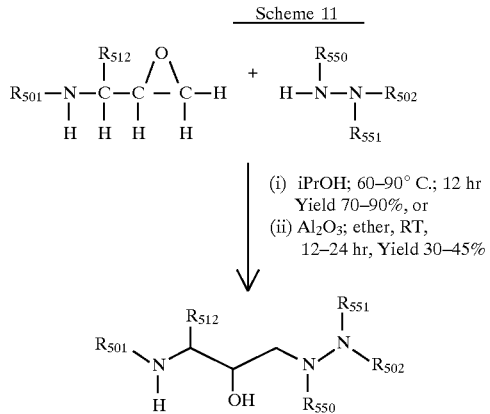

Scheme 13 presents an example of a method of preparation of Examples 11 and 12, commencing with the product of Scheme 12 in which $R_{501}$ is benzyloxycarbonyl, $R_{512}$ is methoxycarbonyl, $R_{550}$ and $R_{551}$ together form a 3,4-diazabicyclo[4.4.0]decane system and $R_{502}$ is tert-butoxycarbonyl:

-continued
Scheme 13

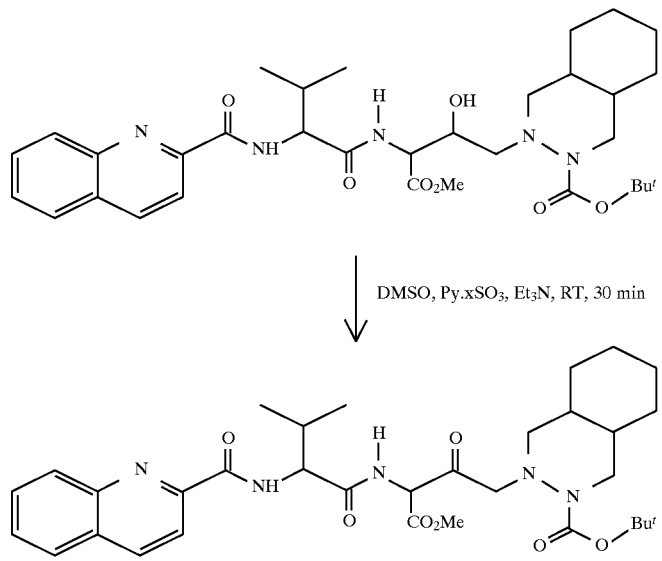

Scheme 14 presents an example of a method of preparation of compounds of formula shown in Table 4 below, in which the solubilising group Px is P(O)(OH)H or P(O)(OH)$_2$:

Scheme 14

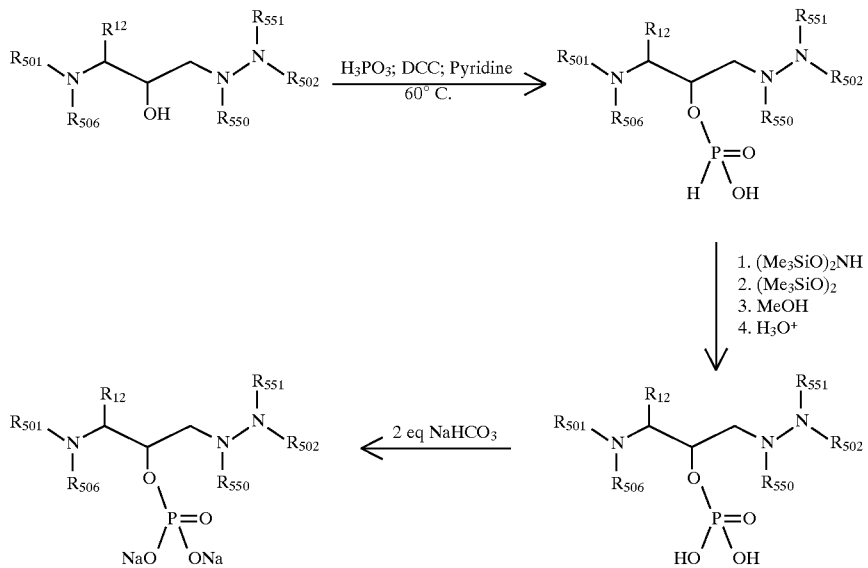

Compositions of the third embodiment may be prepared by means known in the art for the preparation of pharmaceutical compositions including blending, grinding, homogenising, suspending, dissolving, emulsifying, dispersing and mixing of the compound of formula (1) together with the selected excipient(s), carrier(s), adjuvant(s) and/or diluent(s).

In the method for the treatment of HIV viral infections in accordance with the fourth embodiment of the invention, a compound of the first embodiment will usually be administered orally or by injection. A suitable treatment may consist of the administration of a single dose or multiple doses of the compound of formula (1) or of a composition of the third embodiment. Usually, the treatment will consist of administering from one to five doses daily of the compound of formula (I) for a period of from one day to several years, up to the lifetime of the patient. Most usually, the treatment will consist of the administration of the compound of formula (I) for a period of from one day to one year.

The administered dosage of the compound of formula I can vary and depends on several factors, such as the condition of the patient. Dosages will range from 0.01 mg to 200 mg per kg. Usually, the dose of the active substance will be from 0.01 mg to 25 mg per kg of body weight.

Examples of dosage forms in accordance with the invention are as follows:

1. Tablet

Compound of formula I 0.01 to 20 mg, generally 0.1 to 10 mg

Starch 10 to 20 mg

Lactose 100 to 250 mg

Gelatin 0 to 5 mg

Magnesium stearate 0 to 5 mg

2. Capsule

Compound of formula I 0.01 to 20 mg, generally 0.1 to 10 mg

Glycerol 100 to 200 mg

Distilled water 100 to 200 mg

Saccharin 0 to 2 mg

Methyl Paraben 1 to 2 mg

Polyvinylpyrrolidone 0 to 2 mg

3. Injectable solution

Compound of formula I 0.01 to 20 mg, generally 0.1 to 10 mg

Sodium chloride 8.5 mg

Potassium chloride 3 mg

Calcium chloride 4.8 mg

Water for injection, q.s. to 10 ml

4. Elixir

Compound of formula I 0.01 to 1 to 20 mg, generally 0.1 to 10 mg

Sucrose 100 mg

Glycerol 2ml

Carboxymethylcellulose 20mg

Cherry flavour 2 mg

Water q.s. to 10 ml

EXAMPLES

The following Examples describe the preparation of compounds according to the invention and are intended to illustrate the invention. The Examples are not be construed as limiting in any way the scope of the present invention. Starting materials for the syntheses described in the following Examples are described in International Patent Application No. PCT/AU93/00103. In these Examples, melting points were taken on a hot stage apparatus and are uncorrected. Proton and phosphorus NMR spectra were recorded at 100 MHz or 300 MHz on Perkin Elmer R32 or Bruker EM 300 spectrometers, respectively, in $CDCl_3$ unless otherwise stated. Chemical shifts for proton NMR are ppm downfield from tetramethylsilane; chemical shifts for $P^{31}$ NMR are ppm downfield from 1,2-bis(diphenylphosphino)ethane external standard. Thin layer chromotography (TLC) was performed on silica gel 60-F254 plates (Merck). Compounds were visualized by ultraviolet light and/or 2% aqueous potassium permanganate solution. The composition (by volume) of the TLC solvent systems were (A) hexane/ethyl acetate 3:2, and (B) concentrated $NH_4OH$/isopropanol 1:3.

Example 1

4S,5S-5,6-Dibenzyl-1,2-(cis-1,2-cyclohexane) dimethyl-4-hydroxy-7-oxo-perhydro-1,2,6triazepine

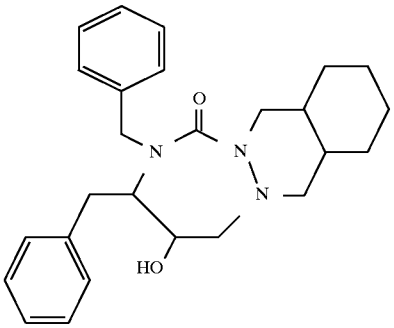

Step A: 4S,5S-5-benzyl-1,2-(cis-1,2-cyclohexane)dimethyl-4-t-butyldimethylsilyloxy-7-oxo-perhydro-1,2,6-triazepine: Hydrogen chloride gas was bubbled through the solution of 0.51 g (1.26 mmol) of cis-1,6-3-t-butoxycarbonyl4-[(2S,3S)-2-hydroxy-3-amino4-phenylbutyl]-3,4-diazabicyclo[4.4.0] decane (isomer having $R_f$ (A)=0.16 when eluted with 8% methanol in dichloromethane) in 10 ml of 1% solution of methanol in methylene chloride for 30 min at room temperature. After purging the excess of hydrogen chloride with nitrogen gas the solvent was removed under reduced pressure to give 0.42 g (100% yield) of the hydrochloride salt of cis-1,6-4-[(2S,3S)-3-amino-2-hydroxy-4-phenylbutyl]-3,4-diaza-bicyclo[4.4.0]decane as a hygroscopic, white solid. This was dissolved in 1 ml of dry DMF and 0.114 g (1.68 mmol) of imidazole and 0.21 g (1.38 mmol) of t-butyldimethylsilyl chloride were added under nitrogen. The resulting mixture was stirred overnight at room temperature and evaporated to dryness in vacuo. The residue was diluted to 20 ml with ethyl acetate, washed with saturated sodium bicarbonate and dried over anhydrous potassium carbonate and filtered off. The filtrate was evaporated to dryness under reduced pressure and the residue was dissolved in 20 ml of dry dioxane. To this, 0.204 g (1.26 mmol) of 1,1'-carbonyldiimidazole was added and the resulting mixture was stirred for 24 hrs at room temperature. After evaporation of the solvent under reduced pressure the residue was diluted to 15 ml with ethyl acetate and washed with water (3×) and saturated aqueous sodium chloride solution, and then dried over anhydrous magnesium sulfate. Evaporation of the solvent under reduced pressure and purification of the residue by column chromatography (silica gel; hexane/ethyl acetate 3:2) gave 0.095 g (17% yield) of the title compound, melting at 145°–146° C.; $R_f$(A)=0.43; NMR 0.07, 0.09 (s,s 6H, $CH_3$); 0.94 (s, 9H, t-butyl $CH_3$); 1.2–2.0 (m, 10H, cyclohexane $CH_2$, CH); 2.5–2.8 (m, 4H, $CH_2$-3, benzyl $CH_2$); 3.2–3.7 (m, 4H, dimethyl $CH_2$); 3.9–4.0 (m, 3H, CH4,5, NH); 7.1–7.32 (m, 5H, aromatic).

Step B: 4S, 5S-5,6-dibenzyl-1,2-(cis-1,2-cyclohexane) dimethyl-4-t-butyldimethylsilyloxy-7-oxo-perhydro-1,2,6-triazepine:

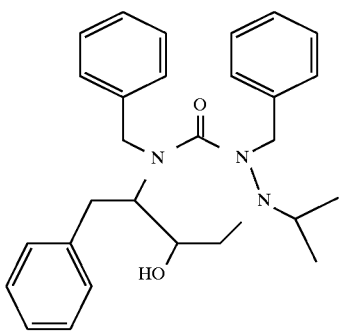

4.5 mg (0.15 mmol) of 80% dispersion of sodium hydride in mineral oil was added to a solution of 0.0665 g (0.15 mmol) of the product of Step A in 0.2 ml of dry DMF at room temperature. After stirring for 30 min at room temperature, 0.0179 ml (0.15 mmol) of benzyl bromide was then added. The resulting mixture was stirred overnight, then diluted to 15 ml with ethyl acetate and washed with water, saturated aqueous sodium chloride solution and dried over anhydrous magnesium sulfate. Evaporation of the solvent under reduced pressure and purification of the residue by column chromatography gave 0.029 g (36% yield) of the title compound as a heavy syrup; $R_f$ (A)=0.77; NMR −0.35, −0.18 (s, s, $CH_3$); 0.8 (s, 9H, t-butyl $CH_3$); 1.2–2.2 (m, 1OH, cyclohexane $CH_2$, CH); 2.56–4.18 (m, 12H, benzyl $CH_2$, dimethyl $CH_2$, $CH_2$-3, CH-4,5); 6.8–7.4 (m, 10H, aromatic).

Step C. 4S,5S-5,6-Dibenzyl-1,2-(cis-1,2-cyclohexane)dimethyl-4-hydroxy-7-oxo-perhydro-1,2,-triazepine:

A mixture of 29 mg (0.0543 mmol) of the product of Step B and 0.0426 g (0.163 mmol) of tetrabutylammonium fluoride hydrate in 1 ml of anhydrous acetonitrile was stirred at 45°±5° C. for 3 hrs and evaporated to dryness. The residue was purified by column chromatography (silica gel, hexane/ethyl acetate 3:2) to give 0.019 g (86% yield) of the title compound as a colourless foam; $R_f$ (A)=0.26; NMR 1.2–2.1 (m, 18H, cyclohexane $CH_2$, CH, OH, 3.5×$H_2O$); 2.6–4.0 (m, 1 1H, benzyl $CH_2$, dimethyl $CH_2$, $CH_2$-3, CH-5); 4.83 (m, 1H, CH4); 7.0–7.4 (m, 10H, aromatic).

Example 2

4S,5S-1,5,6,Tribenzyl-2-isopropyl4-hydroxy-7-oxo-perhydro-1,2,6-triazepine

Step A: 4S,5S-5-enzyl-2-isopropyl-4t-butyldimethylsilyloxy-7-oxo-perhydro-1,2,6-triazepine:

When t butyl 3-isopropyl-3-[(2S,3S)-3-amino-2-hydroxy4-phenylbutyl]-carbazate was substituted for cis-1, 6-3-t-butoxycarbonyl4-[(2S,3S)-2-hydroxy-3-aminophenylbutyl]-3,4-diazabicyclo[4.4.0]decane in Step A of Example 1 the identical process afforded the title compound in 20% overall yield; melting point =131°–132° C. (hexane); $R_f$ (A)=0.8; NMR 0.10, 0.11 (s, s, 6H, silyl $CH_3$); 0.95 (s, 9H, t-butyl $CH_3$); 1.1–1.35 (m, 6H isopropyl $CH_3$); 2.8–3.2 (m, SH, $CH_2$-3, CH-5, benzyl $CH_2$); 3.45 (m, 1H, isopropyl H); 4.18 (m, 1H, CH-4); 4.41 (m, 1H NH-6); 5.63 (s, 1H, NH-1); 7.1–7.4 (m, SH, aromatic).

Step B: 4S,5S-1,5,6tribenzyl-²-isopropyl-4-t-butyldimethylsilyloxy-7-oxo-perhydro-1,2,triazepine:

A mixture of 0.07 g (0.185 mmol) of the product of Step A and 0.012 g (0.371 mmol) of sodium hydride in 0.2 ml of dry DMF was stirred for 30 min at room temperature, then 0.044 ml (0.371 mmol) of benzyl bromide was added. The resulting mixture was stirred overnight and worked up as described in Step B of Example 1. The purification of the crude product by column chromatography (silica gel, hexane/ethyl acetate 3:2) gave 0.031 g (30% yield) of the title compound as a colourless syrup; Rf (A) =0.74, NMR −0.28, −0.22 (s,s, 6H, silyl $CH_3$); 0.8 (s, 9H, t-butyl $CH_3$); 1.0–1.35 (m, 6H, isopropyl $CH_3$); 2.5–3.3 (m, 5H, $CH_{2-3}$, CH-5,5-benzyl $CH_2$); 3.45–3.82 (m, 2H, isopropyl CH, CH-4); 4.0–5.38 (m, 4H, 1,6-benzyl $CH_2$); 6.6–7.8 (m, 15H, aromatic).

Also, the fractions with Rf (A)=0.63 were combined and evaporated to dryness under reduced pressure to give 0.061 g (70% yield) of 4S,5S-5,6-dibenzyl-2-isopropyl4-t-butyl-dimethylsilyloxy-7-oxo-perhydro-1,2,6-triazepine as a colourless solid; NMR 0.11 (d, 6H, silyl $CH_3$); 0.93 (s 9H, t-butyl $CH_3$); 1.24 (m, 6H, isopropyl $CH_3$); 2.4–3.4 (m, 5H, $CH_2$-3, CH-5,5-benzyl $CH_2$); 3.75 (m, 1H, isopropyl CH); 4.0–4.7 (m, 3H, CH4, 6-benzyl $CH_2$); 5.05 (m 1H, NH); 7.0–7.7 (m, 15H, aromatic).

Step C: 4S,5S-1,5,6 Tribenzyl-2-isopropyl-4-hydroxy-7-oxo-perhydro-1,2,6 triazepine:

When the title compound of Step B was substituted for 4S,5S-5,6-dibenzyl-1,2-(cis-1,2-cyclohexane)-dimethyl-4-t-butyldimethylsilyloxy-7-oxo-perhydro-1,2,6-triazepine in Step C of Example 1, the identical process afforded the title compound with 98% yield as a foam; Rf (A)=0.68; NMR ($CDCl_3$) 1.07–1.19 (d, d, 6H, isopropyl $CH_3$); 1.58 (s, 1H, OH); 2.6–3.15 (m, 5H, $CH_2$-3, CH-5,5-benzyl $CH_2$); 3.2–5.3 (m, 6H, isopropyl CH, CH4,1,6-benzyl $CH_2$); 6.8–7.6 (m, 15H, aromatic).

Example 3

4S,5S-5,6-dibenzyl-2-isopropyl4-hydroxy-7-oxo-perhydro-1,2,6-triazepine

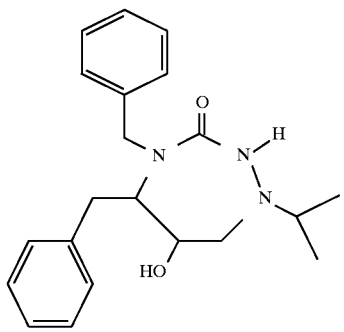

When 4S,5S-5,6-2-isopropyl4-t-butyldimethylsilyloxy-7-oxo-perhydro-1,2,6-triazepine was substituted for 4S,5S-1, 5,6-tribenzyl-2-isopropyl-4-t-butyldimethylsilyloxy-7-oxo-perhydro-1,2,6-triazepine in Step C of Example 2 the identical process afforded the title compound in 88% yield; melting point=191°–193° C.; Rf (A)=0.17; NMR (DMSO-$d_6$, 80° C.) 2.5–3.0 (m, 4H, $CH_2$-3,5-benzyl $CH_2$); 3.28 (m, 1H, CH-5); 3.6 (m, 1H, CH-4); 3.8 (m, 1H, isopropyl CH); 4.2–4.7 (m, 3H, 6-benzyl $CH_2$; OH); 5.41 (m, 1H, NH); 7.0–7.4 (m, 10H, aromatic).

Example 4 t-Butyl 3-isopropyl-3-[(2S, 3S)-2-phosphitooxy-3-(N-quinaldoyl-L-paraginyl)amino-4-phenylbutyl carbazate

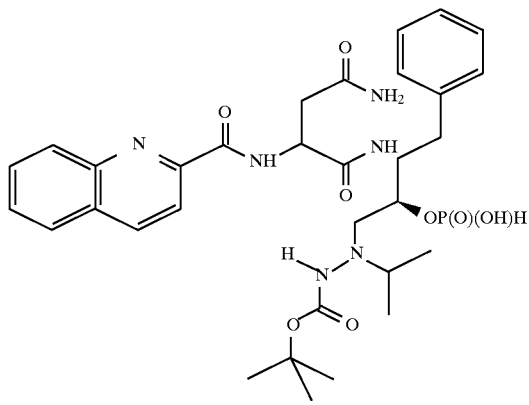

To a mixture of 0.4 g (0.67 mmol) of t-butyl 3-isopropyl-3-[(2S, 3S)-2-hydroxy-3-(N-quinaldoyl-L-asparaginyl) amino4-phenylbutyl carbazate and 0.12 g (1.47 mmol) of anhydrous phosphorous acid in 1.5 ml of anhydrous pyridine was added 0.28 g (1.4 mmol) of dicyclohexylcarbodiimide at room temperature under nitrogen, with stirring. After stirring for 2 hours at 60° C., the solvent was evaporated under reduced pressure and the residue was treated with 28 ml of 0.1 ml aqueous sodium bicarbonate and vigorously stirred for 1 hour at room temperature. The precipitate was filtered off and washed with water and the filtrate was acidified to pH~1.5 with concentrated hydrochloric acid. The product was taken up b extraction with ethyl acetate (3×50 ml), and the organic phase was dried over anhydrous magnesium sulfate. Evaporation of the solvent gave 0.42 g (95% yield) of the title product as a colourless solid; Rf (B)=0.62; $H^1$NMR (CDCl$_3$): 1.08 (m, 6H, isopropyl CH$_3$); 1.41 (s, 9H, t-butyl CH$_3$); 2.7–4.8 (m, 14H, asn CH$_2$, butyl CH$_2$-1,4; CH-2,3; isopropyl CH; P—OH×2H$_2$O); 5.12 (m, 1H, asn CH); 5.89 (s, 0.5 H, PH); 6.2–8.5 (m, 15.5H, aromatic, amide NH, 0.5 PH); 9.02 m, 1H, asn NH); $P^{31}$NMR (CDCl$_3$) 14.99 ($J_{P-H}$=636 Hz).

Example 5 t-Butyl 3-isopropyl-3-[(2S, 3S)-2-phosphonooxy-3-(N-quinaldoyl-L-asparaginyl)amino-4-phenylbutyl carbazate

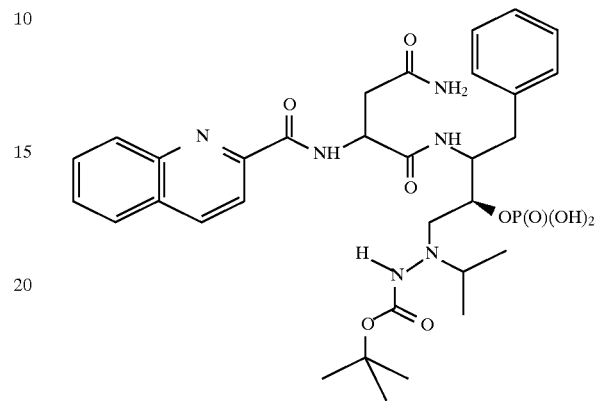

A suspension of 0.4 g (0.6 mmol) of the product of Example 4 in 2 ml of hexamethyldisilazane was stirred for 45 min at 120°±5° C. At this point the reaction mixture became homogeneous. To this 0.3 ml of bis(trimethylsilyl) peroxide (Cookson, P.G et al., *J. Organomental. Chem.*, 1975, 92, C31) was added and stirring was continued for 1 hour at the above temperature. The reaction mixture was cooled to room temperature, then evaporated to dryness in vacuo. The residue was dissolved in 20 ml of methanol, evaporated to dryness under reduced pressure and redissolved in 12 ml of 0.1 ml aqueous sodium bicarbonate. The resulting mixture was acidified to pH~1.5 with concentrated hydrochloric acid, saturated with sodium chloride and extracted with ethyl acetate (3×50 ml). The combined organic phase was dried over anhydrous magnesium sulfate and evaporated to dryness to give 0.39 g (96% yield) of the title compound as a colourless solid; R$_f$(B)=0.07; $H^1$NMR (CDCl$_3$): 1.2 (m, 6H, isopropyl CH$_3$); 1.4 (s, 9H, t-butyl CH$_3$); 2.8–4.2 (m, 8H, asn CH$_2$ butyl CH$_2$-1,4, CH-3, isopropyl CH); 4.2–6.4 (m, 5H, asn CH, butyl CH-2, NH, POH); 6.5–8.4 (m, 14H, aromatic, NH); 8.78 (m, 2H, NH); $P^{31}$NMR (CDCl$_3$) 9.6 (s).

Example 6 cis-1,6-3-t-Butoxcarbonyl4[(2S, 3S)-2-phosphitooxy-3-(N-quinaldoyl-L-asparaginyl)amino-4-phenylbutyl]-3,4-diaza-bicyclo[4.4.0]decane

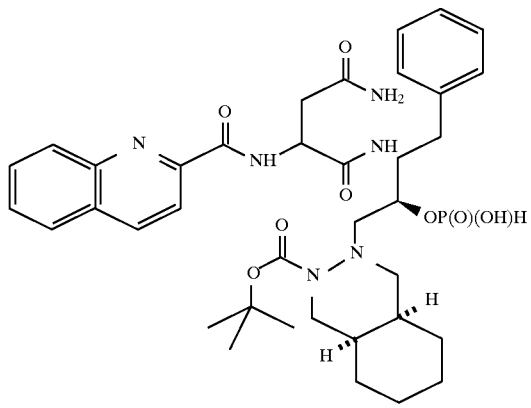

When cis-1,6-3-t-butoxycarbonyl-4-[(2S, 3S)-2-hydroxy-3-(N-quinaldoyl-L-asparaginyl)amino4-phenylbutyl]-3,4-diaza-bicyclo[4.4.0]decane is substituted for t-butyl 3-isopropyl-3-[(2S, 3 )-2-hydroxy-3-(N-quinaldoyl-L-asparaginyl)amino4-phenylbutyl-carbazate in Example 4, the identical process affords the title compound in 89% yield, as a colourless solid; $R_f(B)=0.64$; $H^1$NMR (CDCl$_3$): 1.1–1.8 (m, 19H, t-butyl CH$_3$, decane CH$_2$-7,8,9,10, CH-1, 6); 2.12 (m, 1H, butyl CH-3); 2.6–5.1 (m, 19H, asn CH$_2$, CH, butyl CH$_2$-1,4, CH-2, decane CH$_2$-2,5, POH×2.5 H$_2$O); 6.1–8.4 (m, 15H, amide NH, PH, aromatic); 9.08 (m, 1H, asn NH); P$^{31}$NMR (CDCl$_3$) 16.43 ($J_{PH}$=700 Hz).

Example 7 cis-1,6-3-t-Butoxycarbonyl-4-[(2S, 3S)-2-phosphonooxy-3-N-quinaldoyl-L-asparaginyl)amino-4phenylbutyl]-3,4-diaza-bicyclo[4.4.0]decane

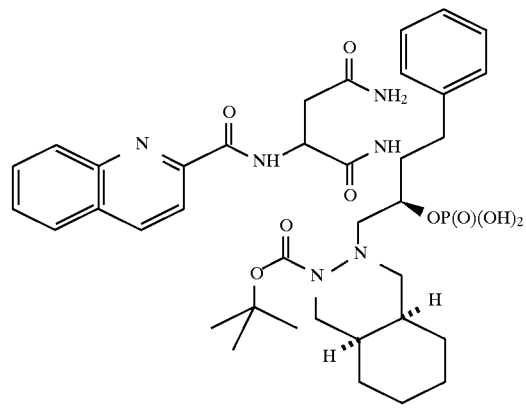

When the product of Example 6 is substituted for t-butyl 3-isopropyl-3-[(2S, 3S)-2-phosphitooxy-3-(N-quinaldoyl-L-asparaginyl)amino4-phenylbutyl carbazate in Example 5, the identical process affords the title compound in 83% yield, as a colourless solid; $R_f(B)=0.12$; $H^1$NMR (CDCl$_3$): 1.1–2.4 (m, 20H, t-butyl CH$_3$, decane CH$_2$-7,8,9,10, CH-1, 6, butyl CH-3); 2.7–3.9 (m, 9H, asn CH$_2$, butyl CH$_2$-1,4, CH-2, decane CH$_2$-5); 5.1 (m, 1H, asn CH); 6.1–8.3 (m, 21H, amide NH, aromatic, POH×2.5 H$_2$O); 9.05. (m, 1H, asn NH); P$^{31}$NMR (CDCl$_3$) 10.5 (s).

Other representative compounds in accordance with the invention are described in Tables 1 to 5. Other compounds in accordance with the invention are substances in which a hydroxyl, amino or mercapto group is any of the compounds described in the Examples and disclosures of the following, has been derivatised with a solubilising group Px as defined herein:

U.S. Pat. Nos. 5,116,835, 5,126,326; 5,132,400; 5,145,951; 5,198,426; 5,212,157; 5,215,968; 5,221,667; 5,250563; 5,268,361; 5,294,720; and 5,296,604; International Patent Application Nos. 90/09191; 91/08221; 91/10442; 92/15319 and 92/21696; European Patent Application Nos. 0574135; 0528242; 0519433 and 0432595 and Australian Patent Application Nos. 35700/89; 42308/89; 45665/89; 46115/89; 53716/90; 63221/90; 66334/90; 71319/91; 71320/91; 71323/91; 77326/91; 81910/91; 82054/91; 88900/91; 82313/91; 83234/91; 83206/91; 85877/91; 87309/91; 87409/91; 87594/91; 15 88900/91; 89941/91; 90531/91; 90851/91; 90925/91; 91223/91; 91251/91; 91332/91; 91790/92; 10812/92; 18355/92; 19373/92; 21944/92; 22889/92; 24129/92; 24690/92; 26424/92; 31628/93; 35165/93; 35621/93; 37160/93; 38808/93; 41230/93; 41659/93; 44930/93 and 49072/93, the disclosures of each of which are incorporated herein by reference.

Example 8

In Vivo Removal of Phosphono Group

Solutions:

The product of Example 5 was converted quantitatively into the corresponding disodium salt by treatment of the free acid with 2 equiv. of 0.2M sodium bicarbonate and lyophilization of the resulting solution. The stock solutions of the disodium salt of the product of Example 5, for blood and animal experiments, were prepared in sterile water.

Analyses:

Reverse phase analyses (HPLC) were performed on Waters ternary gradient liquid chromatograph equipped with 996 diode array detector set at 238 nm. Separations were achieved on Alltima RP-18 (250×4.6 mm, i.d., 5µ particles), with the flow rate of 1 ml/min. The isocratic mobile phase composition used for analyses consisted of 40% of 0.1% aqueous trifluoroacetic acid (TFA) and 60% of acetonitrile containing 0.1% TFA and 10% water. The retention time of the product of Example 5 (referred to below as "Prodrug") was in the range of 3.6–3.9 minutes and the retention time of t-butyl 3-isopropyl-3-[(2S, 3S)-2-hydroxy-3-(N-quinaldoyl-L-asparaginyl)amino4-phenylbutyl -carbazate (referred to below as "Drug) was about 6.2 minutes. Detector response was linear from 0.5 to 120 µM for Prodrug and 0.05 to 50 µM for Drug.

Standards and Sample Processing: The standards were prepared by serial dilution of Prodrug or Drug in rabbit blood collected into heparinised tubes. Blood samples were transferred into vials containing 150 units of heparin and stored on ice until processed. The blood samples were then separated by centrifuging at 6000 rpm for 10 min. The plasma samples were frozen and stored at −20° C. until they were analysed.

Plasma preparation for HPLC analysis: An equal volume (100 µL) of thawed plasma and acetonitrile was stirred with a vortex mixer and allowed to stand at room temperature for 5 minutes, then centrifuged at 14000 rpm for 10 minutes. Samples of the supernatant (50 µL) were injected into the chromatograph.

Transformation of Prodrug into Drug by Blood was established by measurement of prodrug and drug concentrations in plasma following the prodrug incubation in whole rabbit's blood (100 μM) at 36° C. for 19 hours. FIG. 1 shows the concentrations of prodrug and drug under these conditions over 19 hours.

Figure 2:
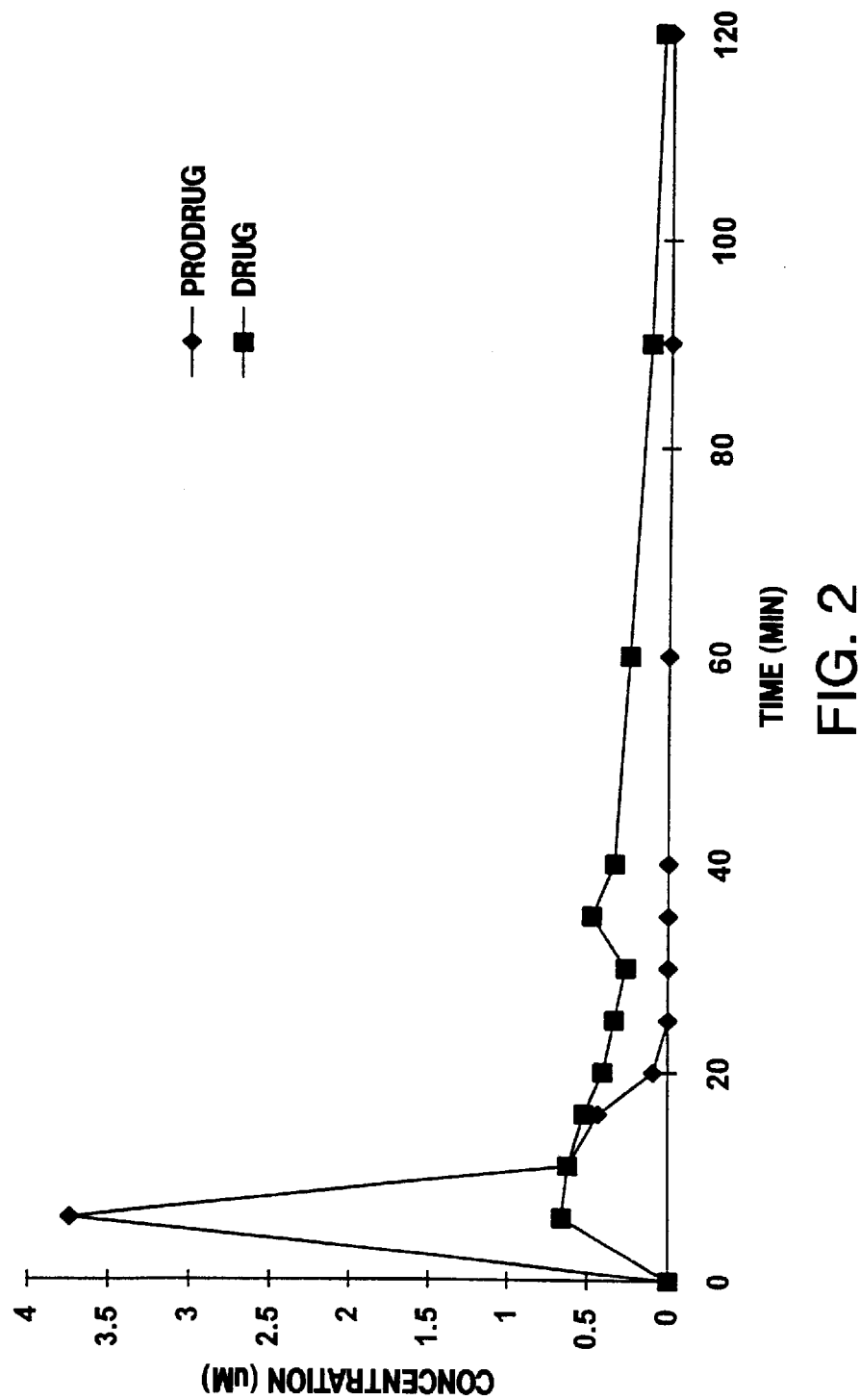
FIGS. 2 and 3 are graphs showing the transformation of Prodrug into Drug in vivo following intravenous and intramuscular (respectively) administration to a rabbit.

Transformation of Prodrug into Drug after intravenous (IV) administration of prodrug (9.2 mg/kg) to rabbit was established by measurement of prodrug/drug concentrations in plasma over 120 min. The formulated product, containing 30 mg/ml of prodrug, was well tolerated by the rabbit. The plasma profiles of prodrug and drug disappearance are shown in FIG. 2.

Figure 3:
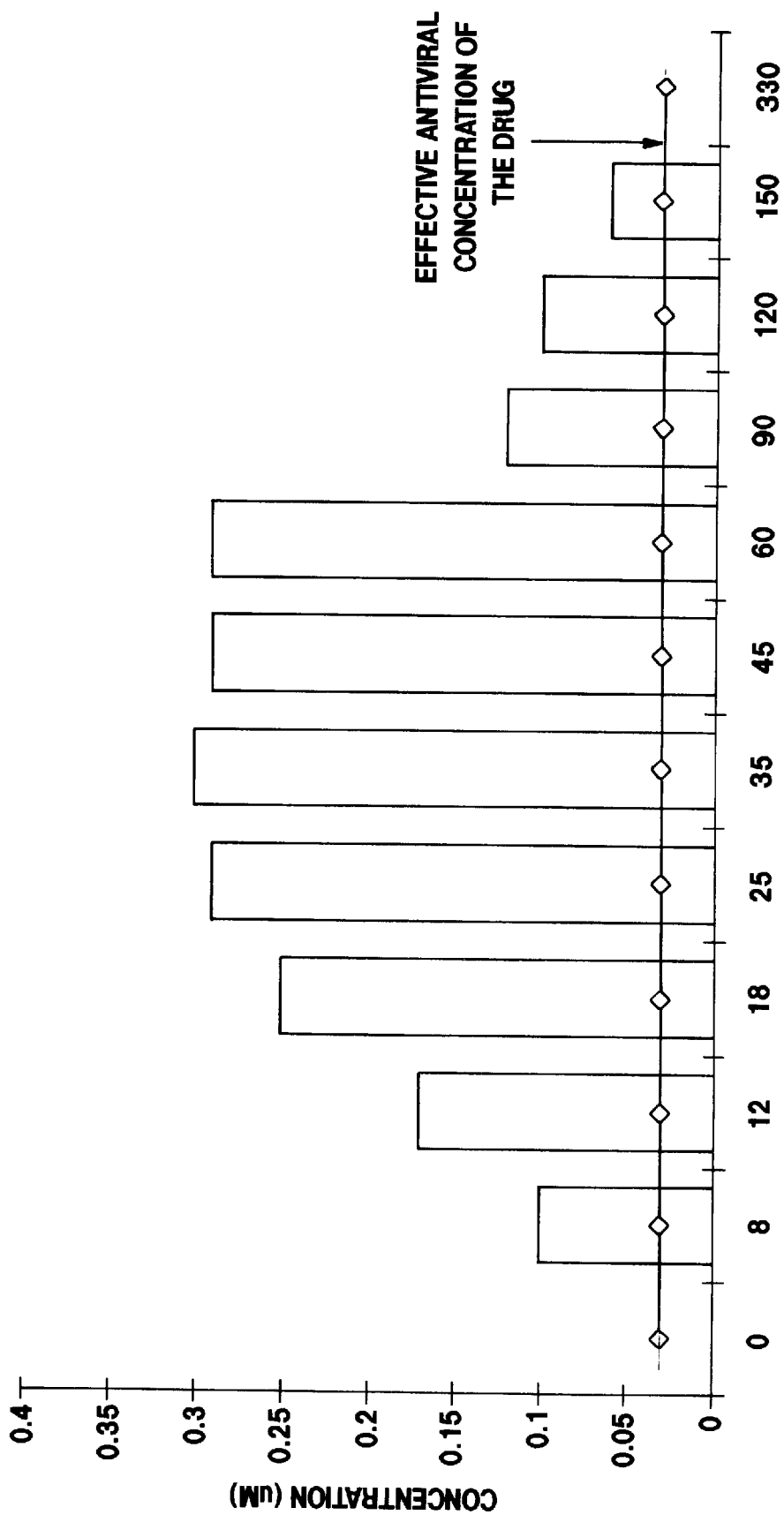

Transformation of Prodrug into Drug after Intramuscular (IM) administration of prodrug (7.9 mg/kg) to rabbit was established by measurement of drug concentrations in plasma over 330 min. The formulated product, containing 30 mg/ml of prodrug was well tolerated by the rabbit. The time dependence of the plasma concentration of the drug are shown in FIG. 3.

When prodrug was administered to a dog orally at a dose of 20mg/kg, the blood plasma concentration of drug was found to be 0.044, 0.141, 0.189, 0.172, 0.164, 0.132, 0.089 and 0.060 μM, respectively, after 5, 15, 30, 47, 63, 93, 124 and 155 minutes. When prodrug was administered to a second dog orally at a dose of 10 mg/kg, the blood plasma concentration of drug was found to be 0.137, 0.371, 0.297, 0.242, 0.176, 0.11, 0.071, and 0.050 μM, respectively, after 5, 15, 30, 45, 60, 94, 123 and 154 minutes.

TABLE 1

Compounds of formula $$R_{501}\text{-}N(R_{506})\text{-}A\text{-}B\text{-}A^*\text{-}N(R_{550})\text{-}N(R_{551})(R_{502})$$

| Compound No. | $R_{501}$ | $R_{506}$ | A | B |
|---|---|---|---|---|
| 9. | BzOC(O)— | Et | —CH$_2$— | —CH(CH$_2$OH)— |
| 10. | quinoline-2-C(O)NH-C(=CH-C(O)-Ph)-CH$_2$— | Me | —CH$_2$— | —CH(CH$_2$OH)— |
| 11. | quinoline-2-C(O)NH-CH(iPr)-C(O)— | H | —CH(COOMe)— | —CH(OH)— |
| 12. | quinoline-2-C(O)NH-CH(iPr)-C(O)— | H | —CH(COOMe)— | cyclopropyl-C(=O) |
| 13. | pyridine-2-C(O)NH-CH(Et)-C(O)— | EtO(CH$_2$)$_2$ | —CH$_2$CF$_2$— | —CH(OAc)— |
| 14. | Ac | Ph | —CH$_2$CH$_2$— | —C(OH)(CO$_2$Me)— |
| 15. | MeS(O) | iPr | —CH$_2$CHF— | epoxide (HC—CH with O bridge) |
| 16. | MeS(O)$_2$ | Pr | —CH(Me)— | —CH(OTHP)— |

TABLE 1-continued

Compounds of formula $$R_{501}\text{-}\underset{R_{506}}{N}\text{-}A\text{-}B\text{-}A^*\text{-}\underset{R_{550}}{N}\text{-}\underset{R_{502}}{N}\overset{R_{551}}{\underset{R_{502}}{}}$$

| # | $R_{501}, R_{506}$ | A | B, A* | $R_{550}, R_{551}, R_{502}$ |
|---|---|---|---|---|
| 17. | H | BzOC(O)— | —C(Me)₂— | —C(OH)(C(O)NMe₂)— |
| 18. | Et | Bz | —CH(OS(O)₂Me)— | —CH(OH)— |
| 19. | Et | Bz | —CH(OS(O)₂Me)— | —C(O)CH₃ (acetyl) |
| 20. | BzOC(O)NH-CH(Me)-C(O)— | 2-pyridyl-methyl | —CH(cyclohexyl)— | —C(OH)(CH₃)— |
| 21. | (CH₃)₂CHCH₂-CH(NHC(O)OBuᵗ)-CHO | Me | —CH₂CCl₂— | —CH(Ph)— |
| 22. | HOCH₂-CH(NH₂)-C(O)— | H₂NCH₂CH₂ | —CH₂CHCl— | —CH(OH)— |
| 23. | HOCH₂-CH(NH₂)-C(O)— | H₂NCH₂CH₂ | —CH₂CHCl— | —C(O)CH₃ |
| 24. | 2-pyridyl-CH₂-OC(O)NH-CH(tetrahydrofuran-3-yl)-C(O)— | Me₂N | —CH₂CF₂— | —CH(CH₂OAc)— |
| 25. | Ph | n-Bu | —CH₂—CH(N(Me)Ph)— | —C(OH)(CH₃)— |
| 26. | Me | 4-piperidyl | —C(O)CH₃ | epoxide (—CH-O-C(CH₃)—) |
| 27. | quinoline-2-C(O)NH-CH(C(O)NH₂)(C(O))— | cyclohexyl-CH₂— | —CH₂—C(CH₃)(OP(O)(OCH₃)₂)— | —CH(OCH₃)— |

TABLE 1-continued

Compounds of formula $$R_{501}(R_{506})N-A-B-A^*-N(R_{550})-N(R_{551})(R_{502})$$

| # | R501/R506 (N-substituent) | A | B | A* / substituent |
|---|---|---|---|---|
| 28. | pyrrolidin-2-yl-C(O)– (N–H) | 3-methylindol-1-yl (N–H) | –CH(Et)– | –C(OCH₃)₂– |
| 29. | cyclohexyl | BzC(O) | –CH(C(O)NH₂)– | –C(OH)(Ph)– |
| 30. | cyclohexyl-CH₂– | CH₂=CH–CHO (acrolein) | –CH(Ph)– | –C(OH)(CO₂Et)– |
| 31. | furan-2-yl-CH₂– | t-BuOC(O) | –CH(CH=CH₂)– | –C(CH₂OH)(CH₃)– |
| 32 | PhOC(O) | HOCH₂CH₂ | –C(CH₃)(CH.CF₂)– | –C(CH₂OH)(CH₂OH)– |
| 33. | pyridin-2-yl-CH₂–OC(O)CH₃ | NCCH₂CH₂ | –CH(CH₃)–CHF– | –C(CH₂OH)(CO₂Me)– |
| 34. | H₂NC(O) | HOC(O)CH₂ | –CH(naphth-1-yl-CH₂)– | –CH(OH)– |
| 35. | H₂NC(O) | HOC(O)CH₂ | –CH(naphth-1-yl-CH₂)– | –C(=O)CH₃ |
| 36. | MeOC(O) | MeOC(O)CH₂ | –CH(Bz)– | –CH(OH)– |
| 37. | MeOC(O) | MeOC(O)CH₂ | –CH(Bz)– | –C(=O)CH₃ |
| 38. | Me₂NS(O)₂ | Ph | –CH(pyridin-2-yl)– | –C(OH)(CO₂NMe₂)– |

5,888,992

TABLE 1-continued

Compounds of formula $$R_{501}\underset{R_{506}}{N}-A-B-A^*-\underset{R_{550}}{N}-\underset{R_{502}}{N}-R_{551}$$

| | | | | |
|---|---|---|---|---|
| 39. | Me₂NS(O) | OMe | —CH—<br>\|<br>(4-quinolinyl) | OH<br>\|<br>—C—<br>\|<br>C(S)CH₃ |
| 40. | 2-methylpyrazinyl | Ac | —CH—<br>\|<br>C(O)CH₃ | OH<br>\|<br>—C—<br>\|<br>C(O)SCH₃ |
| 41. | t-BuOC(O)— | H | Bz<br>\|<br>—CH— | OH<br>\|<br>—C—<br>\|<br>C(O)NH₂ |
| 42. | BzOC(O)NH—CH(iPr)—C(O)— | H | Bz<br>\|<br>—CH— | —CH(OH)— |
| 43. | 2-quinolinyl-C(O)NH—CH(CH₂C(O)CONH₂)—C(O)— | H | Bz<br>\|<br>—CH— | —CH(OH)— |
| 44. | 2-quinolinyl-C(O)NH—CH(CH₂C(O)CONH₂)—C(O)— | H | Bz<br>\|<br>—CH— | —CH(OH)— |
| 45. | 2-quinolinyl-C(O)NH—CH(CH₂C(O)CONH₂)—C(O)— | H | Bz<br>\|<br>—CH— | —CH(OH)— |
| 46. | 2-quinolinyl-C(O)NH—CH(CH₂C(O)CONH₂)—C(O)— | H | Bz<br>\|<br>—CH— | —CH(OH)— |
| 47. | 2-quinolinyl-C(O)NH—CH(CH₂C(O)CONH₂)—C(O)— | H | Bz<br>\|<br>—CH— | —CH(OH)— |
| 48. | 2-quinolinyl-C(O)NH—CH(CH₂C(O)CONH₂)—C(O)— | H | Bz<br>\|<br>—CH— | —CH(OH)— |
| 49. | BzOC(O)NH—CH(iPr)—C(O)— | H | Bz<br>\|<br>—CH— | C(O)iPr |

TABLE 1-continued

Compounds of formula $R_{501}R_{506}N-A-B-A^*-N(R_{550})-N(R_{551})R_{502}$

| # | $R_{501}$ ($R_{506}$=H) | A-B-A* | $R_{550}$ | $R_{551}R_{502}N$— / remainder |
|---|---|---|---|---|
| 50. | t-BuOC(O)NH—CH(i-Pr)—C(O)— | 2-pyridyl-CH₂— | —CH(Bz)— | —CH(OH)— |
| 51. | t-BuOC(O)— | H | —C(Bz)(CONH₂)— | —CH(OH)— |
| 52. | t-BuOC(O)— | H | —CH(Bz)— | —CH(OH)— |
| 53. | n-Pr | n-Pr | —CH(Bz)— | —CH(OH)— |
| 54. | thiomorpholine-N-C(O)—NH—CH(i-Pr)—C(O)— | H | —CH(4-MeC₆H₄-CH₂)— | —CH(OH)— |
| 55. | morpholine-N-C(O)—NH—CH(i-Pr)—C(O)— | H | —CH(4-MeC₆H₄-CH₂)— | —CH(OH)— |
| 56. | PhCH₂C(O)—NH—CH(i-Bu)—C(O)NH— | H | —CH(Bz)— | —CH(OH)— |
| 57. | (2-pyridyl)CH₂C(O)—NH—CH(i-Pr)—C(O)NH— | H | —CH(Bz)— | —CH(OH)— |
| 58. | t-BuOC(O)— | i-Bu | —CH(4-NH₂-C₆H₄-CH₂)— | —C(OH)—C(O)—N(piperidine) |
| 59. | | —C(O)—CH₂—C(O)— | —CH(cyclohexyl-CH₂)— | —C(OH)—C(S)NMe₂ |
| 60. | t-BuOC(O)— | H | —CH(Bz)— | —CH(OH)— |
| 61. | t-BuOC(O)— | H | —CH(Bz)— | —CH(OH)— |

TABLE 1-continued

Compounds of formula $$R_{501}\text{-}\underset{\underset{R_{506}}{|}}{N}\text{-}A\text{-}B\text{-}A^*\text{-}\underset{\underset{R_{550}}{|}}{N}\text{-}\underset{\underset{R_{502}}{|}}{\overset{R_{551}}{N}}$$

| # | $R_{501}$-N(R_{506})-A- | B | A* | -N(R_{550})(R_{551})... |
|---|---|---|---|---|
| 62. | BzOC(O)NH-CH(iPr)-C(O)- | H | Bz-CH- | -C(OH)(Me)-C(O)OEt |
| 63. | (3-pyridyl)-CH₂-C(O)-NH-CH(iPr)-C(O)- | H | Ph-CH- | -C(OH)(Me)-C(O)OEt |
| 64. | CF₃CONH-CH(iPr)-C(O)- | H | Ph-CH- | -C(OH)(Me)-C(O)OEt |
| 65. | Ph-CH₂-CH₂-C(O)- | H | Bz-CH- | -C(OH)(Me)-C(O)OEt |
| 66. | (4-MeO-C₆H₄)-CH₂-O-C(O)-NH-CH(iPr)-C(O)- | H | Bz-CH- | -C(OH)(Me)-C(O)OEt |
| 67. | (4-MeO-C₆H₄)-C(O)-NH-CH(iPr)-C(O)- | H | Bz-CH- | -C(OH)(Me)-C(O)OEt |
| 68. | Ph-CH₂-C(O)-NH-CH(iPr)-C(O)- | H | Bz-CH- | -C(OH)(Me)-C(O)OEt |
| 69. | (2-pyridyl)-CH₂-O-C(O)-NH-CH(iPr)-C(O)- | H | Bz-CH- | -C(OH)(Me)-C(O)OEt |
| 70. | (2-pyridyl)-CH₂-NH-C(O)-NH-CH(iPr)-C(O)- | H | Bz-CH- | -C(OH)(Me)-C(O)OEt |
| 71. | (2-pyridyl)-CH₂-N(Me)-C(O)-NH-CH(iPr)-C(O)- | H | Bz-CH- | -C(OH)(Me)-C(O)OEt |
| 72. | t-BuOC(O)NH-CH(CH₂CH₂COOH)-C(O)- | H | Bz-CH- | -C(OH)(Me)-C(O)OEt |

TABLE 1-continued

Compounds of formula $$R_{501}\text{-}N(R_{506})\text{-}A\text{-}B\text{-}A^*\text{-}N(R_{550})\text{-}N(R_{551})(R_{502})$$

| # | R₅₀₁-N(R₅₀₆)-A- | B | A*-N(R₅₅₀)- | N(R₅₅₁)(R₅₀₂) / R₅₀₂ |
|---|---|---|---|---|
| 73. | pyridin-2-ylmethyl-N(C(O)NHMe)-C(O)-NH-CH(iPr)-C(O)- | H | Bz, -CH- | OH, -C-, C(O)OEt |
| 74. | 1,2,3-triazol-1-yl-CH₂-C(O)-NH-CH(iPr)-C(O)- | H | Bz, -CH- | OH, -C-, C(O)OEt |
| 75. | tetrazol-1-yl-CH₂CH₂-C(O)-NH-CH(iPr)-C(O)- | H | Bz, -CH- | OH, -C-, C(O)OEt |
| 76. | BzOC(O)NH-CH(iPr)-C(O)- | H | Bz, -CH- | OH, -C-, C(O)OEt |
| 77. | (tetrahydrofuran-2-yl)methyl-OC(O)NH-CH(iPr)-C(O)- | H | Bz, -CH- | OH, -C-, C(O)OEt |
| 78. | HC(O)- | pyrimidin-2-yl | Bz, -CH- | -CH(OH)- |
| 79. | HC(O)- | pyrimidin-2-yl | Bz, -CH- | C(O)CH₃ |
| 80. | CH₃CH₂C(O)- | PhCH₂OCH₂CH₂- | pyridin-4-yl-CH₂, -CH- | OH, -C-, C(O)NHCH₂-(pyridin-2-yl) |
| 81. | MeOC(O)NH-CH(iPr)-C(O)- | H | Bz, -CH- | OH, -C-, C(O)OMe |
| 82. | Me₂NS(O)₂NH-CH(iPr)-C(O)- | H | Bz, -CH- | OH, -C-, C(O)OEt |
| 83. | morpholin-4-yl-NS(O)₂NH-CH(iPr)-C(O)- | H | Bz, -CH- | OH, -C-, C(O)OEt |

TABLE 1-continued

Compounds of formula $$R_{501}R_{506}N-A-B-A^*-N(R_{550})-N(R_{551})R_{502}$$

| # | R₅₀₁ (with R₅₀₆=H via N-A-B-A*) | R₅₀₆ | A* (with R₅₅₀) | R₅₅₁ / R₅₀₂ group |
|---|---|---|---|---|
| 84. | benzyl ester –O–C(O)–CH₂– (PhCH₂O-C(O)-CH₂-) | H | Bz, –CH– | –C(OH)(–)–C(O)OEt |
| 85. | quinoline-2-C(O)NH–CH(iPr)–C(O)– | H | Bz, –CH– | –C(OH)(–)–C(O)OEt |
| 86. | quinoline-2-C(O)NH–CH(CH₂CONH₃)–C(O)– | H | Bz, –CH– | –CH(CH₂OH)– |
| 87. | quinoline-2-C(O)NH–CH(CH₂CONH₃)–C(O)– | H | Bz, –CH– | –CH(CH₂OH)– |
| 88. | quinoline-2-C(O)NH–CH(CH₂CONH₃)–C(O)– | H | –CH(C(O)NH₂)– | –CH(OH)– |
| 89. | quinoline-2-C(O)NH–CH(CH₂CONH₃)–C(O)– | H | –CH(C(O)NH₂)– | acetone (C(O)(CH₃)₂) |
| 90. | PhCH₂O-C(O)-CH₂- | H | Bz, –CH– | –CH(CH₂OH)– |
| 91. | quinoline-2-C(O)NH–CH(CH₂CONH₃)–C(O)– | H | Bz, –CH– | –CH(CH₂OH)– |
| 92. | PhCH₂O-C(O)-CH₂- | H | –CH(C(O)OBz)– | –CH(OH)– |
| 93. | PhCH₂O-C(O)-CH₂- | H | –CH(C(O)OBz)– | acetone (C(O)(CH₃)₂) |

TABLE 1-continued

Compounds of formula $$R_{501}\text{-}N(R_{506})\text{-}A\text{-}B\text{-}A^*\text{-}N(R_{550})\text{-}N(R_{551})(R_{502})$$

| # | R₅₀₁ | R₅₀₆ | R₅₅₀ / A* substituent | R₅₅₁ side |
|---|---|---|---|---|
| 94. | benzyl ester -CH₂-C(O)O-CH₂-Ph | H | Bz, -CH- | -CH- / C(O)OH |
| 95. | benzyl ester | H | Bz, -CH- | -CH(OH)- |
| 96. | benzyl ester | H | Bz, -CH- | -CH(OH)- |
| 97. | quinoline-2-carboxamide-Asn (CONH₃) | H | Bz, -CH- | -CH(OH)- |
| 98. | (pyridin-2-yl)methyl carbamate of 2-acetylcyclohexylamine | H | Bz, -CH- | -CH(OH)- |
| 99. | benzyl ester | H | Bz, -CH- | -CH- / C(O)OEt |
| 100. | quinoline-2-carboxamide-Asn (CONH₃) | H | Bz, -CH- | -CH- / C(O)OEt |
| 101. | quinoline-2-carboxamide-Asn (CONH₃) | H | Bz, -CH- | -CH- / C(O)OEt |
| 102. | benzyl ester | H | Bz, -CH- | -CH- / C(O)OEt |
| 103. | H₂N-C(O)-CH₂-C(O)-CH= | H | Bz, -CH- | -CH(OH)- |

TABLE 1-continued

Compounds of formula $$R_{501}\underset{R_{506}}{N}-A-B-A^*-\underset{R_{550}}{N}-\underset{R_{502}}{\overset{R_{551}}{N}}$$

| No. | Structure (R$_{501}$/R$_{506}$-N-A-B) | R$_{506}$ | A* | R$_{551}$ |
|---|---|---|---|---|
| 104. | quinoline-CONH-CH(CH$_2$CONH$_3$)-C(=O)- | H | Bz / −CH− | Me$_2$C−O / C(Me$_2$)−O (epoxide) |
| 105. | quinoline-CONH-CH(CH$_2$CONH$_3$)-C(=O)- | H | Bz / −CH− | O−C−O / dioxolane |
| 106. | quinoline-CONH-CH(CH$_2$CN)-C(=O)- | H | −CH$_2$−CH− / OS(O)$_2$Me | OMe / −CH− |
| 107. | H$_2$N-C(=O)-CH$_2$-CH(CH$_2$SBu)-C(=O)- | H | Bz / −CH− | −CH(OH)− |
| 108. | furan-C(=O)-NH-CH$_2$-C(=O)- | PhCO | −CH(OH)− | −CH(OH)− |
| 109. | MeO-C$_6$H$_4$-CH$_2$-O-C(=S)- | 3-methylindole | −CH$_2$-C(OH)(CH=CH-Ph)− | −CH(OH)− |

| Compound No. | A* | R$_{550}$ | R$_{551}$ | R$_{502}$ |
|---|---|---|---|---|
| 9. | −CH$_2$− | | −(CH$_2$)$_4$− | t-BuOC(O)− |
| 10. | −CH$_2$− | Et | H | −SO$_2$Me |
| 11. | −CH$_2$− | | cyclohexane-1,2-diyl | t-BuOC(O)− |
| 12. | −CH$_2$− | | cyclohexane-1,2-diyl | t-BuOC(O)− |
| 13. | −CF$_2$CH$_2$− | H | Me | Ac |

TABLE 1-continued

Compounds of formula $$R_{501}(R_{506})N-A-B-A^*-N(R_{550})N(R_{551})(R_{502})$$

| # | A (with R501/R506) | B | A* (with R550) | R551/R502 |
|---|---|---|---|---|
| 14. | -C(OH)(H)-CH₂- | CO₂Me | Pr | H |
| 15. | -CHFCH₂- | Me | Bz | -S(O)₂Ph |
| 16. | -CH(COOMe)- | | (o-xylylene, -CH₂-C₆H₄-CH₂-) | BzC(O)- |
| 17. | -C(Me)₂- | | (cyclopentane-1,2-diylbis(methylene)) | pyridine-2-C(O)NH-CH(iPr)-C(O)- |
| 18. | -CH(2-furyl)- | | (cyclopentane-1,3-diyl) | -S(O)Me |
| 19. | -CH(2-furyl)- | | (cyclopentane-1,3-diyl) | -S(O)Me |
| 20. | -CH(Me)- | i-Pr | i-Pr | H |
| 21. | -CCl₂CH₂- | | (cyclopent-2-ene-1,3-diyl) | -S(O)₂-C₆H₄-CH₃ |
| 22. | -CH(C(O)NH₂)- | Bz | | -(CH₂)₃C(O)- |
| 23. | -CH(C(O)NH₂)- | Bz | | -(CH₂)₃C(O)- |
| 24. | -CF₂CH₂- | -C(O)CH₂NH₂ | | (2-ethylphenyl)C(O)- |
| 25. | -C(=O)CH₃ (acetyl) | Ph | | phthaloyl |
| 26. | -C(Et)₂- | | -C(O)NHC(O)- (imide) | Me |

TABLE 1-continued

Compounds of formula $$R_{501}\underset{R_{506}}{\overset{}{N}}-A-B-A^*-\underset{R_{550}}{\overset{R_{551}}{N}}-N\underset{}{\overset{}{R_{502}}}$$

| | | | | |
|---|---|---|---|---|
| 27. | -CH- attached to thiophene (S) | | o-tolyl-CH₂CH₂- | -S(O)₂NMe₂ |
| 28. | Et-CH- | | -CH₂CH₂C(O)- | -S(O)₂Ph |
| 29. | Ph-CH- | Ac | Ac | Et |
| 30. | C(O)NH₂-CH- | MeOCH₂CH₂ | Ph | pyridine-2-C(O)NH-CH(CH(OH)Me)-C(O)Me |
| 31. | CH₂=CH- | | 1,4-cyclohexyl | quinoline-2-C(O)NH-CH(CH₂Ph)-C(O)Me |
| 32. | -CF₂.CH(CH₃)- | | cyclohex-3-en-1,4-diyl | pyridin-2-yl-CH₂-O-C(O)-NH-CH₂-C(O)- |
| 33. | -CHF.CH(CH₃)- | | 4-oxocyclohex-2-en-1-yl-3-oxo | n-Bu |
| 34. | -CH(COOH)- | | phthaloyl (1,2-benzenedicarbonyl) | n-Pr |
| 35. | -CH(COOH)- | | phthaloyl (1,2-benzenedicarbonyl) | n-Pr |
| 36. | Me₂N-C(O)-CH- | | -(CH₂)₃- | MeOC(O)- |
| 37. | Me₂N-C(O)-CH- | | -(CH₂)₃- | MeOC(O)- |
| 38. | pyridin-2-yl-CH- | | 4,5-diethyl-hexahydropyridazine (HN-NH) | NH₂-CH(Et)-C(O)- |

TABLE 1-continued
Compounds of formula
$$R_{501}\text{-}\underset{R_{506}}{N}\text{-}A\text{-}B\text{-}A^*\text{-}\underset{R_{550}}{N}\text{-}\underset{}{N}\underset{R_{502}}{\overset{R_{551}}{}}$$
| # | | | | |
|---|---|---|---|---|
| 39. | —CCl₂CH—<br>\|<br>CH₃ | S(O)NMe₂ | S(O)NMe₂ | 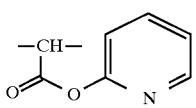 |
| 40. | 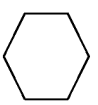 |  | 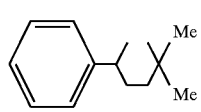 | —S(O)₂OCH₃ |
| 41. | —CH₂ | Bz | H | t-BuOC(O)— |
| 42. | —CH(Et)— | | 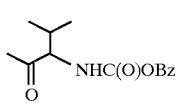 |  |
| 43. | —CH₂ | | 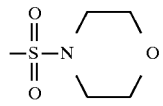 | 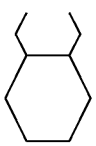 |
| 44. | —CH₂ | | 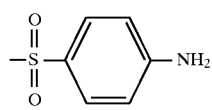 | 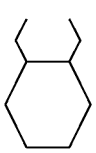 |
| 45. | —CH₂ | | 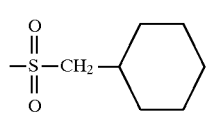 | 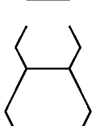 |
| 46. | —CH₂ | | 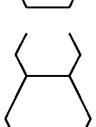 | —S(O)₂OBz |
| 47. | —CH₂ | | 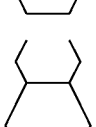 | —S(O)OBuᵗ |
| 48. | —CH₂ | | 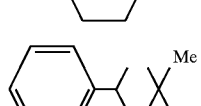 | —S(O)₂NH₂ |
| 49. | —CH(Et)— | | 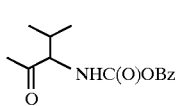 | NHC(O)OBz |
| 50. | —CH₂— | Bz | H | t-BuOC(O)— |

TABLE 1-continued
Compounds of formula
$$R_{501}\underset{R_{506}}{\overset{}{N}}-A-B-A^*-\underset{R_{550}}{\overset{R_{551}}{N}}-N\underset{}{\overset{}{R_{502}}}$$
| | | | | |
|---|---|---|---|---|
| 51. | —CH$_2$— | 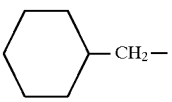 | H | t-BuOC(O)— |
| 52. | —CH$_2$— | 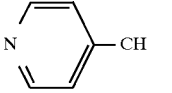 | 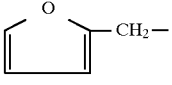 | t-BuOC(O)— |
| 53. | —CH$_2$— | | 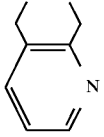 | 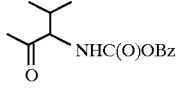 |
| 54. | —CH$_2$— | |  | 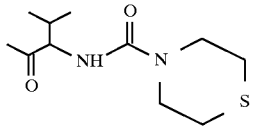 |
| 55. | —CH$_2$— | |  | 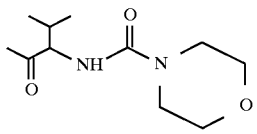 |
| 56. | Bz<br>\|<br>—CH— | H | H | 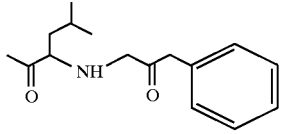 |
| 57. | Bz<br>\|<br>—CH— | H | H | 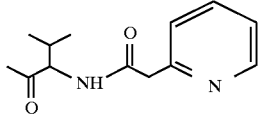 |
| 58. | —CH$_2$— | 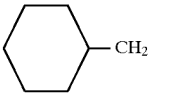 | H | 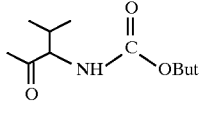 |
| 59. | —CH(i-Pr)— | | 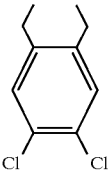 |  —CCH$_2$Ph |
| 60. | —CH$_2$— | |  | 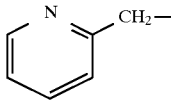 |

TABLE 1-continued

Compounds of formula $$R_{501}\diagdown_{N}\diagup^{A}\diagdown_{B}\diagdown^{A^*}\diagdown_{N}\diagup^{R_{551}}_{R_{502}}$$
$$R_{506} \quad\quad\quad R_{550}$$

| # | | | | |
|---|---|---|---|---|
| 61. | —CH₂— | | (cyclohexanone) | (pyridin-2-yl)CH₂— |
| 62. | —CH₂— | Bz | H | BzOC(O)— |
| 63. | —CH₂— | Bz | H | (pyridyl-CH₂-C(O)NH-CH(iPr)-C(O)-Me) |
| 64. | —CH₂— | Bz | H | CF₃CONH-CH(iPr)-C(O)-Me |
| 65. | —CH₂— | Bz | H | (PhCH₂CH₂C(O)—) |
| 66. | —CH₂— | Bz | H | MeO-C₆H₄-CH₂-O-C(O)-NH-CH(iPr)-C(O)-Me |
| 67. | —CH₂— | Bz | H | MeO-C₆H₄-C(O)-NH-CH(iPr)-C(O)-Me |
| 68. | —CH₂— | Bz | H | PhCH₂C(O)—NH-CH(iPr)-C(O)-Me |
| 69. | —CH₂— | Bz | H | (pyridin-2-yl)CH₂-O-C(O)-NH-CH(iPr)-C(O)-Me |
| 70. | —CH₂— | Bz | H | (pyridin-2-yl)CH₂-NH-C(O)-NH-CH(iPr)-C(O)-Me |
| 71. | —CH₂— | Bz | H | (pyridin-2-yl)CH₂-N(Me)-C(O)-NH-CH(iPr)-C(O)-Me |
| 72. | —CH₂— | Bz | H | t-BuOC(O)NH-CH(CH₂COOH)-C(O)-Me |

TABLE 1-continued

Compounds of formula $$R_{501}\text{-}N(R_{506})\text{-}A\text{-}B\text{-}A^*\text{-}N(R_{550})\text{-}N(R_{551})(R_{502})$$

| # | | | | |
|---|---|---|---|---|
| 73. | —CH$_2$— | Bz | H | pyridin-2-yl-CH$_2$-N(C(O)NHMe)-C(O)-NH-CH(iPr)-CHO |
| 74. | —CH$_2$— | Bz | H | (1,2,3-triazol-1-yl)-CH$_2$-C(O)-NH-CH(iPr)-C(O)- |
| 75. | —CH$_2$— | Bz | H | (tetrazol-1-yl)-CH$_2$CH$_2$-C(O)-NH-CH(iPr)-C(O)- |
| 76. | —CH$_2$— | Bz | H | BzOC(O)NH-CH(sBu)-C(O)- |
| 77. | —CH$_2$— | Bz | H | (tetrahydrofuran-2-yl)-CH$_2$-OC(O)NH-CH(iPr)-C(O)- |
| 78. | —CH$_2$— | | 4,5-diethylpyrimidine | CH$_3$C(O)-CH(CH$_2$Ph)-C(O)NH$_2$ |
| 79. | —CH$_2$— | | 4,5-diethylpyrimidine | CH$_3$C(O)-CH(CH$_2$Ph)-C(O)NH$_2$ |
| 80. | (pyridin-4-yl)-CH— | | Ph-CH(Et)-CH(Et)-Ph | CH$_3$CH$_2$C(O)- |
| 81. | —CH$_2$— | Bz | H | MeOC(O)NH-CH(iPr)-C(O)- |
| 82. | —CH$_2$— | Bz | H | Me$_2$NS(O)$_2$NH-CH(iPr)-C(O)- |
| 83. | —CH$_2$— | Bz | H | morpholino-NS(O)$_2$NH-CH(iPr)-C(O)- |

TABLE 1-continued

Compounds of formula $$R_{501}\text{-}N(R_{506})\text{-}A\text{-}B\text{-}A^*\text{-}N(R_{550})\text{-}N(R_{551})(R_{502})$$

| # | | | | |
|---|---|---|---|---|
| 84. | —CH$_2$— | i-Pr | H | t-BuOC(O)— |
| 85. | —CH$_2$— | i-Pr | H | t-BuOC(O)— |
| 86. | —CH$_2$— | i-Pr | H | t-BuOC(O)— |
| 87. | —CH$_2$— | Bz | H | (piperidin-2-yl)methyl N-(3-acetylphenyl)carbamate |
| 88. | —CH$_2$— | Bz | H | t-BuOC(O)— |
| 89. | —CH$_2$— | Bz | H | t-BuOC(O)— |
| 90. | —CH$_2$— | 3-methyl-1-phenyl-1-butenyl | H | t-BuOC(O)— |
| 91. | —CH$_2$— | 3-methyl-1-phenyl-1-butenyl | H | t-BuOC(O)— |
| 92. | —CH$_2$— | —CH$_2$CF$_3$ | H | t-BuOC(O)— |
| 93. | —CH$_2$— | —CH$_2$CF$_3$ | H | t-BuOC(O)— |
| 94. | —CH$_2$— | o-diethylbenzene | | t-BuOC(O)— |
| 95. | —CH$_2$— | phthaloyl | | i-Pr |
| 96. | —CH$_2$— | diethyl-tetrazinyl | | i-Pr |
| 97. | —CH$_2$— | diethyl-succinimidyl | | t-BuOC(O)— |
| 98. | —CH$_2$— | tetrahydrofuran-2,5-diyl | | t-BuOC(O)— |
| 99. | —CH$_2$— | Bz | H | t-BuOC(O)— |
| 100. | —CH$_2$— | Bz | H | t-BuOC(O)— |

TABLE 1-continued

Compounds of formula

R501\N(R506)-A-B-A*-N(R550)-N(R551)(R502)

| | R501-N-A | B | A*-N-R550 | N-R502 (R551) |
|---|---|---|---|---|
| 101. | —CH₂— | H-N(piperidine)-CH₂— | H | t-BuOC(O)— |
| 102. | —CH₂— | H-N(piperidine)-CH₂— | H | t-BuOC(O)— |
| 103. | —CH₂— | i-Pr | H | —C(O)—NMe₂ |
| 104. | —CH₂— | i-Pr | H | t-BuOC(O)— |
| 105. | —CH₂— | i-Pr | H | t-BuOC(O)— |
| 106. | —CH—CH₂— <br> \|<br>OS(O)₂Me | isohexyl (2,4-dimethylpentyl) | | —C(O)-morpholine |
| 107. | —CH₂— | 3,5-dimethylpiperidine (N-H) | | BzOC(O)— |
| 108. | —CH(OH)— | N-Me-2,5-dimethylpyrrolidine | Me | —C(O)SMe |
| 109. | OH<br>\|<br>—C—CH₂—<br>\|<br>(CH=CH-Ph) | 2,3-disubstituted naphthalene | | —C(O)O-(4-chlorophenyl) |

TABLE 2

Compound of formula W—(A)$_n$—B—(A*)$_m$—V

| Compound No | W | (A)$_n$ | B | (A*)$_m$ | V |
|---|---|---|---|---|---|
| 110. | quinoline-2-carboxamide-Val-OMe derivative | —CH(Bz)— | —N(OH)— | —CH$_2$— | —N(—)—C(O)—OBu$^t$ (decahydronaphthalene) |
| 111. | quinoline-2-carboxamide-Asn derivative | — | >C=O | —CH$_2$— | —N(—)—S(=O)—OBu$^t$ (decahydronaphthalene) |
| 112. | BzC(O)O—N(iPr)— | —CH$_2$—CH(Bz)—CH$_2$—CH$_2$—CH$_2$— | —CH(OH)— | Bz—CH(—)—CH$_2$— (pyrrolidine) | —N(iPr)—OC(O)Bz |
| 113. | Ph$_2$C=N— | — | >S=O | | —N=N—Ph |
| 114. | HO—N=C(CH$_3$)— | —CH(—)—CH$_2$—C$_6$H$_4$—OCH$_3$ | —CH(NH$_2$)— | —CH(—)—(1,2,3,4-tetrahydronaphthalen-1-yl) | —NH—S(O)$_2$—C$_6$H$_4$—CH$_3$ |

TABLE 2-continued

Compound of formula W—(A)$_n$—B—(A*)$_m$—V

| Compound No | W | (A)$_n$ | B | (A*)$_m$ | V |
|---|---|---|---|---|---|
| 115. | (2-pyridyl-CH$_2$-NHC(O)-) | Bz-C(CH$_3$)- | (CH$_2$)$_2$OH, —N— | —CH—CH$_2$—C(O)NH$_2$ | —O—S(O)$_2$—Ph |
| 116. | PhC(O)NH— | —CH—CH$_2$—CH$_2$C(O)OMe | —N— | —C(O)—CH$_2$— | Et-N(Me)-C(O)-OMe |
| 117. | (quinolinyl) | —CH$_2$—CH$_2$— | Me$_2$N—N— | —CH$_2$—CH$_2$— | Ph-N(Me)-N-CH=CH-Ph (cyclic) |
| 118. | MeO-P(O)(Me)- | —CH$_2$—CH—C(O)OBz | —NH— | —CH—CH$_2$—C(O)Bz | PhCH$_2$-NHC(O)-O-CH(CH$_2$OMe)-C(O)-NH-OMe (2-pyridyl-CH$_2$-O-) |
| 119. | 4-H$_3$C-C$_6$H$_4$-S(O)$_2$-NHC(O)NH— | Bz-CH— | —CH—O—(CHOH)$_3$—CH$_2$OH | —CH$_2$— | Et-N(CH$_2$-piperidin-4-yl-NH)-N(Me)-C(O)OBu$^t$ |

TABLE 2-continued

Compound of formula W—(A)$_n$—B—(A*)$_m$—V

| Compound No | W | (A)$_n$ | B | (A*)$_m$ | V |
|---|---|---|---|---|---|
| 120. | quinoline-2-carbonyl-Val-NH— | —CH(COOMe)— | C(Me)=N-OH | —CH$_2$— | decahydronaphthalene-N(Me)-C(O)-OBu$^t$ |
| 121. | quinoline-2-carbonyl-Val-NH— | —CH(COOMe)— | C(Me)=N-NH$_2$ | —CH$_2$— | decahydronaphthalene-N(Me)-C(O)-OBu$^t$ |
| 122. | —CN | —(CH$_2$)$_2$O(CH$_2$)$_2$O— | C=O | —CH$_2$CH$_2$— | C(Me)=N-OH |
| 123. | MeOC(O)— | —CH$_2$CH$_2$— | C=O | —O(CH$_2$)$_2$O(CH$_2$)$_2$— | —N$^+$=N—Bu (O$^-$) |
| 124. | —CN | —N(Me)CH$_2$CH$_2$CH$_2$CH$_2$— (with OMe) | C=O | —CH$_2$CH$_2$— | C(Me)=N-OH |
| 125. | (oxazoline Me,Me,Me,Me with N-Me and acetyl side chain) | —O— | —(CH$_2$)$_2$CH(Me)— | —OS(O)$_2$CH$_2$Ph | |

TABLE 2-continued

Compound of formula W—(A)$_n$—B—(A*)$_m$—V

| Compound No | W | (A)$_n$ | B | (A*)$_m$ | V |
|---|---|---|---|---|---|
| 126. | quinoline-Val-NH- group | —CH(COOMe)— | N=C(Ph)— | —CH$_2$— | N-CH$_2$-decalin-CH$_2$-N-C(O)OBu$^t$ |
| 127. | Et-N-Bz | —CH(OS(O)$_2$Me)— | N=C(OH)— | —CH=CH— | N-N-cyclopentane-S(O)Me |
| 128. | Et-N-Bz | —CH(OS(O)$_2$Me)— | N=C(NH$_2$)— | —CH=CH— | N-N-cyclopentane-S(O)Me |
| 129. | H$_2$N-C(O)-N(CH$_2$COOH)— | —CH(1-naphthyl)— | N=C(OC(O)Ph)— | —CH(COOH)— | N(Pr)-N-C(O)-cyclohexane-C(O) |
| 130. | H$_2$N-C(O)-N(CH$_2$COOH)— | —CH(1-naphthyl)— | N=C(NHPh)— | —CH(COOH)— | N(Pr)-N-C(O)-cyclohexane-C(O) |

TABLE 2-continued

Compound of formula W—(A)ₙ—B—(A*)ₘ—V

| Compound No | W | (A)ₙ | B | (A*)ₘ | V |
|---|---|---|---|---|---|
| 131. | | Bz | | | |
| 132. | | | | | |
| 133. | | | | — | |
| 134. | | | | | |
| 135. | | | | | |

TABLE 2-continued

Compound of formula W—(A)$_n$—B—(A*)$_m$—V

| Compound No | W | (A)$_n$ | B | (A*)$_m$ | V |
|---|---|---|---|---|---|
| 136. | morpholine-N— | succinimide (N-H) with methyl substituents | —S(O)$_2$— | —O-decahydronaphthalene-O— | —S(O)$_2$NMe$_2$ |
| 137. | quinolin-2-yl-C(O)NH-CH(CH$_2$C(O)NH$_2$)-C(O)NH— | —CH$_2$—C(=C(CO$_2$Me))(CO$_2$M4e)— | —CH(OH)— | —CH$_2$— | N-carbamate (OBu$^t$) on decahydronaphthalene-bis(CH$_2$N) |
| 138. | quinolin-2-yl-C(O)NH-CH(CH$_2$C(O)NH$_2$)-C(O)NH— | —CH(Bz)— | —CH(OH)— | BzC(O)O—N(iPr)— | N-carbamate (OBu$^t$) on decahydronaphthalene-bis(CH$_2$N) |
| 139. | quinolin-2-yl-C(O)NH-CH(CH$_2$C(O)NH$_2$)-C(O)NH— | —CH(Bz)— | —CH(OH)— | —CH$_2$— | —N(Pr)—N=C(Me)Me |

TABLE 2-continued

Compound of formula W—(A)$_n$—B—(A*)$_m$—V

| Compound No | W | (A)$_n$ | B | (A*)$_m$ | V |
|---|---|---|---|---|---|
| 140. | Ph\C=N—<br>Me/ | —CH$_2$CH$_2$— | O=C\ | —CH$_2$CH$_2$— | cyclohexyl-CH$_2$—N—N=C(Ph)(Me) |

TABLE 3
Examples of Other Compounds of Formula (I)
141.
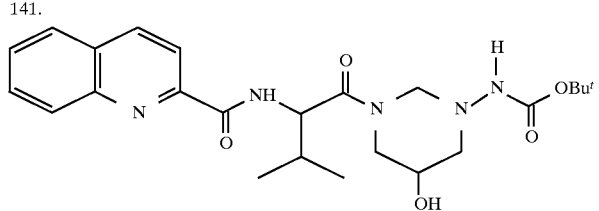
142.
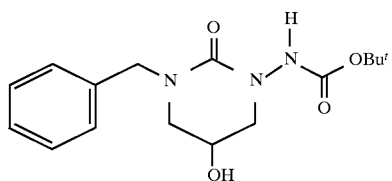
143.
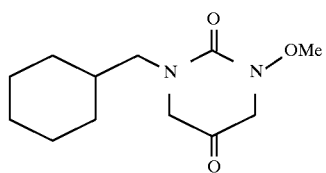
144.
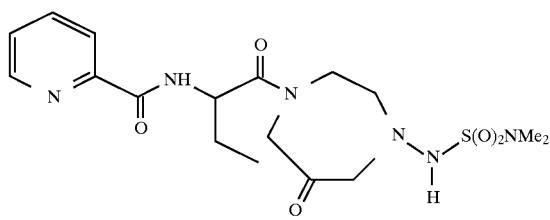
145.
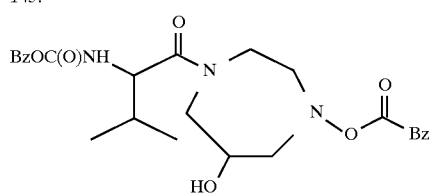
146.
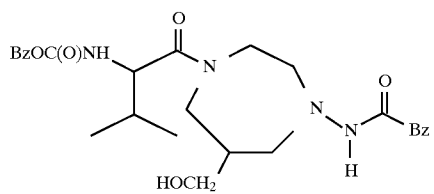
147.
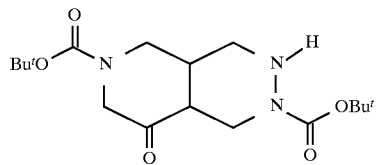
148.

-continued
TABLE 3
Examples of Other Compounds of Formula (I)
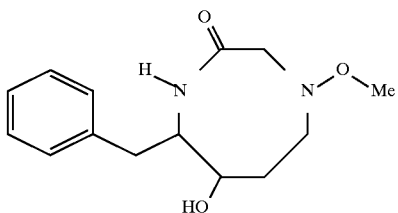
149.
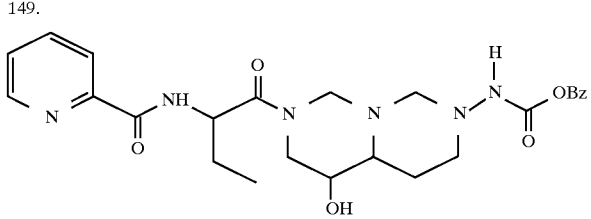
150.
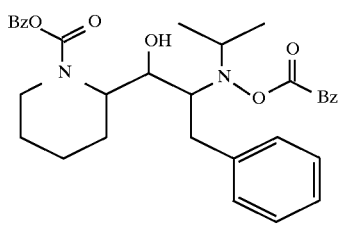
151.
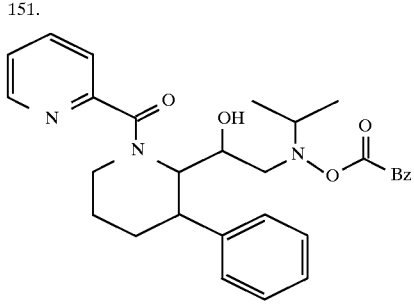
152.
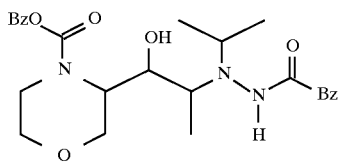
153.
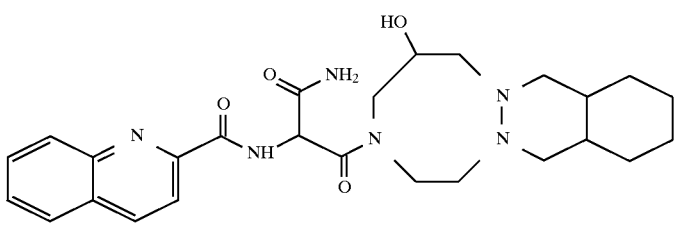
154.

-continued
TABLE 3
Examples of Other Compounds of Formula (I)
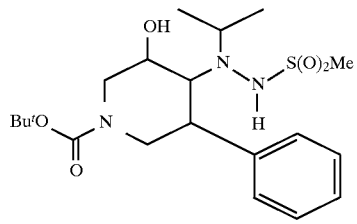
155.
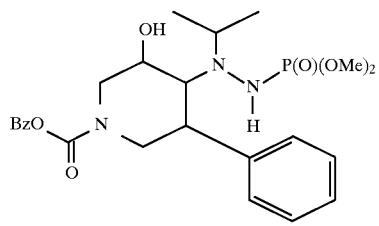
156.
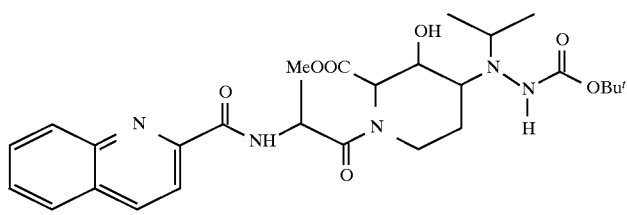
157.
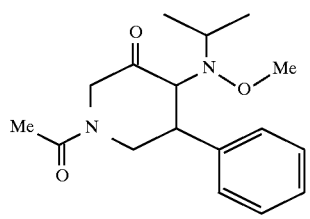
158.
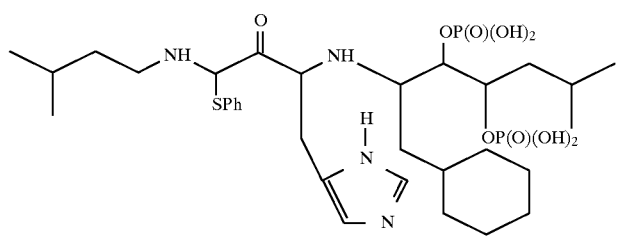
159.
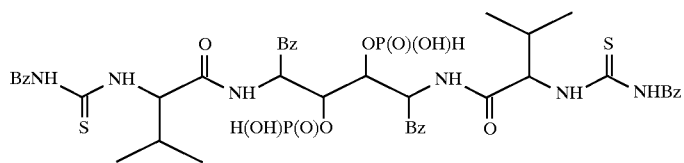
160.

-continued
TABLE 3
Examples of Other Compounds of Formula (I)
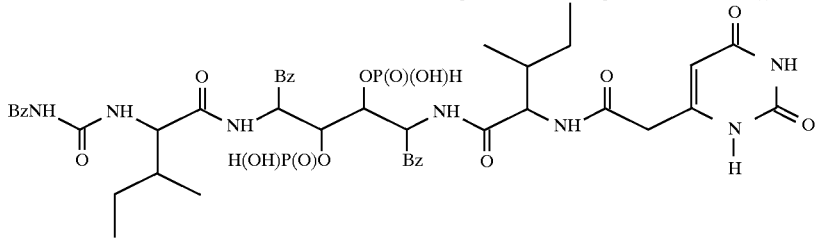
161.
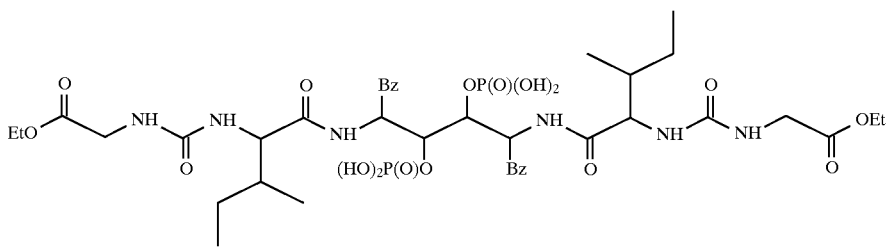
162.
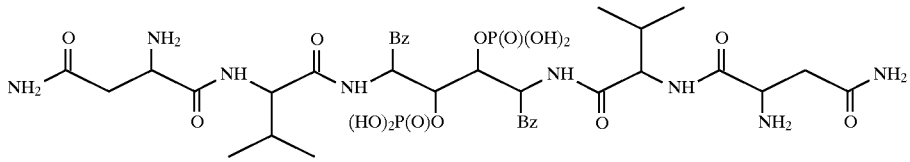
163.
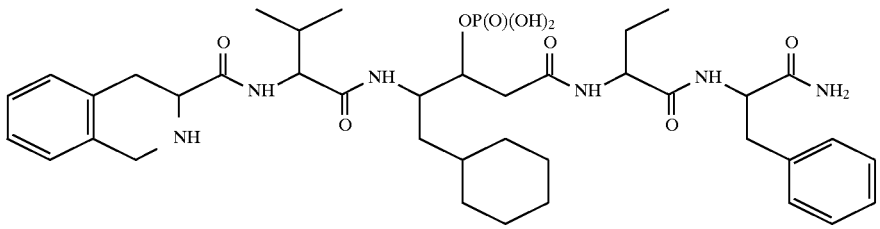
164.
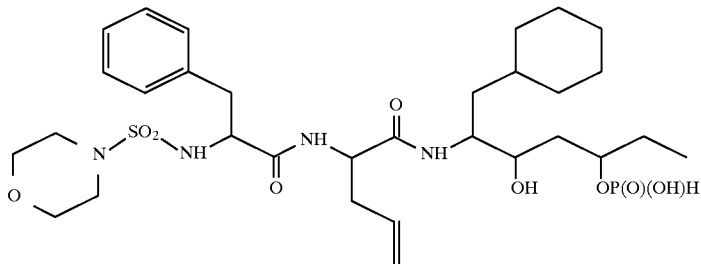
165.
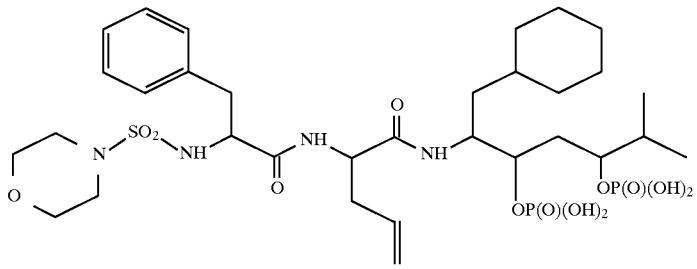
166.

-continued
TABLE 3
Examples of Other Compounds of Formula (I)
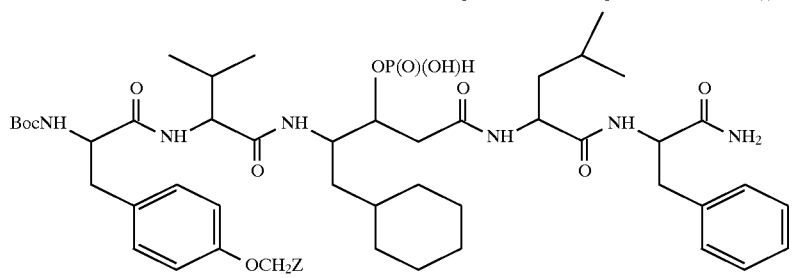
167.
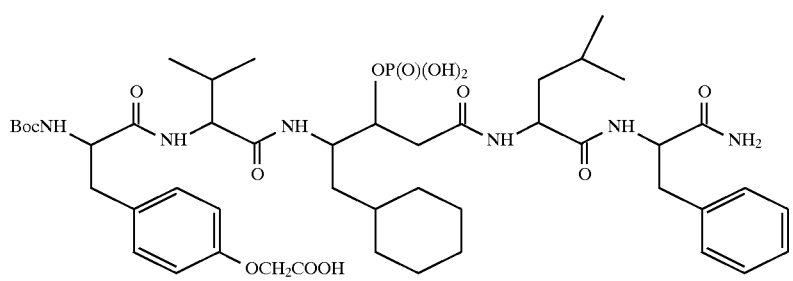
168.
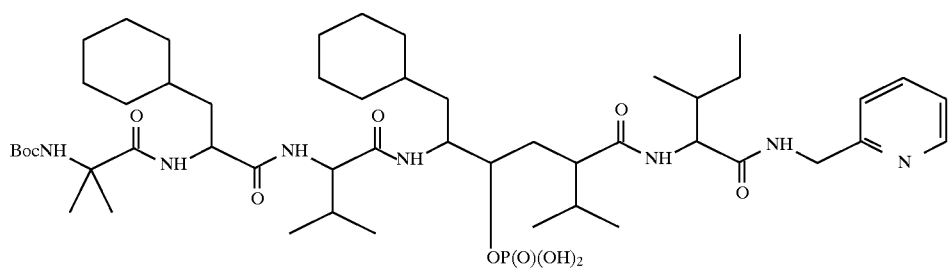
169.
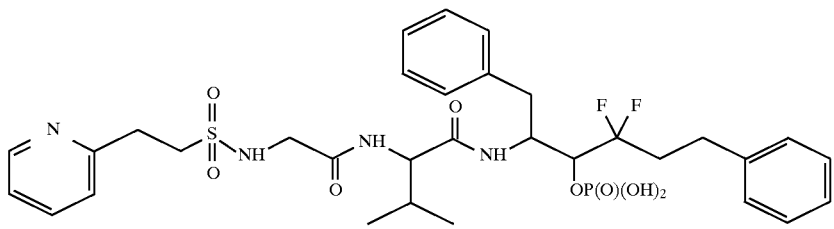
170.
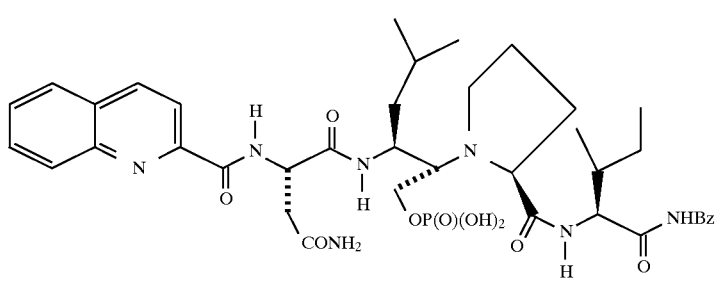
171.

-continued
TABLE 3
Examples of Other Compounds of Formula (I)
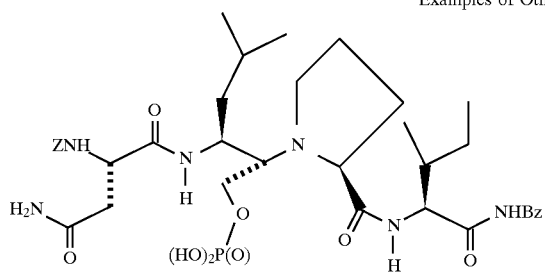
172.
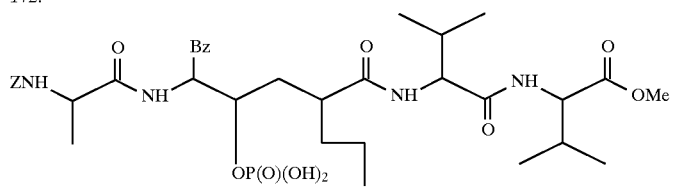
173.
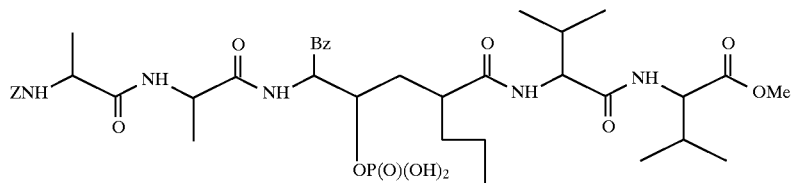
174.
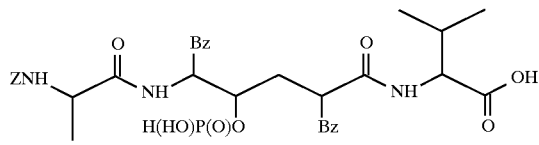
175.
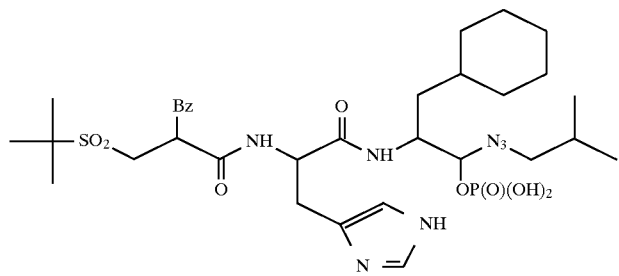
176.
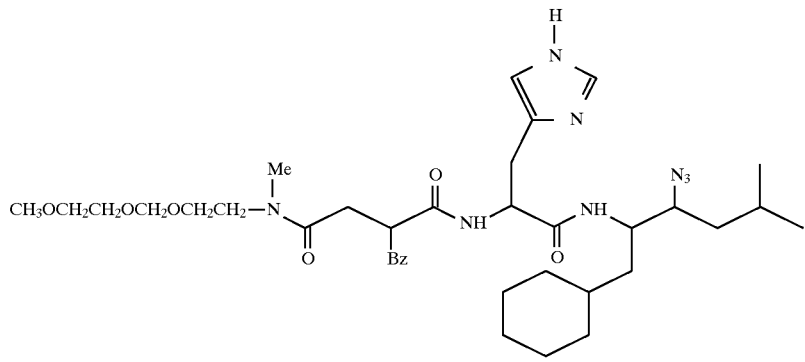
177.

-continued
TABLE 3
Examples of Other Compounds of Formula (I)
178. 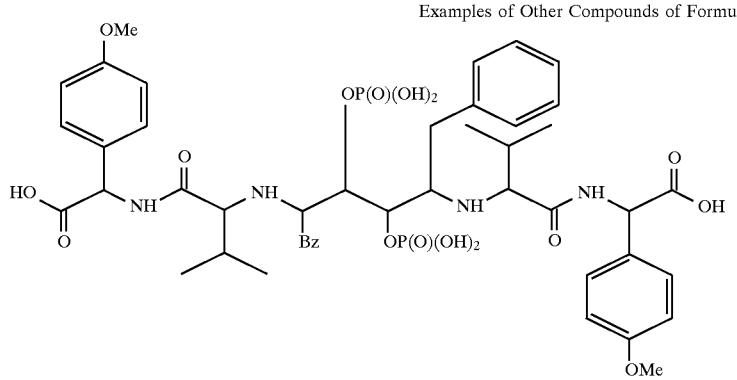
179. 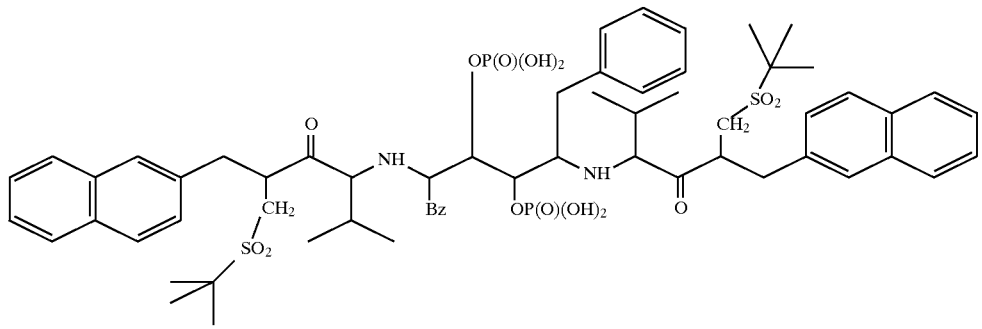
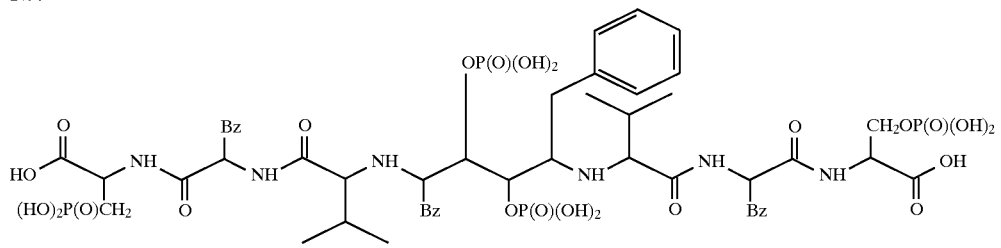
180. 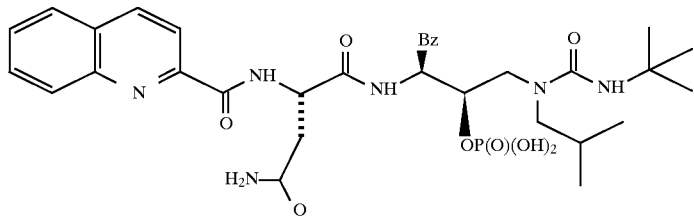
181. 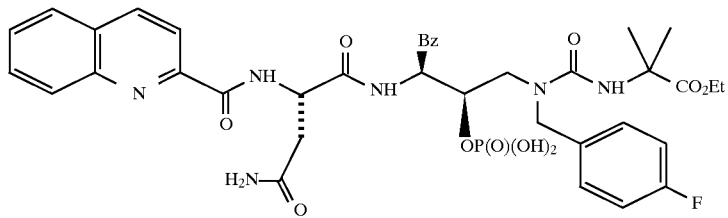

TABLE 4

Compounds of formula $$R_{501}-N(R_{506})-C(R_{12})(H)-C(H)(OPx)-C(H)(R_{550})-N(R_{551})(R_{502})$$

| Compound No. | $R_{501}$ | $R_{506}$ | $R_{12}$ | Px | $R_{550}$ | $R_{551}$ | $R_{502}$ |
|---|---|---|---|---|---|---|---|
| 182. | Z | H | Bz | P(O)(OH)$_2$ | i-Pr | H | Boc |
| 183. | Z | H | Bz | P(S)(OH)$_2$ | | | Boc |
| 184. | Z | H | Bz | P(O)(OH)$_2$ | (cyclopentenyl) | | Boc |
| 185. | Z | H | Bz | P(O)(OH)$_2$ | (cyclopentyl) | | Boc |
| 186. | Z | H | Bz | HP(O)(OH) | i-Pr | H | Boc |
| 187. | Z | H | Bz | HP(O)(OH) | Bz | H | —C(O)Bu$^t$ |
| 188. | Z | H | Bz | P(O)(OH)$_2$ | C$_6$H$_{11}$ | H | Boc |
| 189. | Z | H | Bz | P(O)(OH)$_2$ | i-Pr | —(CH$_2$)$_4$— | Boc |
| 190. | Z | H | Bz | (pyrophosphate —OP(O)(OH)OP(O)(OH)—) | Bz | H | Z |
| 191. | Z—Val | H | Bz | —SCH$_2$C(O)CH$_2$— with COOH | Bz | H | Z—Val |

TABLE 4-continued

Compounds of formula $$R_{501}-N\begin{array}{c}R_{506}\\|\\C\\|\\H\end{array}\begin{array}{c}R_{12}\\|\\C\\|\\H\end{array}\begin{array}{c}H\\|\\C\\|\\OPx\end{array}\begin{array}{c}R_{551}\\|\\N-N\\|\\R_{550}\end{array}R_{502}$$

| Compound No. | $R_{501}$ | $R_{506}$ | $R_{12}$ | Px | $R_{550}$ | $R_{551}$ | $R_{502}$ |
|---|---|---|---|---|---|---|---|
| 192. | Z—Val | H | Bz | | $CH_2C_6H_{11}$ | H | Z—Val |
| 193. | Z—Val | H | Bz | | (p-F)Bz | H | Boc |
| 194. | Z—Val | H | Bz | | (p-F)Bz | H | Boc—Val |
| 195. | Z—Val | H | Bz | | (p-F)Bz | H | Val |
| 196. | Z—Val | H | Bz | | (p-F)Bz | H | MC—Gly—Val |
| 197. | Z—Val | H | (p-F)Bz | ![](pentanoic acid ketone) | (p-F)Bz | H | Boc |
| 198. | Z—Val | H | (p-F)Bz | ![](pentanoic acid ketone) | (p-F)Bz | H | H |

TABLE 4-continued
Compounds of formula
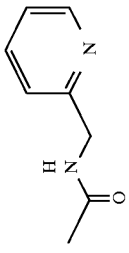
| Compound No. | $R_{501}$ | $R_{506}$ | $R_{12}$ | Px | $R_{550}$ | $R_{551}$ | $R_{502}$ |
|---|---|---|---|---|---|---|---|
| 199. | Z—Val | H | (p-F)Bz | 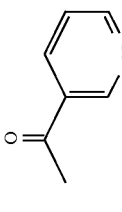 | (p-F)Bz | H |  |
| 200. | Z—Val | H | (p-F)Bz | 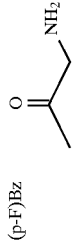 | (p-F)Bz | H | 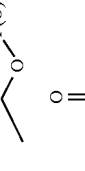 |
| 201. | Z—Val | H | Bz | 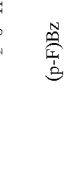 | $CH_2C_6H_{11}$ | H | TMC—Val |
| 202. | Z—Val | H | Bz |  | (p-F)Bz | H | Z—Val |
| 203. | Z—Val | H | Bz | 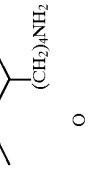 | (p-CN)Bz | H | Z—Val |
| 204. | Z—Val | H | Bz | 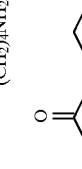 | 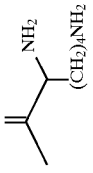 | H | 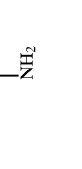 |

TABLE 4-continued

Compounds of formula $$\begin{array}{c} R_{501}\text{–}N\text{–}C\text{–}C\text{–}C\text{–}N\text{–}R_{502} \\ R_{506}\ R_{12}\ H\ OPx\ R_{550} \end{array}$$

| Compound No. | R$_{501}$ | R$_{506}$ | R$_{12}$ | Px | R$_{550}$ | R$_{551}$ | R$_{502}$ |
|---|---|---|---|---|---|---|---|
| 205. | Z—Val | H | Bz | (arginine-like ketone) | n-Bu | H | (isopropyl ketoamide with morpholinoethyl) |
| 206. | Z—Val | H | Bz | (arginine-like ketone) | n-Bu | H | (triazolyl propyl ketoamide) |
| 207. | Z—Val | H | Bz | (arginine-like ketone) | n-Bu | H | (isopropyl ketoamide with pyridylethyl) |
| 208. | Z—Val | H | Bz | P(O)(OH)$_2$ | (p-F)Bz | H | (triazolyl propionamide with isopropyl ketone) |
| 209. | Z—Val | H | (p-F)Bz | (p-acetylphenyl-OP(O)(OH)$_2$) | (p-F)Bz | H | (isopropyl ketoamide with morpholinoethyl) |

TABLE 4-continued

Compounds of formula

| Compound No. | R_501 | R_506 | R_12 | Px | R_550 | R_551 | R_502 |
|---|---|---|---|---|---|---|---|
| 210. | Z—Val | H | (p-F)Bz | (acetyl-phenoxy-P(O)(OH)_2) | (p-F)Bz | H | (isopropyl-ketone-amide-ethyl-pyridine) |
| 211. | Z—Val | H | (p-F)Bz | P(O)(OH)_2 | (p-F)Bz | H | MC—Gly—Val |
| 212. | Z—Asn | H | Bz | P(O)(OH)_2 | (p-F)Bz | H | Boc |
| 213. | Z—Asn | H | Bz | P(O)(OH)_2 | (p-F)Bz | H | Z—Val |
| 214. | Z—Asn | H | Bz | P(O)(OH)_2 | Bz | H | Boc |
| 215. | Z—Ile | H | Bz | P(S)(OH)_2 | (isobutyl) | H | Z—Ile |
| 216. | Z—Glu | H | Bz | (oxy-acetic acid) | (p-F)Bz | H | Z—Glu |
| 217. | QC—Val | H | Bz | P(O)(OH)_2 | i-Pr | H | Boc |
| 218. | QC—Val | H | Bz | P(O)(OH)_2 | (decalin) | H | Boc |
| 219. | QC—Val | H | Bz | HP(O)(OH) | Bz | H | QC—Val |
| 220. | QC—Asn | H | Bz | HP(O)(OH) | i-Pr | H | Boc |

TABLE 4-continued

Compounds of formula $$\begin{array}{c} R_{501}\diagdown N - C - N \diagup R_{551} \\ R_{506} \phantom{xx} R_{12} \phantom{xx} H \phantom{xx} R_{502} \\ H - C - C - H \\ \phantom{xx} H \phantom{xx} OPx \phantom{xx} R_{550} \end{array}$$

| Compound No. | $R_{501}$ | $R_{506}$ | $R_{12}$ | Px | $R_{550}$ | $R_{551}$ | $R_{502}$ |
|---|---|---|---|---|---|---|---|
| 221. | QC—Asn | H | Bz | P(O)(OH)$_2$ | i-Pr | H | [2-(pyridylmethoxycarbonylamino)-phenyl acetate group] |
| 222. | QC—Asn | H | Bz | HP(O)(OH) | i-Pr | H | [2-(pyridylmethoxycarbonylamino)-phenyl acetate group] |
| 223. | QC—Asn | H | Bz | P(O)(OH)$_2$ | i-Pr | H | Boc |
| 224. | QC—Asn | H | Bz | P(O)(OH)$_2$ | i-Pr | H | QC—Val |
| 225. | QC—Asn | H | Bz | [4-oxopentanoic acid group] | CH$_2$CH$_2$CH(CH$_3$)CH$_2$Ph | H | Boc |
| 226. | QC—Asn | H | Bz | P(O)(OH)$_2$ | [diethylcyclohexyl group] | | Boc |

TABLE 4-continued
Compounds of formula
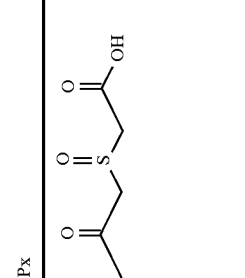
| Compound No. | $R_{501}$ | $R_{506}$ | $R_{12}$ | Px | $R_{550}$ | $R_{551}$ | $R_{502}$ |
|---|---|---|---|---|---|---|---|
| 227. | QC—Asn | H | Bz | 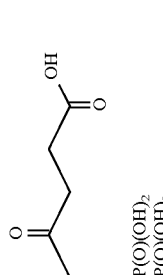 | 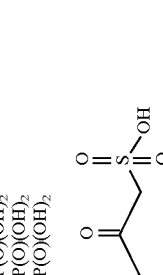 | | Boc |
| 228. | QC—Asn | H | Bz | 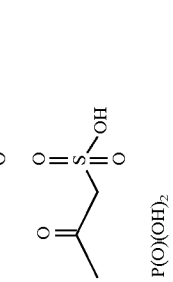 | i-Pr | H | —C(O)Bu$^t$ |
| 229. | QC—Asn | H | Bz | P(O)(OH)$_2$ | i-Pr | H | —C(O)NHBu$^t$ |
| 230. | QC—Asn | H | Bz | P(O)(OH)$_2$ | Bz | H | Boc |
| 231. | QC—Asn | H | Bz | P(O)(OH)$_2$ | C$_6$H$_{11}$ | H | Boc |
| 232. | QC—Asn | H | Bz | P(O)(OH)$_2$ | —(CH$_2$)$_4$— | | |
| 233. | QC—Asn | H | Bz |  | (p-F)Bz | H | Boc |
| 234. | QC—Asn | H | (p-F)Bz |  | Bz | H | QC—Val |
| 235. | QC—Asn | H | Bz | P(O)(OH)$_2$ | |  | Boc |

TABLE 4-continued

Compounds of formula $$R_{501}-N-C(R_{12})(H)-C(H)(R_{506})-C(H)(OPx)-N(R_{550})-N(R_{551})(R_{502})$$

| Compound No. | $R_{501}$ | $R_{506}$ | $R_{12}$ | Px | $R_{550}$ | $R_{551}$ | $R_{502}$ |
|---|---|---|---|---|---|---|---|
| 236. | QC—Thr | H | Bz | $P(O)(OH)_2$ | decalinyl | | Boc |
| 237. | QC—(CN)Ala | H | Bz | $P(O)(OH)_2$ | decalinyl | | Boc |
| 238. | BzC(O) | H | Bz | $P(O)(OH)_2$ | (CH$_3$)$_2$CHCH=CH(Ph) | H | Boc |
| 239. | BzC(O)—Val | H | Bz | $P(O)(OH)_2$ | Bz | H | BzC(O)—Val |
| 240. | PC—Val | H | Bz | $P(O)(OH)_2$ | decalinyl | | Boc |
| 241. | PC—Val | H | Bz | $P(O)(OH)_2$ | cyclopentyl | | Boc |

TABLE 4-continued

Compounds of formula

| Compound No. | $R_{501}$ | $R_{506}$ | $R_{12}$ | Px | $R_{550}$ | $R_{551}$ | $R_{502}$ |
|---|---|---|---|---|---|---|---|
| 242. | PC—Val | H | Bz | $P(O)(OH)_2$ | 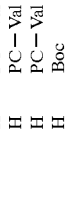 | | —C(O)NH |
| 243. | PC—Val | H | Bz | $P(O)(OH)_2$ | Bz | H | PC—Val |
| 244. | PC—Val | H | Bz | $P(O)(OH)_2$ | i-Pr | H | PC—Val |
| 245. | PC—Val | H | Bz | $P(O)(OH)_2$ | $CH_2C_6H_{11}$ | H | PC—Val |
| 246. | PC—Asn | H | Bz | $P(O)(OH)_2$ | i-Pr | H | Boc |
| 247. | H | H | Bz | $P(O)(OH)_2$ | 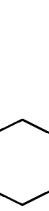 | | Boc |
| 248. | Val | H | Bz | $P(O)(OH)_2$ | Bz | H | Val |
| 249. | Val | H | Bz | $P(O)(OH)_2$ | $CH_2C_6H_{11}$ | H | Val |
| 250. | Val | H | Bz | $P(O)(OH)_2$ |  | H | Val |
| 251. | Boc | H | Bz | $P(O)(OH)_2$ | Bz | H | Boc |
| 252. | Boc | H | Bz | $S(O)_2OH$ | $CH_2C_6H_{11}$ | H | Boc |
| 253. | Boc | H | Bz | $B(OH)_2$ | i-Pr | H | Boc |
| 254. | Boc—Val | H | Bz | $S(O)_2OH$ | $CH_2C_6H_{11}$ | H | Boc—Val |
| 255. | Boc—Val | H | Bz | $P(O)(OH)_2$ | 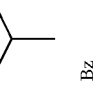 | H | Boc—Val |

TABLE 4-continued

Compounds of formula $$R_{501}-N\begin{array}{c}R_{12}\ H\ R_{551}\\ |\ |\ |\\ -C-C-N-R_{502}\\ |\ |\ |\\ H\ OPx\ R_{550}\\ R_{506}\end{array}$$

| Compound No. | R₅₀₁ | R₅₀₆ | R₁₂ | Px | R₅₅₀ | R₅₅₁ | R₅₀₂ |
|---|---|---|---|---|---|---|---|
| 256. | Boc—Val | H | Bz | P(O)(OH)₂ | Bz | H | Boc—Val |
| 257. | MC—Val | H | Bz | P(O)(OH)₂ | Bz | H | MC—Val |
| 258. | MC—Val | H | Bz | S(O)₂OH | (p-F)Bz | H | Boc |
| 259. | MC—Val | H | Bz | S(O)₂OH | (p-F)Bz | H | Z—Val |
| 260. | MC—Val | H | Bz | P(O)(OH)₂ | (p-F)Bz | H | Val |
| 261. | MC—Val | H | Bz | ![phosphate-phosphonate structure] | (p-F)Bz | H | ![morpholine-linked valine structure] |
| 262. | MC—Val | H | Bz | NO₂ | i-Pr | H | Boc |
| 263. | MC—Val | H | (p-F)Bz | ![phosphate-phosphonate structure] | (p-F)Bz | H | MC—Val |
| 264. | TMC—Val | H | Bz | ![phosphate-phosphonate structure] | Bz | H | TMC—Val |
| 265. | TMC—Val | H | Bz | ![phosphate-phosphonate structure] | i-Pr | H | TMC—Val |
| 266. | Asn | H | Bz | ![(carboxymethoxy)acetone structure] | (p-F)Bz | H | Boc |

TABLE 4-continued
Compounds of formula
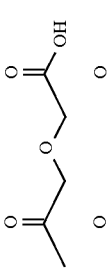
| Compound No. | $R_{501}$ | $R_{506}$ | $R_{12}$ | Px | $R_{550}$ | $R_{551}$ | $R_{502}$ |
|---|---|---|---|---|---|---|---|
| 267. | TFA | H | Bz | 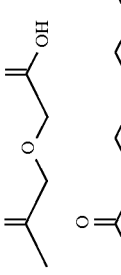 | (p-F)Bz | H | Boc |
| 268. | TFA | H | Bz |  | (p-F)Bz | H | Z—Val |
| 269. | TFA—Val | H | Bz | 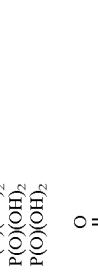 | i-Pr | H | 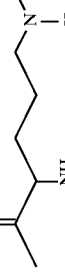 |
| 270. | Ac—Val | H | Bz | $P(O)(OH)_2$ | Bz | H | Ac |
| 271. | Ac—Val | H | Bz | $P(O)(OH)_2$ | $CH_2C_6H_{11}$ | H | Ac—Val |
| 272. | Ac—Val | H | Bz | $P(O)(OH)_2$ | (p-F)Bz | H | Ac—Val |
| 273. | Ac—Val | H | Bz | $P(O)(OH)_2$ | (p-CN)Bz | H | Ac—Val |
| 274. | Ac—Val | H | Bz | $P(O)(OH)_2$ | i-Pr | H | Ac—Val |
| 275. | Ac—Val | H | Bz |  | i-Pr | H |  |
| 276. | Ac—Ile | H | Bz | $P(O)(OH)_2$ | $CH_2C_6H_{11}$ | H | Ac—Ile |
| 277. | PhC(O)NH—Asn | H | Bz | $P(O)(OH)_2$ | i-Pr | H | Boc |
| 278. |  | H | | $P(O)(OH)_2$ | i-Pr | H | Boc |

TABLE 4-continued

Compounds of formula $$R_{501}-N(H)-C(R_{12})(H)-C(H)(OPx)-C(H)(R_{506})-N(R_{551})(R_{502})$$
with additional substituent $R_{550}$ on the central carbon

| Compound No. | $R_{501}$ | $R_{506}$ | $R_{12}$ | Px | $R_{550}$ | $R_{551}$ | $R_{502}$ |
|---|---|---|---|---|---|---|---|
| 279. | H₂N-C(O)-CH₂-CH(SBu)-C(O)- | H | Bz | P(O)(OH)₂ | i-Pr | H | Boc |
| 280. | PC-NH-C₆H₄-C(O)- | H | Bz | P(O)(OH)₂ | i-Pr | H | Boc |
| 281. | CH₃OC(O)-Val | H | Bz | P(O)(OH)₂ | i-Pr | H | CH₃OC(O)-Val |
| 282. | CH₃OC(O)-Val | H | Bz | CH₃-C(O)-CH₂-C(O)-NH₂ | (p-F)Bz | H | CH₃OC(O)-Val |
| 283 | CH₃OC(O)-Val | H | Bz | CH₃-C(O)-CH₂-C(O)-NH₂ | (p-CN)Bz | H | CH₃OC(O)-Val |
| 284. | triazolyl-CH₂CH₂-C(O)-NH-CH(iPr)-C(O)-CH₃ | H | Bz | CH₃-C(O)-CH₂-C(O)-NH₂ | (p-F)Bz | H | |
| 285. | triazolyl-CH₂CH₂-C(O)-NH-CH(iPr)-C(O)-CH₃ | H | Bz | CH₃-C(O)-CH₂-C(O)-NH₂ | i-Pr | H | triazolyl-CH₂CH₂-C(O)-NH-CH(iPr)-C(O)-CH₃ |

TABLE 4-continued
Compounds of formula
| Compound No. | $R_{501}$ | $R_{506}$ | $R_{12}$ | Px | $R_{550}$ | $R_{551}$ | $R_{502}$ |
|---|---|---|---|---|---|---|---|
| 286. | 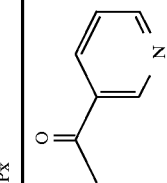 | H | (p-F)Bz | 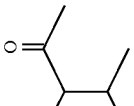 | Bz | H | 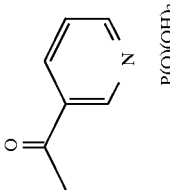 |
| 287. | 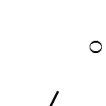 | H | Bz | 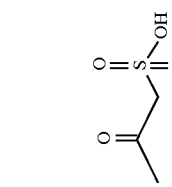 | i-Pr | H |  |
| 288. | 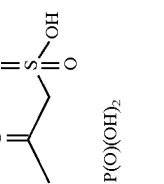 | H | $CH_2C_6H_{11}$ | $P(O)(OH)_2$ | i-Pr | H | 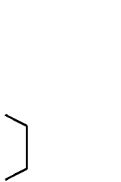 |
| 289. | $MeSO_2$ | H | Bz |  | Bz | H | BzC(O)—Val |
| 290. |  | H | Bz |  | n-Bu | H | N—SO$_2$—Val (morpholine) |
| 291. | Z | H | Bz | $P(O)(OH)_2$ | (3-methylbut-2-enyl-Ph) | H | Boc |

TABLE 4-continued
Compounds of formula
$R_{501}-N(R_{506})-C(R^{12})(H)-C(H)(H)-C(H)(OPx)-C(H)(R_{550})-N(R_{551})-R_{502}$
| Compound No. | $R_{501}$ | $R_{506}$ | $R_{12}$ | Px | $R_{550}$ | $R_{551}$ | $R_{502}$ |
|---|---|---|---|---|---|---|---|
| 292. | QCGlu | H | Bz | $P(O)(OH)_2$ | 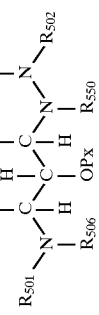 | | Boc |
| 293. | ZAsn | H | Bz | $P(O)(OH)_2$ | i-Pr | | Boc |

TABLE 5
Further examples of compounds of formula (I)
294. 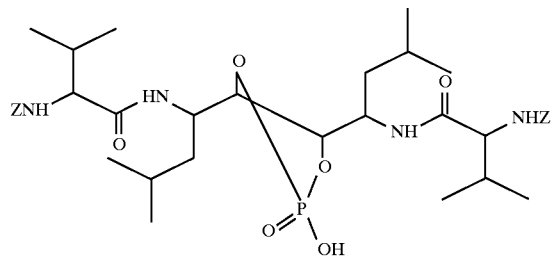
295. 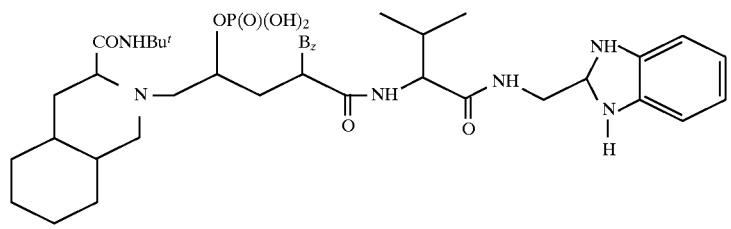
296. 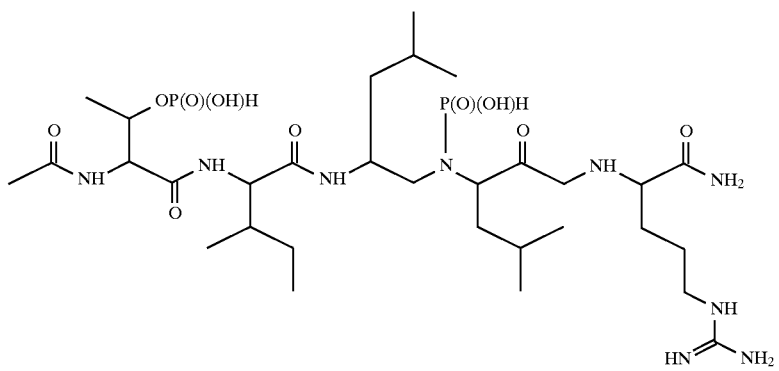
297. 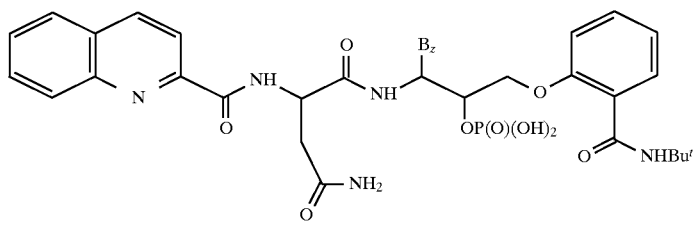
298. 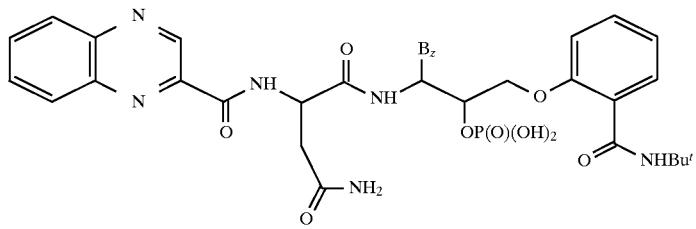
299. 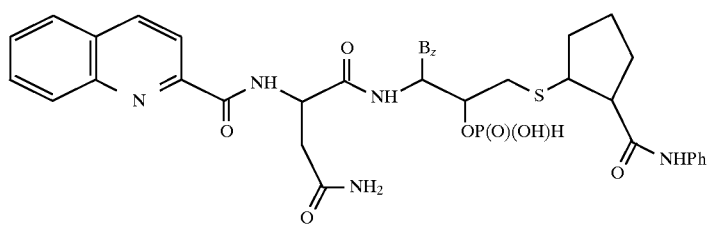

TABLE 5-continued
Further examples of compounds of formula (I)
300. 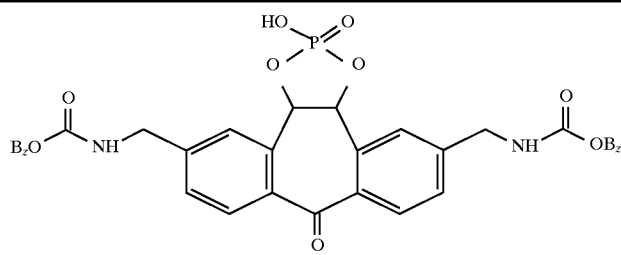
301. 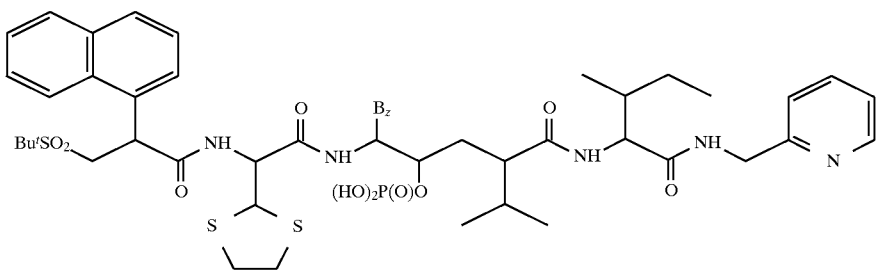
302. 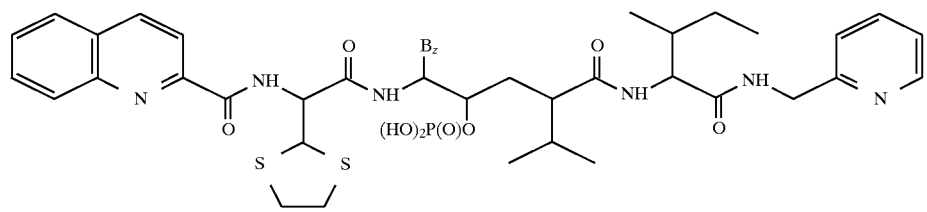
303. 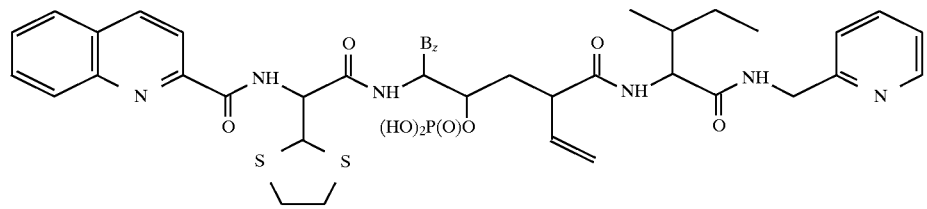
304. 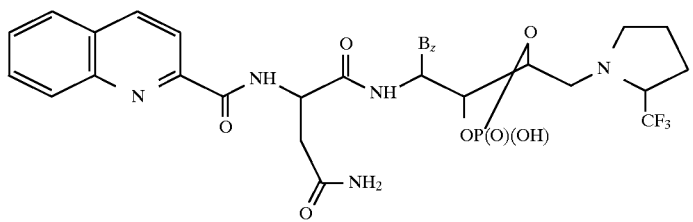
305. 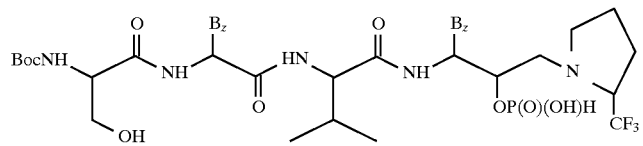
306. 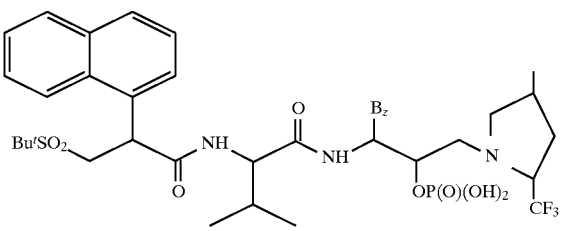

TABLE 5-continued
Further examples of compounds of formula (I)
307.
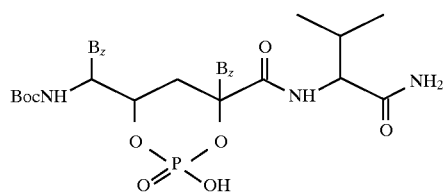
308.
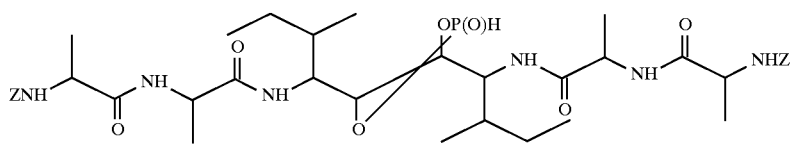
309.
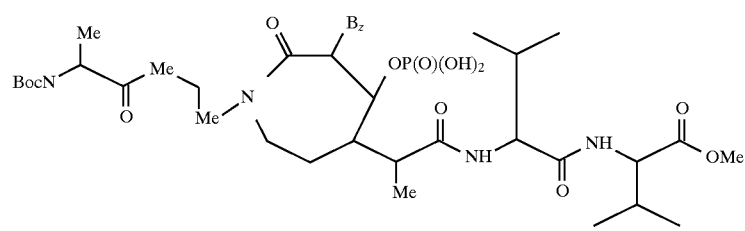
310.
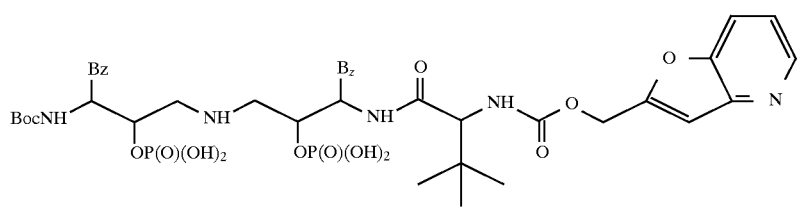
311.
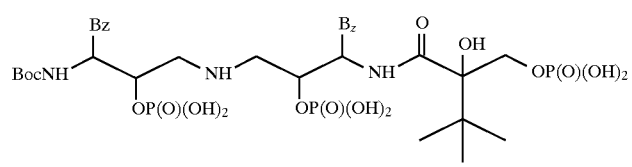
312.
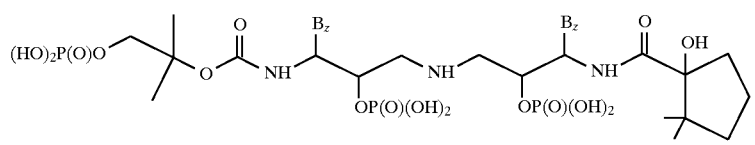
313.
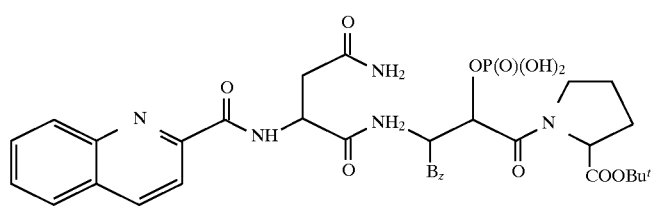
314.
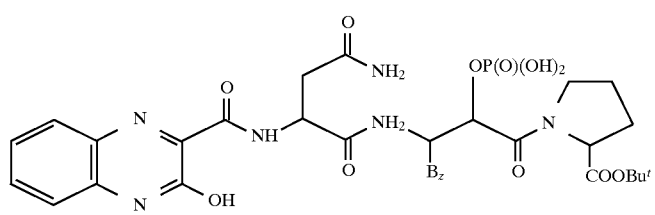

TABLE 5-continued

Further examples of compounds of formula (I)

315.

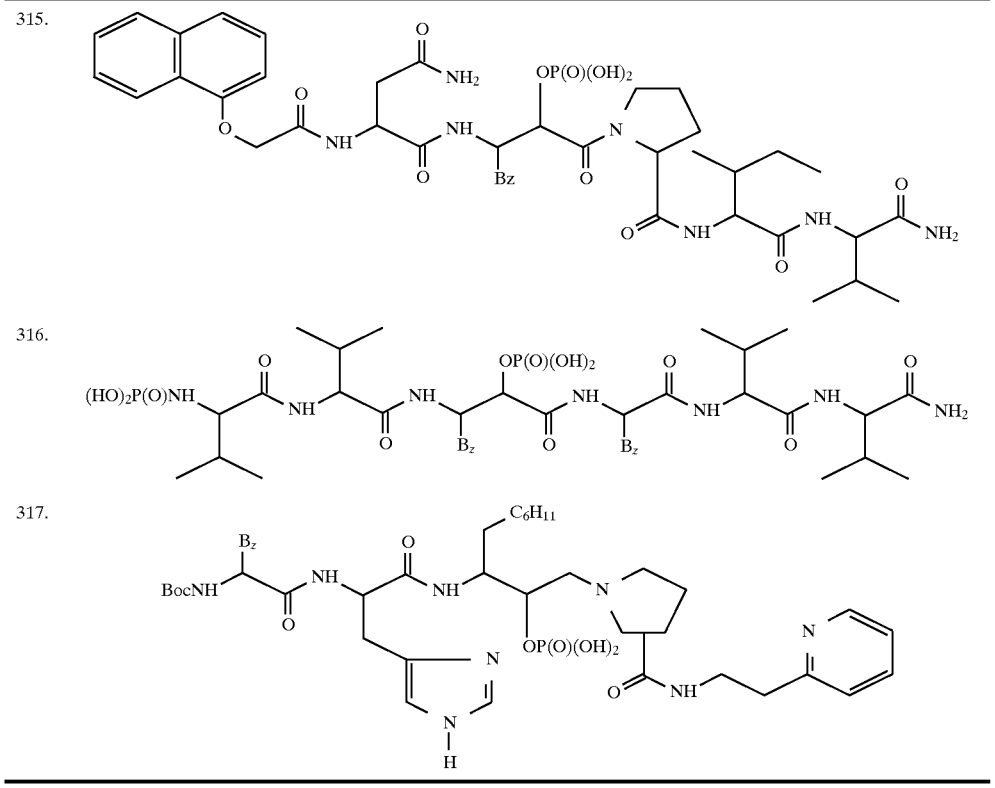

316.

317.

I claim:

1. A compound according to the formula (I) or a pharmaceutically acceptable salt or prodrug thereof:

$$W-(A)_n-B-(A^*)_m-V \qquad (I)$$

wherein n and m are both 1

B is

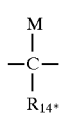

wherein $R_{14^*}$ is hydrogen and M is $OR_{15}$ wherein $R_{15}$ is a group Px;

Px is a solubilizing group which is labile in vivo;

V is a group

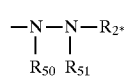

wherein $R_{2^*}$ is selected from the group consisting of optionally substituted $(C_1-C_{18})$acyl and $C(O)OR_{21}$ wherein $R_{21}$ is selected from hydrogen and $R_{20}$, and wherein $R_{20}$ is selected from the group consisting of optionally substituted $(C_1-C_{12})$alkyl,
optionally substituted $(C_2-C_{12})$alkenyl,
optionally substituted $(C_2-C_{12})$alkynyl,
optionally substituted $(C_3-C_{12})$cycloalkyl,
optionally substituted $(C_3-C_{12})$cycloalkyl $(C_1-C_6)$alkyl,
optionally substituted $(C_6-C_{12})$aryl,
optionally substituted $(C_6-C_{12})$aryl$(C_1-C_4)$alkyl,
optionally substituted $(C_6-C_{12})$acyl, and
optionally substituted heterocyclic $R_{50}$ and R51 are independently selected from and $R_{20}$ are previously defined, A and A* are

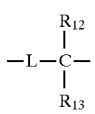

wherein L is a bond, $R_{13}$ is hydrogen and each $R_{12}$ independently is selected from the group consisting of hydrogen and $R_{20}$ as previously defined; and W is $R_1*X^*$, wherein $R_{1^*}$ is selected from the group represented by the formula $R_{401}NHCH(R_{400})C(O)$— wherein $R_{400}$ is the side chain of a naturally occurring amino acid and $R_{401}$ us quinoline-2-carbonyl; and X* is $NR_{10}$ wherein $R_{10}$ is selected from hydrogen and $R_{20}$ as previously defined.

2. A compound according to claim 1, wherein Px is selected from the group consisting of Px*,

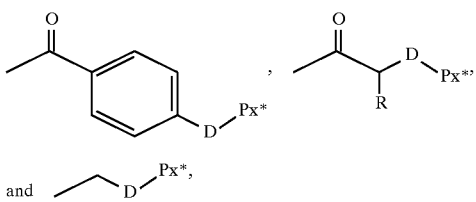

and 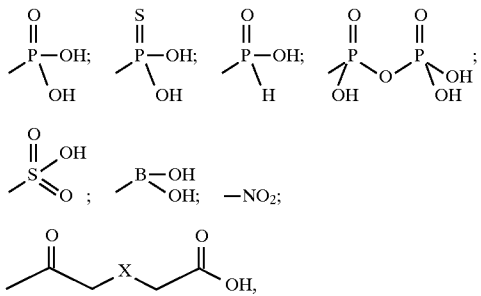

wherein D is O or S, R is H or $C_1$–$C_4$ alkyl, and wherein Px* is selected from:

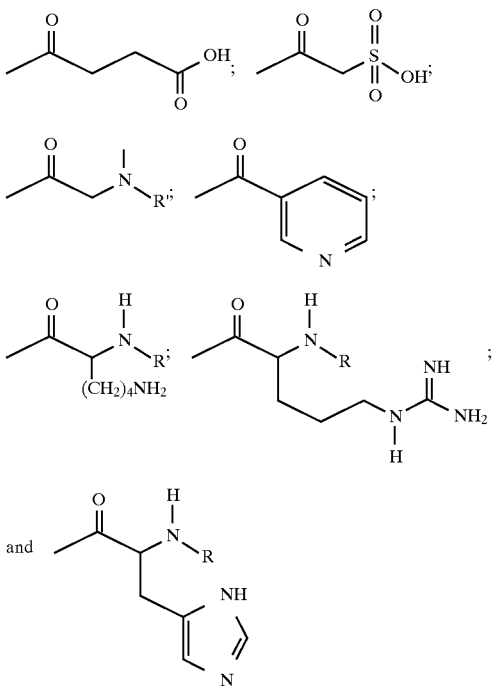

wherein X=O,S,S(O),S(O)$_2$;

wherein R' has the meaning of R.

3. A compound according to claim 2 wherein Px* is selected from the group consisting of

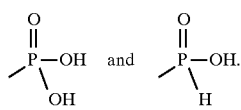

4. A compound according to claim 1 selected from the group consisting of derivatives of:
(i) t-butyl-3-isopropyl-3-[(2or S,3S)-2-hydroxy-3-(N-quinaldyl-L-valyl)-amino-4-phenylbutyl]carbazate (ii) t-butyl-3-isopropyl-3-[(2R or S,3S)-2-hydroxy-3-(N-quinaldyl-L-asparaginyl) amino-4-phenylbutyl] carbazate (iii) t-butyl-3-(1-methyl-3-phenylpropyl)-3-[2R or S, 3S)-2-hydroxy-3(N-quinaldyl-L-asparaginyl)amino-4-phenylbutyl]carbazate, (iv) 1-[2-(2-pyridyl)methoxycarbonylamino]-benzoyl-2-[(2R or S,3S)-2-hydroxy-3-(N-quinaldyl-L-asparaginyl)amino-4phenylbutyl]-2-isopropylhydrazine, (v) 1-trimethylacetyl-2-[2R or S,3S)-2-hydroxy-3(N-quinaldyl-L-asparaginyl)amino-4phenylbutyl]-2-isopropylhydrazine, (vi) 1-(t-butylamino)carbonyl-2-[(2R or S,3S)-2hydroxy-3(N-quinaldyl-L-asparaginyl)amino-4-phenylbutyl]-2-isopropylhydrazine, (viii) t-butyl-3-[2R or S,3S)-2-hydroxy-3-(N-quinaldyl-L-asparaginyl)-amino 4-phenylbutyl]carbazate, and (ix) t-butyl 3-cyclohexyl-3-[2R or S,3S)-2-hydroxy-3-(N-quinaldyl-L-asparaginyl) amino-4-phenylbutyl] carbazate, wherein the derivatives consist of compounds (i)–(vi), (viii) and (ix) in which the 2-hydroxy group is derivatized with a solubilizing group Px which is liable in vivo and Px is as previously defined.

5. A compound according to claim 4 wherein the solubilising group Px is selected from the group consisting of

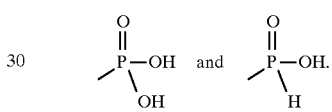

6. A compound according to claim 5, which compound is selected from the group consisting of:
t-butyl-3-isopropyl-3-[(2S, 3S)-2-phosphonooxy-3-(N-quinaldyl-L-asparaginyl)-amino-4-phenylbutylcarbazate and
t-butyl-3-isopropyl-3-[(2S, 3S)-2phosphitooxy-3-(N-quinaldyl-L-asparaginyl)amino-4-phenylbutylcarbazate.

7. The compound t-butyl 3-isopropyl-3-[(2S, 3S-2-phosphonooxy-3-(N-quinaldyl-L-asparaginyl)amino-4-phenylbutylcarbazate.

8. The compound t-butyl 3-isopropyl-3-[(2S, 3S)-2-phosphitooxy-3-(N-quinaldyl-L-asparaginyl)amino-4-phenylbutylcarbazate.

9. The pharmaceutical composition comprising an effective amount of a compound of claim 1 together with at least one pharmaceutically acceptable carrier, diluent, excipient and/or adjuvant.

10. A pharmaceutical composition comprising an effective amount of a compound of claim 2 together with at least one pharmaceutically acceptable carrier, diluent, excipient and/or adjuvant.

11. A pharmaceutical composition comprising an effective amount of a compound of claim 3 together with at least one pharmaceutically acceptable carrier, diluent, excipient and/or adjuvant.

12. A pharmaceutical composition comprising an effective amount of a compound of claim 4 together with at least one pharmaceutically acceptable carrier, diluent, excipient and/or adjuvant.

13. A pharmaceutical composition comprising an effective amount of a compound of claim 5 together with at least one pharmaceutically acceptable carrier, diluent, excipient and/or adjuvant.

14. A pharmaceutical composition comprising an effective amount of a compound of claim 6 together with at least one pharmaceutically acceptable carrier, diluent, excipient and/or adjuvant.

15. A pharmaceutical composition comprising an effective amount of a compound of claim 7 together with at least one pharmaceutically acceptable carrier, diluent, excipient and/or adjuvant.

16. A pharmaceutical composition comprising an effective amount of a compound of claim 8 together with at least one pharmaceutically acceptable carrier, diluent, excipient and/or adjuvant.

17. A method for inhibiting retroviral protease activity in a mammal, comprising administering to a mammal in need of such treatment an effective amount of a compound according to claim 1.

18. A method for inhibiting retroviral protease activity in a mammal, comprising administering to a mammal in need of such treatment an effective amount of a compound according to claim 2.

19. A method for inhibiting retroviral protease activity in a mammal, comprising administering to a mammal in need of such treatment an effective amount of a compound according to claim 3.

20. A method for inhibiting retroviral protease activity in a mammal, comprising administering to a mammal in need of such treatment an effective amount of a compound according to claim 4.

21. A method for inhibiting retroviral protease activity in a mammal, comprising administering to a mammal in need of such treatment an effective amount of a compound according to claim 5.

22. A method for inhibiting retroviral protease activity in a mammal, comprising administering to a mammal in need of such treatment an effective amount of a compound according to claim 6.

23. A method for inhibiting retroviral protease activity in a mammal, comprising administering to a mammal in need of such treatment an effective amount of a compound according to claim 7.

24. A method for inhibiting retroviral protease activity in a mammal, comprising administering to a mammal in need of such treatment an effective amount of a compound according to claim 8.

25. A method according to claim 17 wherein said retroviral protease is an HIV protease.

26. A method according to claim 18 wherein said retroviral protease is an HIV protease.

27. A method according to claim 19 wherein said retroviral protease is an HIV protease.

28. A method according to claim 20 wherein said retroviral protease is an HIV protease.

29. A method according to claim 21 where in said retroviral protease is an HIV protease.

30. A method according to claim 22 wherein said retroviral protease is an HIV protease.

31. A method according to claim 23 wherein said retroviral protease is an HIV protease.

32. A method according to claim 24, wherein said retroviral protease is an HIV protease.

* * * * *

UNITED STATES PATENT AND TRADEMARK OFFICE
CERTIFICATE OF CORRECTION

PATENT NO. : 5,888,992

DATED : March 30, 1999

INVENTOR(S) : Damian W. Grobelny

It is certified that error appears in the above-identified patent and that said Letters Patent is hereby corrected as shown below:

Claim 1, column 190, line 45, delete "$R_{50}$ and R51 are independently selected from and $R_{20}$ are" and insert -- $R_{50}$ and $R_{51}$ are independently selected from hydrogen and $R_{20}$ as --.

Claim 1, column 190, line 60, delete "us" and insert -- is --.

Claim 4, column 192, line 9, delete "4phenylbutyl" and insert -- 4-phenylbutyl --.

Claim 4, column 192, line 12, delete "4phenylbutyl" and insert -- 4-phenylbutyl --.

Claim 9, column 192, line 48, delete "The" and insert -- A --.

Signed and Sealed this

Fourteenth Day of September, 1999

Attest:

Q. TODD DICKINSON

*Attesting Officer*  *Acting Commissioner of Patents and Trademarks*